US011674139B2

(12) United States Patent
Linsley et al.

(10) Patent No.: US 11,674,139 B2
(45) Date of Patent: Jun. 13, 2023

(54) OLIGONUCLEOTIDES FOR TREATING EXPANDED REPEAT DISEASES

(71) Applicant: SAREPTA THERAPEUTICS, INC., Cambridge, MA (US)

(72) Inventors: Peter Linsley, Seattle, WA (US); Brian James Leppert, Kenmore, WA (US); Gunnar J. Hanson, Cambridge, MA (US)

(73) Assignee: Sarepta Therapeutics, Inc., Cambridge, MA (US)

( * ) Notice: Subject to any disclaimer, the term of this patent is extended or adjusted under 35 U.S.C. 154(b) by 0 days.

(21) Appl. No.: 16/038,580

(22) Filed: Jul. 18, 2018

(65) Prior Publication Data
US 2019/0100755 A1    Apr. 4, 2019

Related U.S. Application Data

(63) Continuation of application No. 14/360,890, filed as application No. PCT/US2012/067470 on Nov. 30, 2012, now Pat. No. 10,066,228.

(60) Provisional application No. 61/565,475, filed on Nov. 30, 2011.

(51) Int. Cl.
| C12N 15/113 | (2010.01) |
| C07F 9/6558 | (2006.01) |
| C07F 9/6561 | (2006.01) |
| C07H 21/04 | (2006.01) |
| C12Q 1/6883 | (2018.01) |
| C12N 15/11 | (2006.01) |

(52) U.S. Cl.
CPC ........ *C12N 15/113* (2013.01); *C07F 9/65583* (2013.01); *C07F 9/65616* (2013.01); *C07H 21/04* (2013.01); *C12N 15/111* (2013.01); *C12Q 1/6883* (2013.01); *C12N 2310/323* (2013.01); *C12N 2310/3231* (2013.01); *C12N 2310/3233* (2013.01); *C12N 2320/34* (2013.01); *C12Q 2600/156* (2013.01)

(58) Field of Classification Search
CPC ................ C12N 15/113; C12N 15/111; C12N 2310/323; C12N 2310/3231; C12N 2310/3233; C12N 2320/34; C07F 9/65583; C07F 9/65616; C12Q 1/6883; C12Q 2600/156; C07H 21/04
See application file for complete search history.

(56) References Cited

U.S. PATENT DOCUMENTS

| 9,161,948 B2 * | 10/2015 | Hanson | A61K 31/713 |
| 10,066,228 B2 * | 9/2018 | Linsley | C12N 15/111 |
| 2004/0006089 A1 | 1/2004 | Thureau et al. | |
| 2006/0287268 A1 | 12/2006 | Iversen et al. | |
| 2008/0194463 A1 | 8/2008 | Weller et al. | |
| 2010/0016215 A1 | 1/2010 | Moulton | |
| 2011/0269665 A1 * | 11/2011 | Kole | C12N 15/113 530/300 |
| 2011/0269820 A1 | 11/2011 | Singh et al. | |
| 2014/0329772 A1 | 11/2014 | Linsley et al. | |

FOREIGN PATENT DOCUMENTS

| JP | 2003-516965 A | 5/2003 |
| JP | 2011-236157 A | 11/2011 |
| WO | WO 2007/002390 A2 | 1/2007 |
| WO | WO 2008/018795 A1 | 2/2008 |
| WO | WO 2008/036127 A2 | 3/2008 |
| WO | WO 2010/120820 A1 | 10/2010 |
| WO | WO 2011/150408 A2 | 12/2011 |
| WO | WO 2012/150960 A1 | 11/2012 |
| WO | WO 2013/082551 A1 | 6/2013 |

OTHER PUBLICATIONS

Mulders et al. (Proceed. Nat. Acad. Sci. U.S.A. (2009) 106(33): 13915-13920) (Year: 2009).*
U.S. Appl. No. 14/360,890, filed Nov. 30, 2012, 2014/0303238, Oct. 9, 2014, U.S. Pat. No. 10,066,228, Sep. 4, 2018, Peter Linsley.
Japanese Office Action, JP Application No. 2014-544962, dated Sep. 6, 2017 (8 pages).
Kaya, I. et al., "The synthesis and characterization of oligo-N-4-aminopryridine, oligo-2[(pyridine-4-yl-imino)methyl] phenol and its some obigomer-metal complexes", Polymer, vol. 44; 7299-7309 (2003).
European Office Action, EP Application No. 12812432.8-1401, dated Apr. 1, 2016 (5 pages).
Prabahar, K. et al., "Effect of Phosphate Activating Group on Oligonucleotide Formation on Montmorillonite: The Regioselective Formation of 3' 5'-Linked Oligoadenylates", J. Am. Chem. Soc., vol. 116: 10914-10920 (1994).
Singh, N. et al., "A short antisense oligonucleotide masking a unique intronic mortif prevents skipping of a critical exon in spinal muscular atrophy", RNA Biology, vol. 6(3): 341-350 (2009).
Burghes, A.H.M., et al., "Antisense oligonucleotides and spinal muscular atrophy: skipping along", Genes and Development, vol. 24(15), pp. 1574-1579 (2010).
Cartegni L. et al., "Correction of disease-associated exon skipping by synthetic exon-specific activators," Nature Structural Biology, Nature Publishing Group, vol. 10 (2), pp. 120-125 (2003).

(Continued)

*Primary Examiner* — J. E. Angell
(74) *Attorney, Agent, or Firm* — Brian C. Trinque; Lathrop GPM LLP

(57) ABSTRACT

The invention provides for a method for selectively reducing the expression of a mutant mRNA and/or protein having an expanded nucleotide repeat relative to a wild-type mRNA, comprising contacting a cell with an antisense oligonucleotide of sufficient length and complementarity to the expanded nucleotide repeat. More particularly it relates to selectively reducing the expression of mutant Huntington protein associated with Huntington's disease. The antisense oligonucleotide comprising either a nucleotide or a repeated three nucleotide sequence as defined in the claims.

18 Claims, 16 Drawing Sheets

Specification includes a Sequence Listing.

(56) References Cited

OTHER PUBLICATIONS

Hua, Y., et al., "Enhancement of SMN2 exon 7 inclusion by antisense oligonucleotides targeting the exon," PLOS Biology, Public Library of Science, vol. 5(4), pp. 729-744 (2007).
International Preliminary Report on Patentability, PCT/US2012/067470, dated Jun. 30, 2014, pp. 1-7.
International Preliminary Report on Patentability, PCT/US2012/067475, dated Jun. 30, 2014, pp. 1-6.
International Search Report and Written Opinion, PCT/US2012/067475, dated Mar. 26, 2013, pp. 1-11.
Lim, S.R., et al., "Modulation of Survival Motor Neuron Pre-MRNA Splicing by Inhibition of Alternative 3' Splice Site Pairing," Journal of Biological Chemistry, American Society for Biochemistry and Molecular Biology, vol. 276 (48), pp. 45476-45483 (2001).
Sazani, P. et al., "Nuclear antisense effects of neutral, anionic and cationic oligonucleotide analogs," Nucleic Acids Research, Oxford University Press, vol. 29 (19), pp. 3965-3974 (2001).
Singh, N.N. et al., "An antisense microwalk reveals critical role of an intronic position linked to a unique long-distance interaction in pre-mRNA splicing", RNA, vol. 16(6), pp. 1167-1181 (2010).
Swenson, D.L., et al., "Chemical Modifications of Antisense Morpholino Oligomers Enhance Their Efficacy against Ebola Virus Infection," Antimicrobial Agents and Chemotherapy, vol. 53(5), pp. 2089-2099 (2009).

\* cited by examiner

Figure 7

|  | modification | EC50 (µM) | Std.Dev | selectivity (wt/mutant) |
|---|---|---|---|---|
| wt | LNA | 0.98 | 0.40 | 6.8 |
| mutant | LNA | 0.14 | 0.04 | |
| wt | PMO | 43.8 | 29.6 | 93.9 |
| mutant | PMO | 0.47 | 0.49 | |
| wt | APN | 1.28 | 0.44 | 12.7 |
| mutant | APN | 0.10 | 0.03 | |

Figure 9

|  | modification | EC50 (μM) | Std.Dev | selectivity (wt/mutant) |
|---|---|---|---|---|
| wt | PMO | 74.6 | 48.3 | 165.0 |
| mutant | PMO | 0.45 | 0.40 | |
| wt | APN | 0.96 | 0.29 | 11.7 |
| mutant | APN | 0.08 | 0.02 | |

APN-related cationic modifications aT(APN)

mapT plus-related cationic modifications plusBase medaT

EtpipT

OLIGONUCLEOTIDES FOR TREATING EXPANDED REPEAT DISEASES

RELATED APPLICATIONS

This application is a continuation of U.S. application Ser. No. 14/360,890, filed on May 27, 2014, which is a 35 U.S.C. § 371 filing of International Application No. PCT/US12/67470, filed on Nov. 30, 2012, which claims priority to U.S. Provisional Application 61/565,475, filed on Nov. 30, 2011, the entire contents of which is incorporated herein by reference in its entirety.

SEQUENCE LISTING

The instant application contains a Sequence Listing which has been submitted electronically in ASCII format and is hereby incorporated by reference in its entirety. Said ASCII copy, created on May 31, 2018, is named 598791_SPT-8105US_SL.txt and is 14,868 bytes in size.

FIELD OF THE INVENTION

The invention relates to the use of an antisense compound for selectively reducing the expression of a mutant transcript or protein produced from a mutant expanded nucleotide repeat containing allele associated with an expanded repeat disease relative to the corresponding wild-type transcript or protein. In one embodiment, it relates to the allele-specific inhibition of mutant Huntington expression in Huntington's disease.

BACKGROUND

Nearly 30 hereditary disorders in humans result from an increase in the number of copies of simple repeats in genomic DNA. These DNA repeats seem to be predisposed to such expansion because they have unusual structural features, which disrupt the cellular replication, repair and recombination machineries. The presence of expanded DNA repeats alters gene expression in human cells, leading to disease.

One such hereditary disorder is Huntington's disease (HD). HD is a fatal, neurodegenerative disorder with no cure that is associated with cognitive decline, dementia, and loss of motor coordination. It is characterized by the progressive and heritable increase in length of CAG trinucleotide repeats that encode a polyglutamine tract, in the coding region of the Huntington (HTT) gene. These repeats can increase in number from one generation to another. The normal allele of the HTT gene contains less than 36 CAG repeats, whereas the mutant allele contains more than 36 repeats. Most HD patients carry one normal allele and a mutant disease-causing allele. Functionally, the aberrant accumulation of CAG repeats is thought to confer a toxic gain-of-function to the mutant HD protein, causing it to aggregate, form protein deposits (i.e., inclusion bodies), and induce cell death. Disease severity generally reflects the extent of expanded repeats in the mutant HTT protein.

Therapeutic options for HD include small molecule drugs like haloperidol, tetrabenazine, clonazepam, fluoxitine, and sertraline that are designed to control the phenotypic manifestations of the disease. While these drugs can improve quality of life for patients with HD, they are not expected to significantly reverse or alter disease progression or increase life expectancy nor do they address the underlying molecular mechanisms of the disease.

Another disease characterized by an expanded nucleotide repeat in genomic DNA is amyotrophic lateral sclerosis (ALS). ALS is a fatal neurodegenerative disease characterized clinically by progressive paralysis leading to death from respiratory failure, typically within two to three years of symptom onset. ALS is the third most common neurodegenerative disease in the Western world, and there are currently no effective therapies. A proportion of ALS patients are characterized by a large hexanucleotide (GGGGCC) repeat expansion, for example, in the C9ORF72 gene (see, e.g., Renton et al., Neuron 2011; 72:257-68 and DeJesus-Hernandez et al., Neuron 2011; 72:245-56).

Myotonic dystrophy type 1 (DM1) and type 2 (DM2) are associated with long polyCUG and polyCCUG repeats in the 3'-UTR and intron 1 regions of the transcript dystrophia myotonica protein kinase (DMPK) and zinc finger protein 9 (ZNF9), respectively. While normal individuals have as many as 30 CTG repeats, DMI patients carry a larger number of repeats ranging from 50 to thousands. The severity of the disease and the age of onset correlates with the number of repeats. Patients with adult onsets show milder symptoms and have less than 100 repeats, juvenile onset DM1 patients carry as many as 500 repeats and congenital cases usually have around a thousand CTG repeats. The expanded transcripts containing CUG repeats form a secondary structure, accumulate in the nucleus in the form of nuclear foci and sequester RNA-binding proteins (RNA-BP).

There is a need for new and/or improved therapeutic approaches to treating expanded repeat diseases. One possible route to treating expanded repeat diseases, such as HD and ALS, would be selective reduction or elimination of the gene product of a mutant disease-causing allele which contains expanded repeats.

SUMMARY OF THE INVENTION

The invention includes, in one aspect, a method for selectively reducing the expression of a mRNA or protein produced from a mutant expanded nucleotide repeat containing allele relative to a wild-type allele. The method comprises contacting a cell with an antisense oligonucleotide of sufficient length and complementarity to the expanded nucleotide repeat such that it specifically hybridizes to the mutant mRNA. In some embodiments, the antisense oligonucleotide of the invention has APN linkages. In other embodiments, the antisense oligonucleotide has a different type of cationic linkage, such as etpip linkages.

In one embodiment, the invention relates to an antisense oligonucleotide of 10-40 nucleotides in length having a sequence complementary to an expanded DNA repeat which is associated with a human disease, wherein the antisense comprises a nucleotide having a formula:

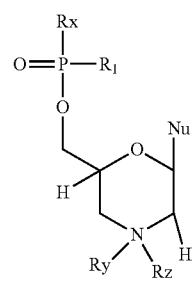

wherein Nu is a nucleobase;

$R_1$ is a moiety of the formula

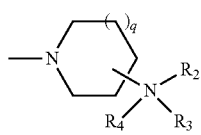

q is 0, 1, 2, 3 or 4;

$R_2$ is selected from the group consisting of hydrogen, $C_1$-$C_5$ alkyl, and a formamidinyl moiety, and $R_3$ is selected from the group consisting of hydrogen and $C_1$-$C_5$ alkyl, or $R_2$ and $R_3$ are joined to form a 5-7 membered heterocyclic ring optionally containing an oxygen hetero atom, where the ring may be optionally substituted with a substituent selected from the group consisting of $C_1$-$C_5$ alkyl, phenyl, halogen, and aralkyl;

$R_4$ is selected from the group consisting of null, hydrogen, a $C_1$-$C_6$ alkyl and aralkyl;

$R_x$ is selected from the group consisting of HO—, a nucleotide, a cell penetrating peptide moiety, and piperazinyl;

$R_y$ is selected from the group consisting of hydrogen, a $C_1$-$C_6$ alkyl, a nucleotide, a peptide moiety, an amino acid, a formamidinyl moiety, and acyl; and, $R_z$ is selected from the group consisting of null, hydrogen, a $C_1$-$C_6$ alkyl, and acyl; and pharmaceutically acceptable salts thereof.

In some embodiments, Nu is selected from the group consisting of adenine, guanine, thymine, uracil, cytosine, and hypoxanthine. In one embodiment, Nu is thymine or uracil.

In one embodiment, $R_1$ is selected from the group consisting of

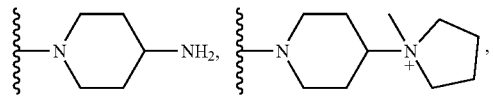

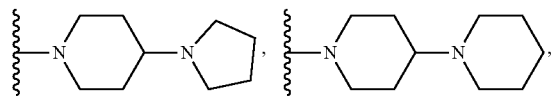

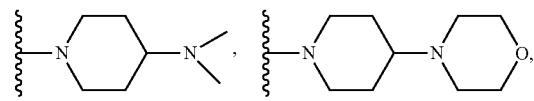

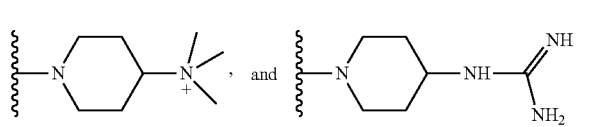

In yet another embodiment, the nucleotide has the formula:

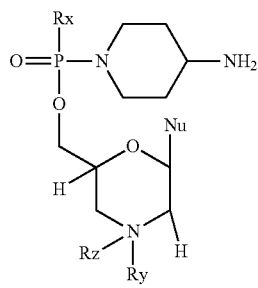

wherein Rx, Ry, Rz, and Nu are as stated previously.

In other embodiments, an antisense oligonucleotide of the invention includes a sequence selected from the group consisting of (CCG)n (SEQ ID NO: 27), (CTG)n (SEQ ID NO: 28), (TTC)n (SEQ ID NO: 29), (NGC)n (SEQ ID NO: 30), (GNC)n (SEQ ID NO: 31), (CAGG)n (SEQ ID NO: 32), (AGAAT)n (SEQ ID NO: 33), and (CGCG$_4$CG$_4$)n (SEQ ID NO: 34), wherein N is any nucleotide and n is from 3 to 10. In one embodiment the sequence is (GCT)$_7$ (SEQ ID NO: 35) and Ry is optionally a G nucleotide.

In some embodiments, the antisense oligonucleotide is useful for treating a human disease associated with an expanded repeat, such as Huntington's disease, amyotrophic lateral sclerosis (ALS), and myotonic dystrophy type 1 and type 2.

In yet other embodiments, an oligonucleotide of the invention comprises a repeated three nucleotide sequence having the formula:

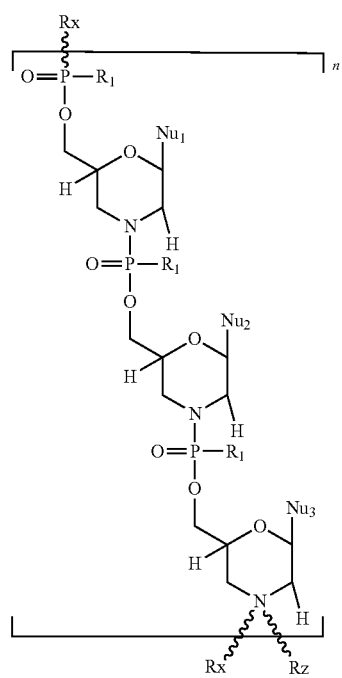

Nu$_1$, Nu$_2$ and Nu$_3$ are nucleobases selected from the group consisting of adenine, guanine, thymine, uracil, cytosine, and hypoxanthine;

n is from about 3 to about 10 representing the number of repeats of the nucleotide sequence (Nu$_1$, Nu$_2$, Nu$_3$);

R$_1$ is a moiety of the formula

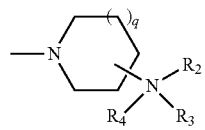

q is 0, 1, 2, 3 or 4;

R$_2$ is selected from the group consisting of hydrogen, C$_1$-C$_5$ alkyl, and a formamidinyl moiety, and R$_3$ is selected from the group consisting of hydrogen and C$_1$-C$_5$ alkyl, or R$_2$ and R$_3$ are joined to form a 5-7 membered heterocyclic ring optionally containing an oxygen hetero atom, where the ring may be optionally substituted with a substituent selected from the group consisting of C$_1$-C$_5$ alkyl, phenyl, halogen, and aralkyl;

R$_4$ is selected from the group consisting of null, hydrogen, a C$_1$-C$_6$ alkyl and aralkyl;

R$_x$ is selected from the group consisting of HO—, a nucleotide, a cell penetrating peptide moiety, and piperazinyl;

R$_y$ is selected from the group consisting of hydrogen, a C$_1$-C$_6$ alkyl, a nucleotide, a peptide moiety, an amino acid, a formamidinyl moiety, and acyl; and, R$_z$ is selected from the group consisting of null, hydrogen, a C$_1$-C$_6$ alkyl, and acyl; and pharmaceutically acceptable salts thereof.

In some embodiments, the three nucleotide sequence is selected from the group consisting of (CCG)n (SEQ ID NO: 27), (CTG)n (SEQ ID NO: 28), (TTC)n (SEQ ID NO: 29), (NGC)n (SEQ ID NO: 30), (GNC)n (SEQ ID NO: 31), wherein N is any nucleotide. In one embodiment, the oligonucleotide comprises a sequence (GCT)n (SEQ ID NO: 45), wherein n is from about 3 to about 10, and comprises at least one internucleoside linkage that is positively charged at physiological pH. In other embodiments, the repeated three nucleotide sequence is (GCT)$_7$ (SEQ ID NO: 35) and Ry is optionally a G nucleotide.

Other embodiments relate to an oligonucleotide comprising a repeated four, five, or six nucleotide sequence. A representative 4 nucleotide sequence has a formula:

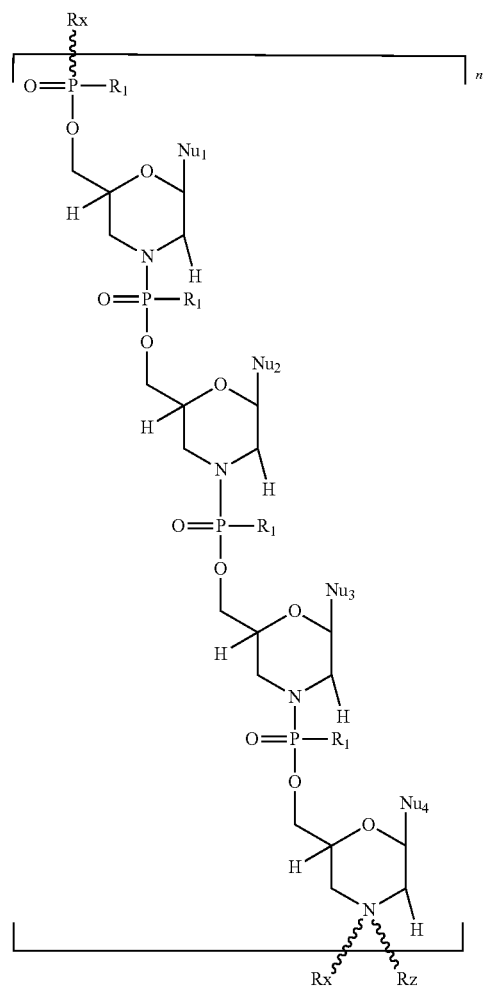

Nu$_1$, Nu$_2$, Nu$_3$, and Nu$_4$ (or Nu$_5$, Nu$_6$ etc.) are nucleobases selected from the group consisting of adenine, guanine, thymine, uracil, cytosine, and hypoxanthine;

n is an integer from about 3 to about 10 representing the number of repeats of the nucleotide sequence (Nu$_1$, Nu$_2$, Nu$_3$, Nu$_4$ optionally Nu$_5$, Nu$_6$, etc.);

R$_1$ is a moiety of the formula

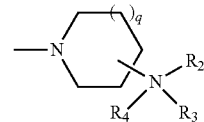

q is 0, 1, 2, 3 or 4;

R$_2$ is selected from the group consisting of hydrogen, C$_1$-C$_5$ alkyl, and a formamidinyl moiety, and R$_3$ is selected from the group consisting of hydrogen and C$_1$-C$_5$ alkyl, or R$_2$ and R$_3$ are joined to form a 5-7 membered heterocyclic ring optionally containing an oxygen hetero atom, where the ring may be optionally substituted with a substituent selected from the group consisting of C$_1$-C$_5$ alkyl, phenyl, halogen, and aralkyl;

R$_4$ is selected from the group consisting of null, hydrogen, a C$_1$-C$_6$ alkyl and aralkyl;

$R_x$ is selected from the group consisting of HO—, a nucleotide, a cell penetrating peptide moiety, and piperazinyl;

$R_y$ is selected from the group consisting of hydrogen, a $C_1$-$C_6$ alkyl, a nucleotide, a peptide moiety, an amino acid, a formamidinyl moiety, and acyl; and, $R_z$ is selected from the group consisting of null, hydrogen, a $C_1$-$C_6$ alkyl, and acyl; and pharmaceutically acceptable salts thereof.

In one embodiment, the antisense oligonucleotide is uncharged. In additional embodiments, the antisense oligonucleotide is charged. For example, one or more internucleotide linkages in the antisense oligonucleotide may have an cationic linkage such as an APN modification. The modified oligonucleotides contain nucleobases T, A, C, G, U or an analog thereof. Preferably the modified internucleotide linkage is derived from a T, C or A subunit.

In some embodiments, the antisense oligonucleotide is conjugated to a peptide moiety, such as a cell penetrating peptide transporter, for example an arginine-rich peptide (e.g., (Arg)$_6$Gly (SEQ ID NO: 36)).

In one embodiment, the antisense oligonucleotide comprising a repeated four nucleotide sequence is (CAGG)n, wherein n is 3-10 (SEQ ID NO: 32). Such oligonucleotides are useful to treat myotonic dystrophy type 1. In another embodiment, the antisense oligonucleotide comprising a repeated five nucleotide sequence is (AGAAT)n, wherein n is 3-10 (SEQ ID NO: 33). Such oligonucleotides are useful to treat Spinocerebellar ataxia 10. In yet another embodiment, the antisense oligonucleotide comprising a repeated six nucleotide sequence is (GGCCCC)n, wherein n is 3-10 (SEQ ID NO: 37). Such oligonucleotides are useful to treat amyotrophic lateral sclerosis (ALS).

Yet other embodiments of the invention are directed to an antisense oligonucleotide comprising a sequence set forth in Table I (and the Sequence Listing). Such antisense oligonucleotides are useful to treat a disease as set forth in Table I.

Other aspects of the invention relate to pharmaceutical compositions comprising an antisense oligonucleotide of the invention and a pharmaceutically acceptable carrier as well the use of such oligonucleotides in the manufacture of a medicament for treating diseases associated with expanded DNA repeats. Such compositions can be administered to subjects to treat diseases associated with expanded DNA repeats such as Huntington's disease, amyotrophic lateral sclerosis (ALS), and myotonic dystrophy type 1 and type 2.

Yet other aspects of the invention relate to methods of diagnosing a hereditary disorder associated with an expanded DNA repeat by Northern Blotting comprising:
a. extraction of total RNA from a homogenized tissue sample or cells;
b. isolating the mRNA;
c. separating the mRNA by size using gel electrophoresis;
d. transferring the mRNA to a membrane;
e. immobilizing the mRNA to the membrane; and
f. using a probe to detect an expanded repeat, wherein the probe is an oligonucleotide of the invention.

Another aspect relates to a method for determining responsiveness of a subject with a polynucleotide repeat disorder to treatment with oligonucleotide therapy. This method comprises:
i. isolating cells from the subject;
ii. culturing the cells;
iii. introducing an oligonucleotide into the cells;
iv. isolating mRNA or protein from the cells;
v. reverse transcribing and amplifying the mRNA using gene specific primers to a polynucleotide repeat disease-causing transcript, wherein the gene specific primers flank both ends of the polynucleotide repeat;
vi. quantifying the levels of a mutant polynucleotide repeat disease-causing mRNA or protein and a reference wild-type mRNA or protein; and
vii. comparing levels of the mutant polynucleotide repeat disease-causing mRNA or protein with levels of the reference wild-type mRNA or protein, and
viii. determining that the subject is responsive to oligonucleotide therapy if levels of the mutant polynucleotide repeat disease-causing mRNA or protein is lower than that of the reference wild-type mRNA or protein.

The intensity of the gel band representing the wild-type or mutant HTT allele from GM04281 fibroblast cells (Coriell) was normalized to the intensity of the respective wild-type or mutant band of the lowest treated sample. Each point represents the mean of the normalized expression levels from two replicates at each concentration, and two independent experiments were combined to yield the above dataset. Gel intensity quantification was performed with ImageQuant (GE). Intensity normalization, EC50 calculation, and selectivity were analyzed with Microsoft Excel and R. Data points and curves were plotted in Graphpad Prism.

FIG. 7: EC50 and selectivity of LNA, PMO, and APN oligonucleotides. Compounds are the same as those described in FIG. 6. mRNA expression analysis of the mutant and wild-type HTT alleles from GM04281 fibroblasts nucleofected with locked nucleic acid (LNA), PMO, or APN oligonucleotides was performed as described in FIG. 6. Mean EC50 values for each allele were calculated from the dataset presented in FIG. 6, as well as selectivity for the mutant allele was calculated from the EC50 of the wild-type and mutant alleles from fibroblasts nucleofected with the same oligonucleotide, using R and Graphpad Prism.

The data shows that the PMO and APN oligonucleotides show a higher selectivity for the mutant allele than LNA. Moreover, the potency of the APN oligonucleotide, based on EC50 values, is improved over the PMO oligonucleotide.

Figure 8:
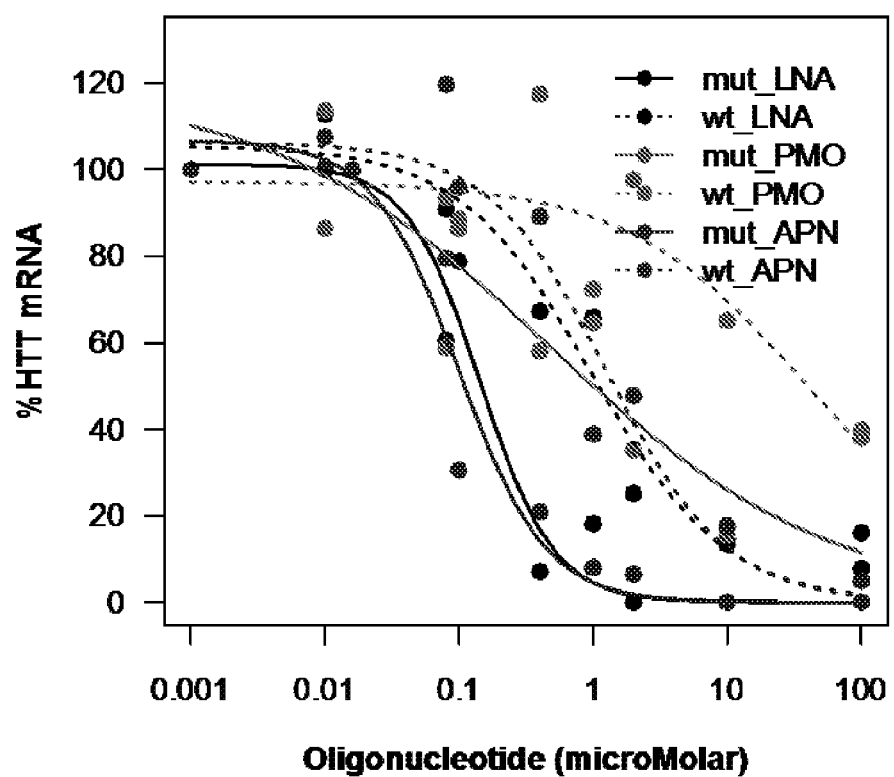

FIG. 8: Dose response curves from oligonucleotide-treated Huntington's Disease patient fibroblasts. Compounds are the same as those described in FIG. 6. This data was analyzed in the same fashion as FIG. 6, however three independent experiments were combined. Data from all oligonucleotides are plotted on the same graph.

FIG. 9: PMO and APN compounds show selectivity for mutant HTT mRNA. This data was analyzed in the same fashion as the table in FIG. 7, however three independent experiments were combined.

Figure 10:
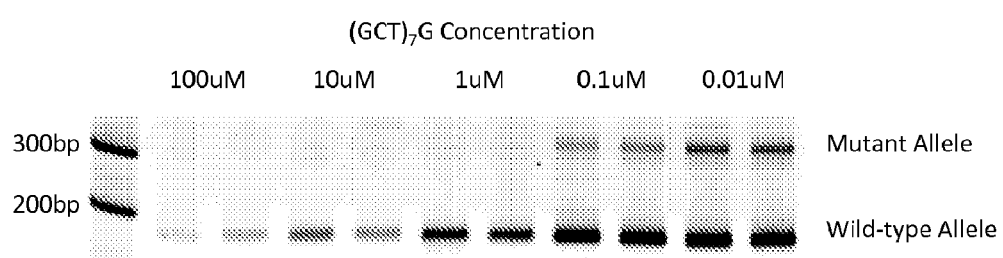

FIG. 10: RT-PCR of mutant and wild-type HTT alleles. RNA from GM04281 fibroblasts nucleofected with the apn (GCT)7G (SEQ ID NO: 21) oligonucleotide at the indicated concentrations were RT-PCR amplified as described in the Methods. Gels containing the resulting reactions were analyzed as described in the Methods and in FIG. 6.

Figure 11:
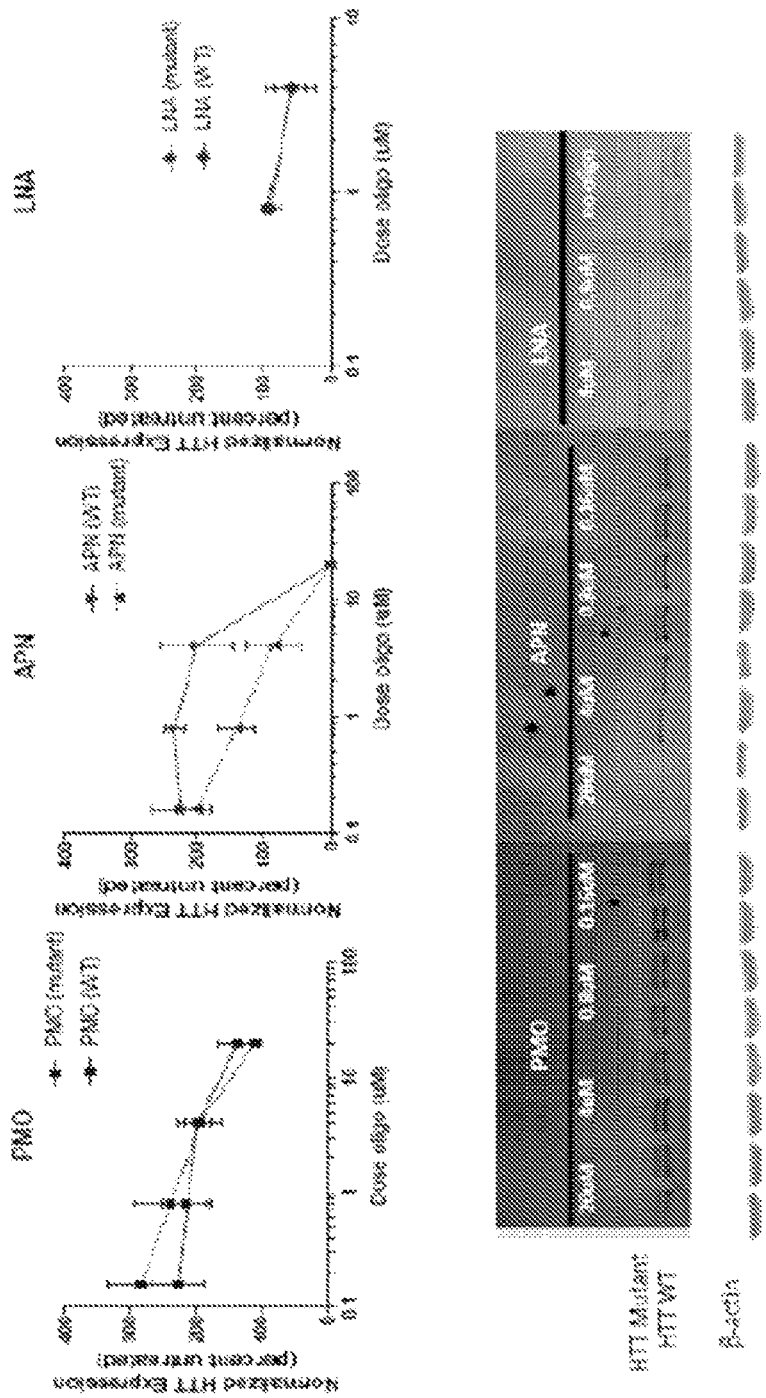

FIG. 11: PMO and APN, but not LNA compounds selectively reduce the expression of mutant HTT protein relative to wild-type HTT protein. Compounds are the same as those described in FIG. 6. Protein expression analysis of mutant and wild-type HTT protein from GM04281 fibroblasts nucleofected with PMO (left panel), APN (middle panel), or LNA (right panel) oligonucleotides was performed as described in Example 24. Three days after nucleofection, protein lysates were prepared. Equal amounts of total protein from each treated sample were run on duplicate tris-acetate SDS-PAGE gels and transferred to nitrocellulose. Blots were probed with an anti-HTT (MAB2166, Millipore) or anti-β-actin (A1978, Sigma) primary antibody followed by a cy5-congugated secondary antibody. The resulting blots were scanned on a Typhoon Trio (GE) and signal intensity of mutant and normal HTT protein were quantified separately with ImageQuant (GE) software (bottom panel). Signal intensity of the normal (lower) and mutant (upper) HTT bands was normalized to the β-actin signal within each lane, and then each HTT band was normalized to the corresponding normal or mutant HTT band intensity from an untreated control sample on a separate blot. Protein expression results are plotted for each allele (normal, solid line; mutant, dashed line) as the mean percent of HTT protein expression, +/−1 SD.

Figure 12:
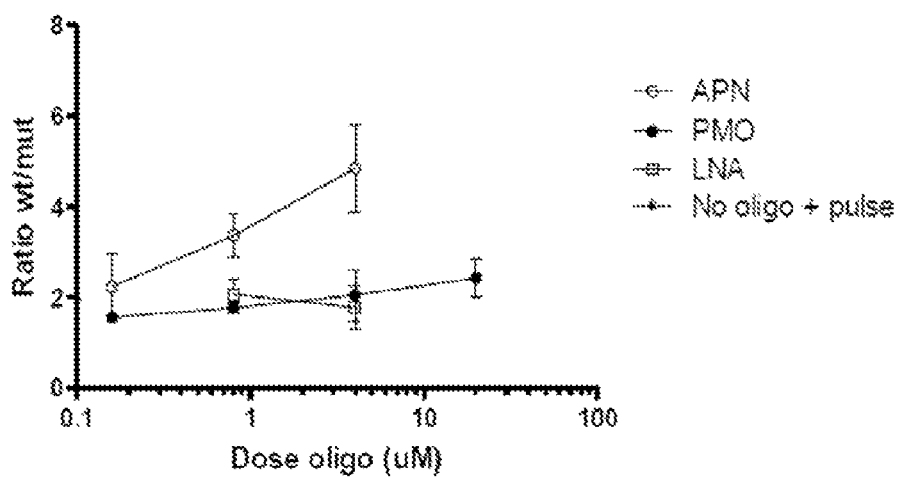

FIG. 12: APN-modified PMO selectively reduces the expression of mutant HTT protein relative to wild-type HTT protein. Data from FIG. 11 was used to determine and plot the ratio of wild-type to mutant HTT protein expression for each of PMO, APN, and LNA-modified oligonucleotides.

Figure 13:
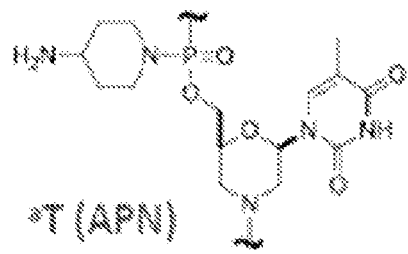
Figure 13:
Figure 13:
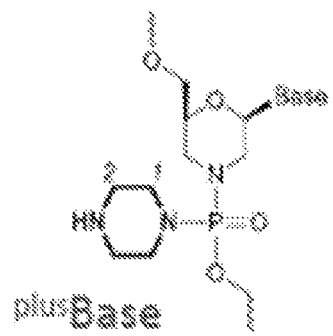
Figure 13:
Figure 13:
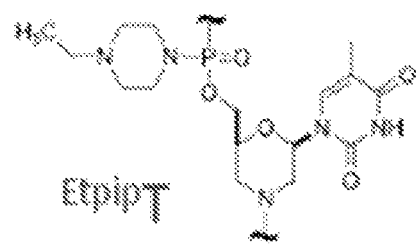

FIG. 13: Exemplary structures of APN- and plus-related cationic modifications. Shown are exemplary species of APN-related and plus-related cationic modifications. APN-related modifications include APN and map, and plus-related modifications include plus, meda, and etpip. Although the exemplified modifications relate to thymine, any base (e.g., thymine, cytosine, guanine, adenine) can be modified with the APN-related and plus-related cationic modifications.

Figure 14:
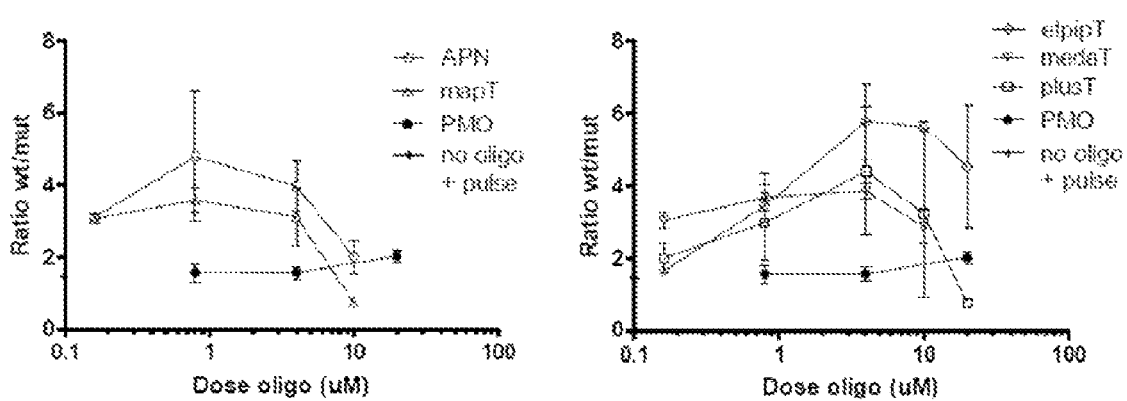

FIG. 14: Oligonucleotides with APN-related and plus-related backbone modifications selectively reduce the expression of mutant HTT protein relative to wild-type HTT protein. GM04281 fibroblasts were nucleofected as described in FIG. 11 with the indicated modified oligonucleotides at various concentrations (0.16 tiM, 0.8 tiM, 10 tiM, and 20 tiM), and the ratio of wild-type to mutant HTT protein expression was determined as described in FIGS. 11 and 12. APN- and mapT-modified oligonucleotides (left panel), and etpipT, medaT, and plusT-modified oligonucleotides (right panel) selectively reduced the expression of mutant HTT protein relative to wild-type HTT protein.

Figure 15:
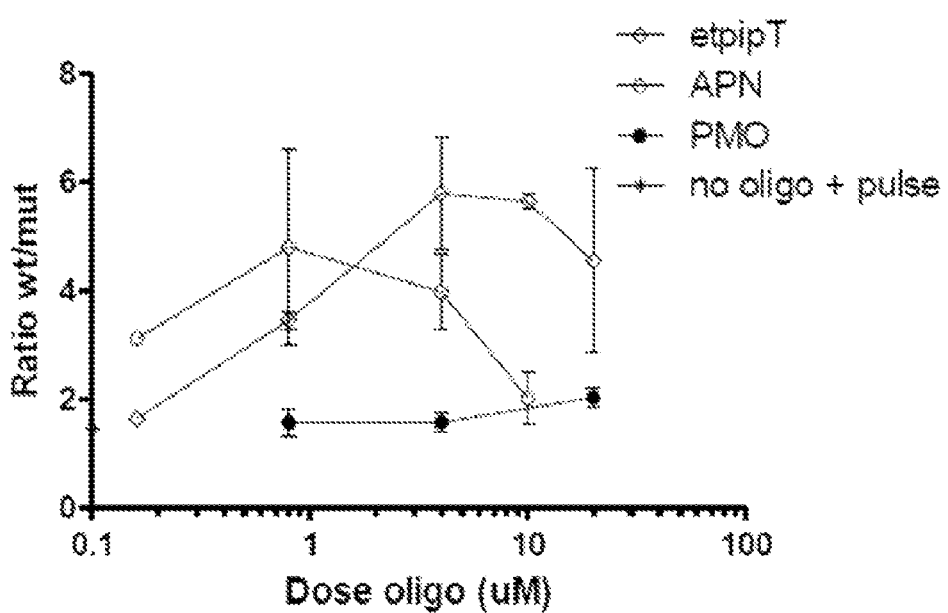

FIG. 15: APN- and etpip-modified oligonucleotides show high selectivity for mutant HTT protein relative to wild-type HTT protein. For comparison, data for APN, etpipT, PMO, and control from FIG. 14 were plotted onto the same graph. While both APN- and etpipT-modified oligonucleotides exhibited high selectivity for reducing the expression of mutant HTT relative to wild-type HTT, APN showed a higher selectivity for mutant HTT at lower doses.

Figure 16:
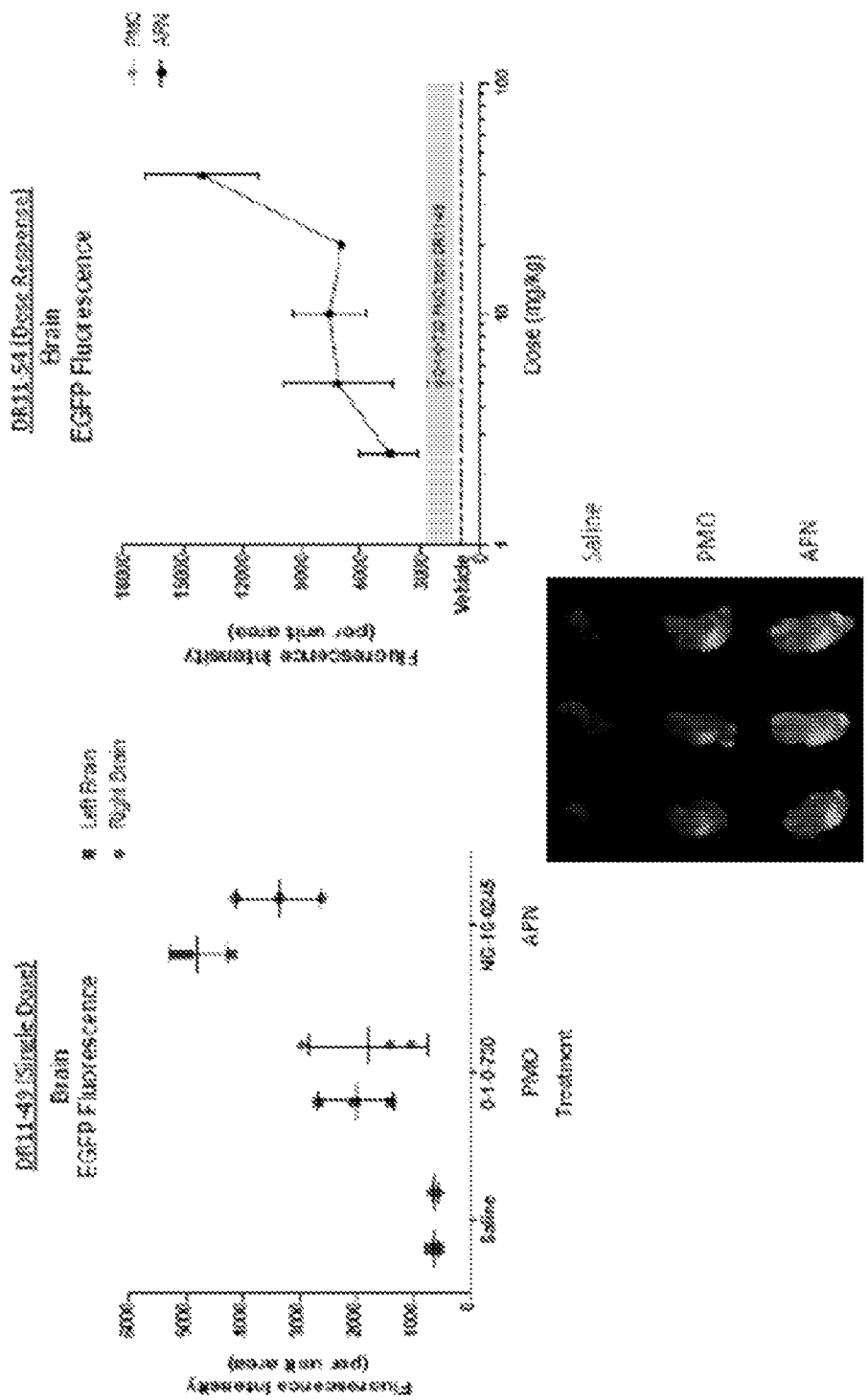

FIG. 16: APN modification enhances EGFP activity compared to PMO following ICV injection. The transgenic eGFP mouse model in which the eGFP-654 transgene is expressed uniformly throughout the body has been described previously (Sazani, Gemignani et al. 2002). This model uses a splicing assay for activity in which the modified oligomers of the present invention block aberrant splicing and restore correct splicing of the modified enhanced green fluorescent protein (eGFP) pre-mRNA. The level of translated eGFP is proportional to the potency of the antisense oligomers and their concentration at the site of action. This animal model provides an in vivo assay for antisense oligonucleotide-induced splice correction via a gain of function reporter.

The specific PMO-X modifications of the compounds described in this example were 0-1-0-730 (PMO): GCT ATT ACC TTA ACC CAC CAG (SEQ ID NO: 22) and NG-10-0245 (APN): GC$^{apn}$T A$^{apn}$T$^{apn}$T ACC T$^{apn}$TA ACC CAG (SEQ ID NO: 22). Neutrally charged PMO, or PMO modified with cationic backbone charges (APN), targeting the eGFP transgene was administered into the left lateral ventricle of EGFP-654 mice by a single intracebreroventricular (ICV) injection using a stereotaxic apparatus. Doses consisted of either 5 mg/kg (left panel, PMO or APN) for all mice or spanned a range of doses (right panel, 2.5 up to 40 mg/kg, APN only). Two weeks post-injection, mice were euthanized and the brain was removed and cut in half sagittally at the midline into left and right hemispheres. Each hemisphere was imaged on a Typhoon Trio (GE) by placing the cut surface face down on the flatbed platen. Scans were collected using a 488 nm laser to excite eGFP fluorescence. The resulting images were analyzed with ImageQuant software (GE) to quantify the fluorescence intensity of each hemisphere. The total detected fluorescence intensity within each hemisphere was divided by the number of pixels present in that hemisphere to yield an area-independent average fluorescence value for each half of the brain. Activity results for each surviving animal in a treatment group are expressed as points on the scatter plot. The mean fluorescence of the group is indicated by the horizontal line, +/−1 SD (left panel). The same experiment was performed with different doses of APN compound (right panel). A representative typhoon image from saline-, PMO-, and APN-treated eGFP-654 mice showing the localization of the EGFP signal demonstrates that ICV-injected oligomer activity is preferentially expressed within specific regions of the brain (bottom panel).

DETAILED DESCRIPTION

Definitions

As used herein, "nucleobase" (Nu), "base pairing moiety" or "base" are used interchangeably to refer to a purine or pyrimidine base found in native DNA or RNA (uracil, thymine, adenine, cytosine, and guanine), as well as analogs of the naturally occurring purines and pyrimidines, that confer improved properties, such as binding affinity to the oligonucleotide. Exemplary analogs include hypoxanthine (the base component of the nucleoside inosine); 5-methyl cytosine; C5-propynyl-modifed pyrimidines, 9-(aminoethoxy)phenoxazine (G-clamp) and the like.

Further examples of base pairing moieties include, but are not limited to, uracil, thymine, adenine, cytosine, and guanine having their respective amino groups protected by acyl protecting groups, 2-fluorouracil, 2-fluorocytosine, 5-bromouracil, 5-iodouracil, 2,6-diaminopurine, azacytosine, pyrimidine analogs such as pseudoisocytosine and pseudouracil and other modified nucleobases such as 8-substituted purines, xanthine, or hypoxanthine (the latter two being the natural degradation products). The modified nucleobases disclosed in Chiu and Rana, R N A, 2003, 9, 1034-1048, Limbach et al. Nucleic Acids Research, 1994, 22, 2183-2196 and Revankar and Rao, Comprehensive Natural Products Chemistry, vol. 7, 313, are also contemplated.

Further examples of base pairing moieties include, but are not limited to, expanded-size nucleobases in which one or more benzene rings has been added. Nucleic base replacements described in the Glen Research catalog (www.glen-research.com); Krueger A T et al, Acc. Chem. Res., 2007, 40, 141-150; Kool, E T, Acc. Chem. Res., 2002, 35, 936-943; Benner S. A., et al., Nat. Rev. Genet., 2005, 6, 553-543; Romesberg, F. E., et al., Curr. Opin. Chem. Biol., 2003, 7, 723-733; Hirao, I., Curr. Opin. Chem. Biol., 2006, 10, 622-627, are contemplated as useful for the synthesis of the oligomers described herein. Some examples of these expanded-size nucleobases are shown below:

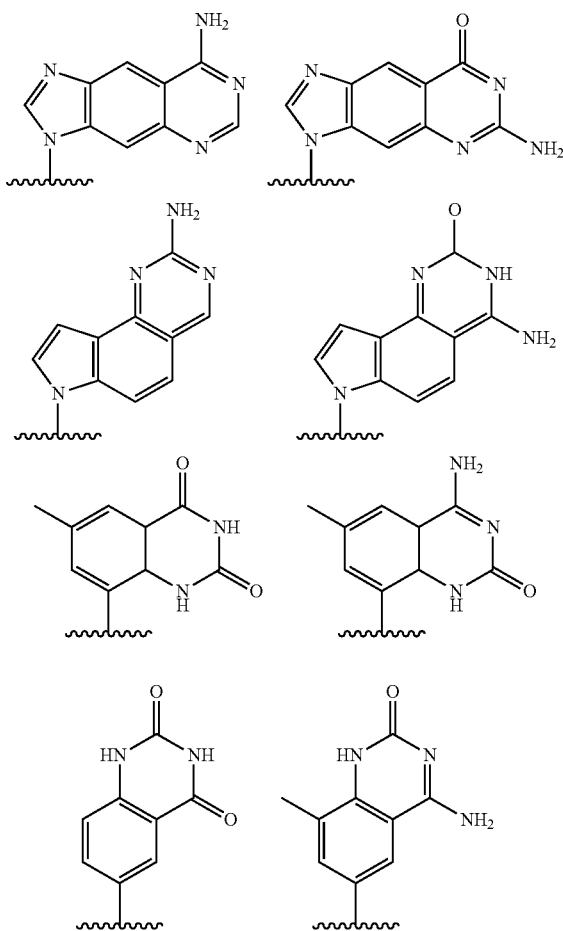
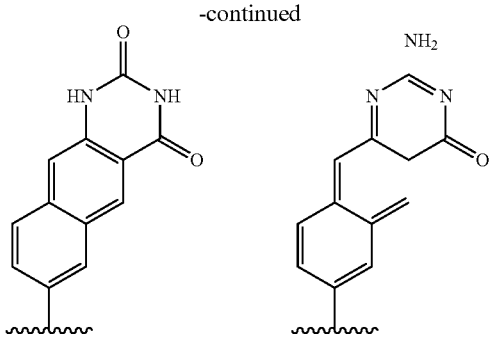

A nucleobase covalently linked to a ribose, sugar analog or morpholino comprises a nucleoside. "Nucleotides" are composed of a nucleoside together with one phosphate group. The phosphate groups covalently link adjacent nucleotides to one another to form an oligonucleotide. As used herein, an "oligonucleotide" is a linear sequence of nucleotides, or nucleotide analogs, that allows the nucleobase to hybridize to a target sequence in an RNA by Watson-Crick base pairing, to form an oligonucleotide:RNA heteroduplex within the target sequence. The terms "antisense oligonucleotide", "antisense oligomer", "oligomer" and "compound" may be used interchangeably to refer to an oligonucleotide.

A "morpholino oligomer" or "PMO" refers to an oligonucleotide having a backbone which supports a nucleobase capable of hydrogen bonding to typical polynucleotides, wherein the polymer lacks a pentose sugar backbone moiety, but instead contains a morpholino ring. Thus, in a PMO a morpholino ring structure supports a base pairing moiety, to form a sequence of base pairing moieties which is typically designed to hybridize to a selected antisense target in a cell or in a subject being treated. An exemplary "morpholino" oligomer comprises morpholino subunit structures linked together by phosphoramidate or phosphorodiamidate linkages, joining the morpholino nitrogen of one subunit to the 4' exocyclic carbon of an adjacent subunit, each subunit comprising a purine or pyrimidine nucleobase effective to bind, by base-specific hydrogen bonding, to a base in a polynucleotide. Morpholino oligomers (including antisense oligomers) are detailed, for example, in U.S. Pat. Nos. 5,698,685; 5,217,866; 5,142,047; 5,034,506; 5,166,315; 5,185,444; 5,521,063; 5,506,337 and pending U.S. patent application Ser. Nos. 12/271,036; 12/271,040; and PCT publication number WO/2009/064471 all of which are incorporated herein by reference in their entirety.

Within the oligonucleotide structure, the phosphate groups are commonly referred to as forming the "internucleoside linkages" of the oligonucleotide. The naturally occurring internucleoside linkage of RNA and DNA is a 3' to 5' phosphodiester linkage A "phosphoramidate" group comprises phosphorus having three attached oxygen atoms and one attached nitrogen atom, while a "phosphorodiamidate" group comprises phosphorus having two attached oxygen atoms and two attached nitrogen atoms. In the uncharged or the cationic intersubunit linkages of the PMO and/or PMOX oligomers described herein, one nitrogen is always pendant to the backbone chain. The second nitrogen, in a phosphorodiamidate linkage, is typically the ring nitrogen in a morpholino ring structure.

"PMOX" refers to phosporodiamidate morpholino oligomers having a phosphorus atom with (i) a covalent bond to the nitrogen atom of a morpholino ring and (ii) a second covalent bond to the ring nitrogen of a 4-aminopiperdin-1-yl (i.e. APN) or a derivative of 4-aminopiperdin-1-yl. PMOX oligomers are disclosed in PCT application No. PCT/US11/38459, herein incorporated by reference in its entirety. "PMOapn" or "APN" refers to a PMOX oligomer where a phosphorus atom is linked to a morpholino group and to the ring nitrogen of a 4-aminopiperdin-1-yl (i.e. APN).

As used herein, LNA refers to locked nucleic acid oligonucleotides. "LNA" are a member of a class of modifications called bridged nucleic acid (BNA). BNA is characterized by a covalent linkage that locks the conformation of the ribose ring in a C30-endo (northern) sugar pucker. For LNA, the bridge is composed of a methylene between the 2'-O and the 4'-C positions. LNA enhances backbone preorganization and base stacking to increase hybridization and thermal stability.

An oligonucleotide "specifically hybridizes" to a target polynucleotide if the oligomer hybridizes to the target under physiological conditions, with a Tm substantially greater than 45° C., preferably at least 50° C., and typically 60° C.-80° C. or higher. Such hybridization preferably corresponds to stringent hybridization conditions. At a given ionic strength and pH, the Tm is the temperature at which 50% of a target sequence hybridizes to a complementary polynucleotide. Such hybridization may occur with "near" or "substantial" complementarity of the antisense oligomer to the target sequence, as well as with exact complementarity.

A targeting sequence may have "near" or "substantial" complementarity to the target sequence and still function for the purpose of the present invention, that is, still be "complementary." Preferably, the oligonucleotide analog compounds employed in the present invention have at most one mismatch with the target sequence out of 10 nucleotides, and preferably at most one mismatch out of 20. Alternatively, the antisense oligomers employed have at least 90% sequence homology, and preferably at least 95% sequence homology, with the exemplary targeting sequences as designated herein.

"Expanded nucleotide repeat" or "repeat expansion" or "expanded polynucleotide repeat" refers to a mutation in which a normally polymorphic nucleotide repeat in a wild-type gene under goes a mutational change whereby the repeat has expanded in length by the insertion of simple nucleotide repeats. This dynamic mutation is unlike conventional mutations because the expanded repeat can undergo further change, usually continued expansion, with each subsequent generation.

As used herein, the term "mutant mRNA" is used interchangeably with "mutant polynucleotide repeat disease-causing mRNA" to refer to an mRNA that has a polynucleotide repeat disease-causing mutation.

As used herein, the term "wild-type mRNA" or "reference normal mRNA" refers to an mRNA that does not contain a polynucleotide repeat disease-causing mutation. In the context of Huntington's disease, the normal allele of the Huntington gene contains less than 36 CAG repeats. Accordingly, the reference normal mRNA refers to an HTT mRNA containing less than 36 CAG repeats. The number of polynucleotide repeats need not be identical across individuals with the same polynucleotide repeat disease, as there is variation in the number of repeats across individuals. For example, while one subject with Huntington's disease may have, e.g., 28 CAG repeats (SEQ ID NO: 38) for the normal HTT allele, and 80 CAG repeats (SEQ ID NO: 39) for the mutant HTT allele, another subject may have 13 CAG repeats (SEQ ID NO: 40) for the normal HTT allele and 60 repeats for the mutant HTT allele (SEQ ID NO: 46).

As used herein, the term "mutant allele" refers to an allele of a gene which is capable of causing a disease. The term "normal allele" refers to an allele of a gene which is not capable of causing a disease. In the context of Huntington's disease, a normal allele of the HTT gene contains less than 36 CAG repeats, whereas a "mutant allele" contains more than 36 CAG repeats.

"An electron pair" refers to a valence pair of electrons that are not bonded or shared with other atoms.

The terms "cell penetrating peptide" (CPP) or "a peptide moiety which enhances cellular uptake" are used interchangeably and refer to cationic cell penetrating peptides, also called "transport peptides", "carrier peptides", or "peptide transduction domains". The peptides have the capability of inducing cell penetration within 30%, 40%, 50%, 60%, 70%, 80%, 90% or 100% of cells of a given cell culture population and allow macromolecular translocation within multiple tissues in vivo upon systemic administration. In one embodiment, the cell-penetrating peptide is an arginine-rich peptide transporter. In another embodiment, the cell-penetrating peptide is Penetratin or the Tat peptide. These peptides are well known in the art and are disclosed, for example in US Publication No. 2010-0016215 A1, incorporated by reference in its entirety. A particularly preferred approach to conjugation of peptides to antisense oligonucleotides can be found in PCT publication WO2012/150960 which is incorporated by reference in its entirety. A preferred embodiment of a peptide conjugated oligonucleotide utilizes glycine as the linker between the CPP and the antisense oligonucleotide. For example, antisense oligonucleotides of the invention can be coupled to an arginine-rich peptide, such as $(Arg)_6Gly$ (SEQ ID NO: 36) (6 arginine and 1 glycine linked to an oligonucleotide). As an example, this peptide can be conjugated to a PMO and is known as "R6-G-PMO".

By "isolated" is meant material that is substantially or essentially free from components that normally accompany it in its native state. For example, an "isolated polynucleotide" or "isolated oligonucleotide," as used herein, may refer to a polynucleotide that has been purified or removed from the sequences that flank it in a naturally-occurring state, e.g., a DNA fragment that is removed from the sequences that are adjacent to the fragment in the genome. The term "isolating" as it relates to cells refers to the purification of cells (e.g., fibroblasts, lymphoblasts) from a source subject (e.g., a subject with a polynucleotide repeat disease). In the context of mRNA or protein, "isolating" refers to the recovery of mRNA or protein from a source, e.g., cells.

As used herein, "sufficient length" refers to an antisense oligonucleotide that is complementary to at least 8, more typically 8-30, contiguous nucleobases in an expanded repeat of the mutant RNA. An antisense oligonucleotide of sufficient length has at least a minimal number of nucleotides to be capable of specifically hybridizing to an expanded repeat in the mutant RNA. Preferably an oligonucleotide of sufficient length is from 10 to 40 nucleotides in length, including oligonucleotides of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and 40 nucleotides. In one embodiment, an oligonucleotide of sufficient length is from 10 to about 30 nucleotides in length. In another embodiment, an oligonucleotide of sufficient length is from 15 to about 25 nucleotides in length. In yet another embodiment, an oligonucleotide of sufficient length is from 20 to about 30 nucleotides in length. In one embodiment, the length of the antisense oligonucleotide for treating HD is 22 nucleotides.

As used herein, the terms "contacting a cell", "introducing" or "delivering" refers to delivery of the oligonucleotides of the invention into a cell by methods routine in the art, e.g., transfection (e.g., liposome, calcium-phosphate, polyethyleneimine), electroporation (e.g., nucleofection), microinjection.

As used herein, the term "quantifying", "quantification" or other related words refer to determining the quantity, mass, or concentration in a unit volume, of a nucleic acid, polynucleotide, oligonucleotide, peptide, polypeptide, or protein.

As used herein, "treatment" of a subject (e.g. a mammal, such as a human) or a cell is any type of intervention used in an attempt to alter the natural course of the individual or cell. Treatment includes, but is not limited to, administration of a pharmaceutical composition, and may be performed either prophylactically or subsequent to the initiation of a pathologic event or contact with an etiologic agent.

Structural Features of the Oligonucleotides

In some embodiments, the antisense oligonucleotide of the invention is uncharged. In other embodiments, the antisense oligonucleotide is charged.

In some embodiments, the antisense oligonucleotide may be a "morpholino oligomer," "PMO," "PMOX," "PPMO," or "PMO+". Furthermore, the antisense oligonucleotide, e.g., PMO, may be modified in any manner known in the art. One or more internucleotide linkages in the antisense oligonucleotide may be modified. For example, one or more internucleotide linkages in the antisense oligonucleotide may have a cationic modification. The cationic modification may be an APN modification. Preferably, the modified internucleotide linkages is derived from a T, C or A subunit. For example, in one embodiment, the PMO may comprise a cationic modification. The PMO may be an APN modified PMO, which may be referred to as a "PMOapn" or "APN."

A substantially uncharged oligonucleotide may be modified, in accordance with an aspect of the invention, to include charged linkages, e.g., up to about 1 per every 2-5 uncharged linkages, such as about 4-5 per every 10 uncharged linkages. In certain embodiments, optimal improvement in antisense activity may be seen when about 25% of the backbone linkages are cationic. In certain embodiments, enhancement may be seen with a small number e.g., 10-20% cationic linkages, or where the number of cationic linkages are in the range 50-80%, such as about 60%.

In certain embodiments, the antisense compounds can be prepared by stepwise solid-phase synthesis, employing methods detailed in the references cited above, and below with respect to the synthesis of oligonucleotides having a mixture or uncharged and cationic backbone linkages. In some cases, it may be desirable to add additional chemical moieties to the antisense compound, e.g., to enhance pharmacokinetics or to facilitate capture or detection of the compound. Such a moiety may be covalently attached, according to standard synthetic methods. For example, addition of a polyethyleneglycol moiety or other hydrophilic polymer, e.g., one having 1-100 monomeric subunits, may be useful in enhancing solubility.

A reporter moiety, such as fluorescein or a radiolabeled group, may be attached for purposes of detection. Alternatively, the reporter label attached to the oligomer may be a ligand, such as an antigen or biotin, capable of binding a labeled antibody or streptavidin. In selecting a moiety for attachment or modification of an antisense compound, it is generally of course desirable to select chemical compounds of groups that are biocompatible and likely to be tolerated by a subject without undesirable side effects.

In some embodiments, the antisense compounds can be constructed to contain a selected number of cationic linkages interspersed with uncharged linkages of the type described above. The intersubunit linkages, both uncharged and cationic, preferably are phosphorus-containing linkages, having the structure:

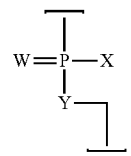

where
W is S or O, and is preferably O,
$X = R_1$, $NR^{11}R^{12}$ or $OR^{16}$,
$Y = O$ or $NR^{17}$,
and each said linkage in the oligomer is selected from:
(a) uncharged linkage (a), where each of $R^{11}$, $R^{12}$, $R^{16}$ and $R^{17}$ is independently selected from hydrogen and $C_1$-$C_6$ alkyl; or
(b1) cationic linkage (b1), where $R_1$ is a moiety of the formula

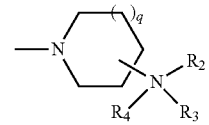

q is 0, 1, 2, 3 or 4;
$R_2$ is selected from the group consisting of hydrogen, $C_1$-$C_5$ alkyl, and a formamidinyl moiety, and
$R_3$ is selected from the group consisting of hydrogen and $C_1$-$C_5$ alkyl, or
$R_2$ and $R_3$ are joined to form a 5-7 membered heterocyclic ring optionally containing an oxygen heteroatom, where the ring may be optionally substituted with a substituent selected from the group consisting of $C_1$-$C_5$ alkyl, phenyl, halogen, and aralkyl;
$R_4$ is selected from the group consisting of null, hydrogen, $C_1$-$C_6$ alkyl and aralkyl;
(b2) cationic linkage (b2), where $X = NR^{11}R^{12}$ and $Y = O$, and $NR^{11}R^{12}$ represents an optionally substituted piperazino group of the formula

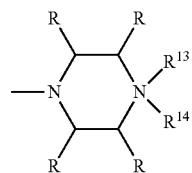

where
each R is independently H or $CH_3$,
$R^{14}$ is H, $CH_3$, or null, and $R^{13}$ is selected from H, $C_1$-$C_6$ alkyl, 5-7 membered substituted or unsubstituted aryl, heteroaryl or heterocylic ring containing up to 2 heteroatoms selected from the groups consisting of N and O, C(=NH)$NH_2$, Z-L-NRR, Z-L-NHC(=NH)$NH_2$, Z-L-COOH, Z-L-SH, Z-L-$PPh_3$, Z-L-$R^{21}$-$R^{22}$, cholate, and [C(O)CHR'NH]$_m$H, where: Z is C(O) or a direct bond, L is an optional linker up to 18 atoms in length, preferably up to 12 atoms, and more preferably up to 8 atoms in length, having bonds selected from alkyl, alkoxy, and alkylamino, R' is a side chain of a naturally occurring amino acid or a one- or two-carbon homolog thereof, m is 1 to 6, preferably 1 to 4; $R^{21}$ is a 5-7 membered aryl ring, and $R^{22}$ is a 5-7 membered heteroaryl ring containing up to 4 heteroatoms selected from the groups consisting of N and O;

(b3) cationic linkage (b3), where X=$NR^{11}R^{12}$ and Y=O, $R^{11}$=H or $CH_3$, and $R^{12}$=$LNR^{13}R^{14}R^{15}$, where L, $R^{13}$, and $R^{14}$ are as defined above, and $R^{15}$ is H, $C_1$-$C_6$ alkyl, or $C_1$-$C_6$ (alkoxy)alkyl; and (b4) cationic linkage (b4), where Y=$NR^{17}$ and X=$OR^{16}$, and $R^{17}$=$LNR^{13}R^{14}R^{15}$, where L, $R^{13}$, $R^{14}$ and $R^{15}$ are as defined above, and $R^{16}$ is H or $C_1$-$C_6$ alkyl;

and at least one said linkage is selected from cationic linkages (b1), (b2), (b3) and (b4).

In certain embodiments, an oligomer may include at least two consecutive linkages of type (a) (i.e. uncharged linkages). In further embodiments, at least 5% of the linkages in the oligomer are cationic linkages (i.e. type (b1), (b2), (b3) or (b4)); for example, 10% to 60%, and preferably 20-50% linkages may be cationic linkages.

In one embodiment, at least one linkage is of the type (hi), where, q is 1, $R_2$ and $R_3$ are hydrogen and $R_4$ is null.

In one embodiment, at least one linkage is of type (b2), where, preferably, each R is H, $R^{14}$ is H, $CH_3$, or null, and $R^{13}$ is selected from H, $C_1$-$C_6$ alkyl, C(=NH)$NH_2$, and C(O)-L-NHC(=NH)$NH_2$. The latter two embodiments of $R^{13}$ provide a guanidinyl moiety, either attached directly to the piperazine ring, or pendant to a linker group L, respectively. For ease of synthesis, the variable Z in $R^{13}$ is preferably C(O) (carbonyl), as shown.

The linker group L, as noted above, contains bonds in its backbone selected from alkyl (e.g., —$CH_2$—$CH_2$—), alkoxy (—C—O—), and alkylamino (e.g., —$CH_2$—NH—), with the proviso that the terminal atoms in L (e.g., those adjacent to carbonyl or nitrogen) are carbon atoms. Although branched linkages (e.g., —$CH_2$—$CHCH_3$—) are possible, the linker is preferably unbranched. In one embodiment, the linker is a hydrocarbon linker. Such a linker may have the structure —($CH_2$)$_n$—, where n is 1-12, preferably 2-8, and more preferably 2-6.

In some embodiments, the morpholino subunits (nucleotide) have the structure:

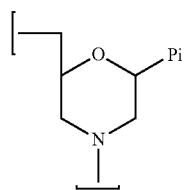

(i)

where Pi is a base-pairing moiety, and the linkages depicted above connect the nitrogen atom of (i) to the 5' carbon of an adjacent subunit. The base-pairing moieties Pi may be the same or different, and are generally designed to provide a sequence which binds to a target nucleic acid.

The use of embodiments of linkage types (b1), (b2) (b3) and (b4) above to link morpholino subunits may be illustrated graphically as follows:

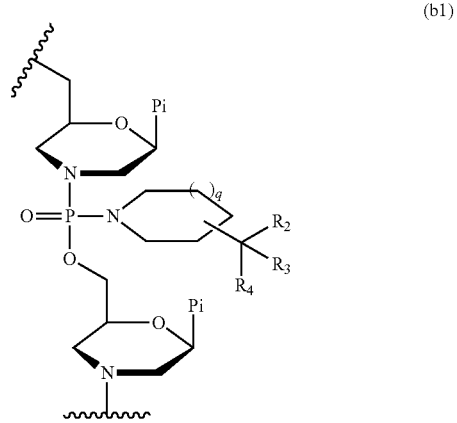

(b1)

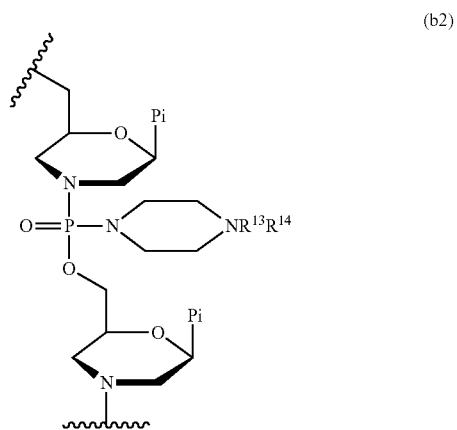

(b2)

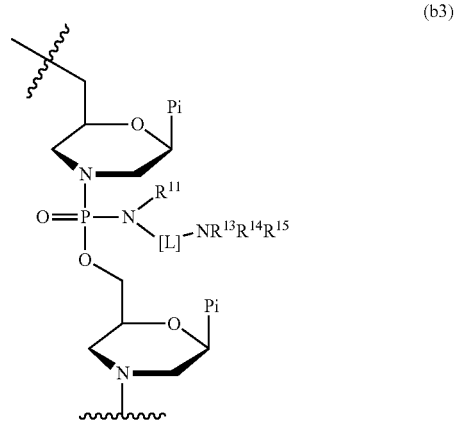

(b3)

-continued

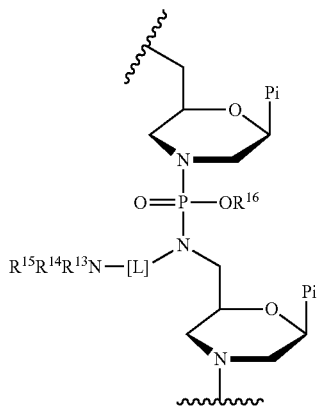

(B4)

Preferably, but not necessarily, all cationic linkages in the oligomer are of the same type; i.e. all of type (b1), all of type (b2), all of type (b3) or all of type (b4).

In further embodiments, the cationic linkages are selected from linkages (b2') and (b2") as shown below, where (b2') is referred to herein as a "Pip" linkage and (b2") is referred to herein as a "GuX" linkage:

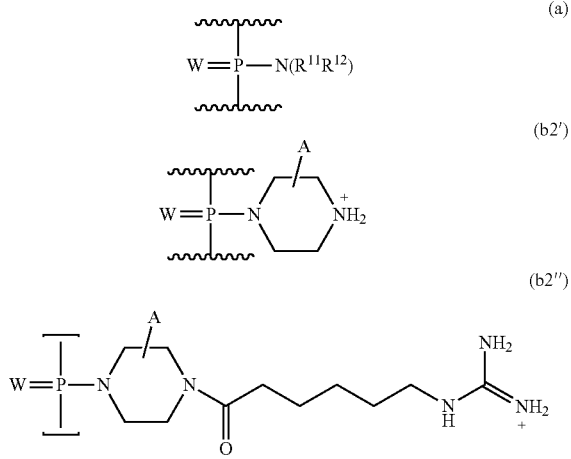

In the structures above, W is S or O, and is preferably O; each of $R^{11}$ and $R^{12}$ is independently selected from hydrogen and $C_1$-$C_6$ alkyl, and is preferably methyl or ethyl; and A represents hydrogen or $C_1$-$C_6$ alkyl on one or more carbon atoms in (b2') and (b2"). Preferably, the ring carbons in the piperazine ring are unsubstituted; however, they may include non-interfering substituents, such as methyl. Preferably, at most one or two carbon atoms is so substituted. In further embodiments, at least 10% of the linkages are of type (b2') or (b2"); for example, 10%-60% and preferably 20% to 50%, of the linkages may be of type (b2') or (b2").

In certain embodiments, the oligomer contains no linkages of the type (b2') above. Alternatively, the oligomer contains no linkages of type (b2) where each R is H, $R^{13}$ is H or $CH_3$, and $R^{14}$ is H, $CH_3$, or null.

The morpholino subunits may also be linked by non-phosphorus-based intersubunit linkages, as described further below, where at least one linkage is modified with a pendant cationic group as described above.

Other oligonucleotide analog linkages which are uncharged in their unmodified state but which could also bear a pendant amine substituent could be used. For example, a 5'-nitrogen atom on a morpholino ring could be employed in a sulfamide linkage or a urea linkage (where phosphorus is replaced with carbon or sulfur, respectively) and modified in a manner analogous to the 5'-nitrogen atom in structure (b4) above.

Oligomers having any number of cationic linkages are provided, including fully cationic-linked oligomers. Preferably, however, the oligomers are partially charged, having, for example, 10%-80%. In preferred embodiments, about 10% to 60%, and preferably 20% to 50% of the linkages are cationic.

In one embodiment, the cationic linkages are interspersed along the backbone. The partially charged oligomers preferably contain at least two consecutive uncharged linkages; that is, the oligomer preferably does not have a strictly alternating pattern along its entire length.

Also considered are oligomers having blocks of cationic linkages and blocks of uncharged linkages; for example, a central block of uncharged linkages may be flanked by blocks of cationic linkages, or vice versa. In one embodiment, the oligomer has approximately equal-length 5', 3' and center regions, and the percentage of cationic linkages in the center region is greater than about 50%, preferably greater than about 70%.

Oligomers for use in antisense applications generally range in length from about 10 to about 40 subunits, more preferably about 10 to 30 subunits, and typically 15-25 bases. For example, an oligomer of the invention having 19-20 subunits, a useful length for an antisense compound, may ideally have two to ten, e.g., four to eight, cationic linkages, and the remainder uncharged linkages. An oligomer having 14-15 subunits may ideally have two to seven, e.g., 3, 4, or 5, cationic linkages and the remainder uncharged linkages.

Each morpholino ring structure supports a base pairing moiety, to form a sequence of base pairing moieties which is typically designed to hybridize to a selected antisense target in a cell or in a subject being treated. The base pairing moiety may be a purine or pyrimidine found in native DNA or RNA (e.g., A, G, C, T or U) or an analog, such as hypoxanthine (the base component of the nucleoside inosine) or 5-methyl cytosine.

As noted above, certain embodiments are directed to oligomers comprising novel intersubunit linkages, including PMO-X oligomers and those having modified terminal groups. In some embodiments, these oligomers have higher affinity for DNA and RNA than do the corresponding unmodified oligomers and demonstrate improved cell delivery, potency, and/or tissue distribution properties compared to oligomers having other intersubunit linkages. In one embodiment, the oligomers comprise at least one intersubunit linkage of type (B) as defined herein. The oligomers may also comprise one or more intersubunit linkages of type (A) as defined herein. The structural features and properties of the various linkage types and oligomers are described in more detail in the following discussion. The synthesis of these and related oligomers is described in co-owned U.S. application Ser. No. 13/118,298, which is incorporated by reference in its entirety.

In certain embodiments, the invention provides for an oligonucleotide having a sequence complementary to the target sequence which is associated with a human disease, and comprises a sequence of nucleotides having a formula:

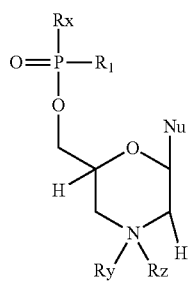

wherein Nu is a nucleobase;
$R_1$ is selected is a moiety of the formula

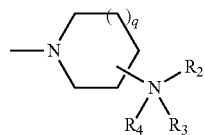

q is 0, 1, 2, 3 or 4;

$R_2$ is selected from the group consisting of hydrogen, $C_1$-$C_5$ alkyl, and a formamidinyl moiety, and $R_3$ is selected from the group consisting of hydrogen and $C_1$-$C_5$ alkyl, or $R_2$ and $R_3$ are joined to form a 5-7 membered heterocyclic ring optionally containing an oxygen hetero atom, where the ring may be optionally substituted with a substituent selected from the group consisting of $C_1$-$C_5$ alkyl, phenyl, halogen, and aralkyl;

$R_4$ is selected from the group consisting of null, hydrogen, a $C_1$-$C_6$ alkyl and aralkyl;

Rx is selected from the group consisting of HO—, a nucleotide, a cell penetrating peptide moiety, and piperazinyl;

Ry is selected from the group consisting of hydrogen, a $C_1$-$C_6$ alkyl, a nucleotide, a peptide moiety, an amino acid, a formamidinyl moiety, and acyl; and, Rz is selected from the group consisting of an null, hydrogen, a $C_1$-$C_6$ alkyl, and acyl; and pharmaceutically acceptable salts thereof.

Nu may be selected from the group consisting of adenine, guanine, thymine, uracil, cytosine, and hypoxanthine. More preferably Nu is thymine or uracil.

In some embodiments, about 50-90% of the $R_1$ groups are dimethylamino (i.e., $R_1'$). Preferably about 66% (two thirds) of the $R_1$ groups are dimethylamino.

$R_1$ may be selected from the group consisting of

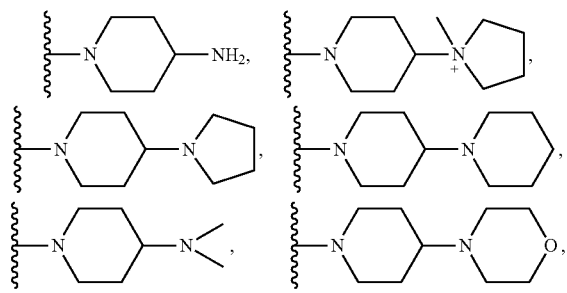

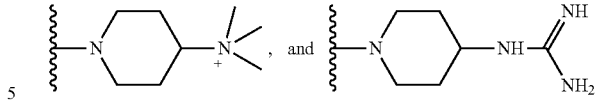

Preferably, at least one nucleotide of the oligonucleotide has the formula:

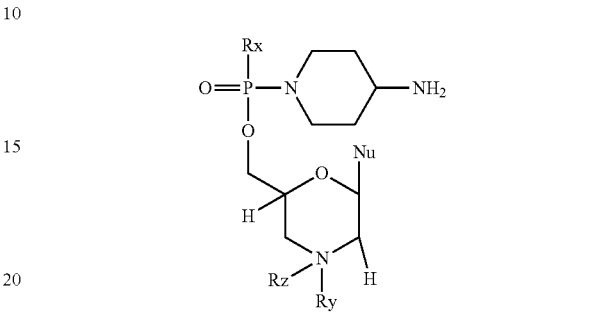

wherein Rx, Ry, Rz, and Nu are as stated above. Preferably, Nu is thymine or uracil.

Although thymine (T) is the preferred base pairing moiety (Nu or Pi) containing the chemical modifications described above, any base subunit known to a person of skill in the art can be used as the base pairing moiety.

Antisense Oligonucleotides

The invention provides for the use of an antisense oligonucleotide that comprises a sequence selected from the group consisting of (CCG)n (SEQ ID NO: 27), (CTG)n (SEQ ID NO: 28), (TTC)n (SEQ ID NO: 29), (NGC)n (SEQ ID NO: 30), (GNC)n (SEQ ID NO: 31), (CAGG)n (SEQ ID NO: 32), (AGAAT)n (SEQ ID NO: 33), and (CGCG$_4$CG$_4$)n (SEQ ID NO: 23), wherein N is any nucleotide and n is from about 3 to about 10. Preferably, the antisense oligonucleotide comprises a sequence selected from the group consisting of (GCT)n (SEQ ID NO: 45) and (G$_2$C$_4$)n (SEQ ID NO: 37). A preferred antisense oligonucleotide is (GCT)n (SEQ ID NO: 45). In this last aspect, n may be about 7. In one embodiment, the antisense oligonucleotide comprises a sequence (GCT)$_7$G (SEQ ID NO: 21). In other embodiments, the antisense oligonucleotide is (G$_2$C$_4$)n (SEQ ID NO: 37), with a preferred range for n of 3 to 10, more preferably 4.

Exemplary antisense oligonucleotide sequences of the invention that are suitable for treating various expanded repeat disorders are shown in Table 1.

Huntington's Disease

HD is a fatal, neurodegenerative disorder with no cure that is associated with cognitive decline, dementia, and loss of motor coordination. It is characterized by the progressive and heritable increase in length of CAG trinucleotide repeats that encode a polyglutamine tract, in the coding region of the Huntington (HTT) gene. These repeats can increase in number from one generation to another. The normal allele of the HTT gene contains less than 36 CAG repeats, whereas the mutant allele contains more than 36 repeats. Most HD patients carry one normal allele and a mutant disease-causing allele. Functionally, the aberrant accumulation of CAG repeats is thought to confer a toxic gain-of-function to the mutant HD protein, causing it to aggregate, form protein deposits (i.e., inclusion bodies), and induce cell death. Disease severity generally reflects the extent of expanded repeats in the mutant HTT protein.

In a preferred embodiment the oligomer structure of the PMOapn for treating HD is $$5'\ GC^{apn}T\ GC^{apn}T\ GC^{apn}T\ GC^{apn}T\ GC^{apn}T\ GC^{apn}T\ GC^{apn}T\ G\ 3'\ \text{(SEQ ID NO: 21)}$$

Any base (i.e., thymine, adenine, cytosine, and guanine) of the antisense oligonucleotides of the invention can be modified with a cationic linkage (e.g., an apn linkage). In the PMOapn shown above, the thymine (T) has an apn linkage between the cytosine, which is indicated by the superscript apn. Other linkages preferably have a dimethyl amino linked to the phosphorous atom. The above sequence is complementary to the expanded repeat in the Huntington's mutant RNA. The sequences of other exemplary antisense oligonucleotides for treating HD are shown below:

```
                                           (SEQ ID NO: 3)
AON#1:    5'-CTG CTG CTG CTG CTG CTG CTG-3'

(SEQ ID NO: 4)
AON#2:    5'-CTG CTG CTG CTG CTG CTG CTG CTG CTG-3'
```

These antisense oligonucleotide sequences can be modified by any of the cationic intersubunit linkages disclosed herein.

DM1/DM2

Myotonic dystrophy type 1 (DM1) and type 2 (DM2) are associated with long polyCUG and polyCCUG repeats in the 3'-UTR and intron 1 regions of the transcript dystrophia myotonica protein kinase (DMPK) and zinc finger protein 9 (ZNF9), respectively. While normal individuals have as many as 30 CTG repeats, DMI patients carry a larger number of repeats ranging from 50 to thousands. The severity of the disease and the age of onset correlates with the number of repeats. Patients with adult onsets show milder symptoms and have less than 100 repeats, juvenile onset DM1 patients carry as many as 500 repeats and congenital cases usually have around a thousand CTG repeats. The expanded transcripts containing CUG repeats form a secondary structure, accumulate in the nucleus in the form of nuclear foci and sequester RNA-binding proteins (RNA-BP).

Exemplary antisense oligonucleotides for treating DM1 are shown below:

```
                                           (SEQ ID NO: 9)
AON#1:    5'-CAG CAG CAG CAG CAG CAG CAG-3'

(SEQ ID NO: 10)
AON#2:    5'-CAG CAG CAG CAG CAG CAG CAG CAG CAG-3'
```

Exemplary antisense oligonucleotides for treating DM2 are shown below:

```
                                           (SEQ ID NO: 5)
AON#1:    5'-CAG GCA GGC AGG CAG GCA GG-3'

(SEQ ID NO: 6)
AON#2:    5'-CAG GCA GGC AGG CAG GCA GGC AGG CAG-3'
```

These antisense oligonucleotide sequences can be modified by any of the cationic intersubunit linkages disclosed herein.

ALS

Another disease characterized by an expanded nucleotide repeat in genomic DNA is amyotrophic lateral sclerosis (ALS). ALS is a fatal neurodegenerative disease characterized clinically by progressive paralysis leading to death from respiratory failure, typically within two to three years of symptom onset. ALS is the third most common neurodegenerative disease in the Western world, and there are currently no effective therapies. A proportion of ALS patients is characterized by a large hexanucleotide (GGGGCC) repeat expansion, for example, in the C9ORF72 gene (see, e.g., Renton et al., supra, and DeJesus-Hernandez et al., supra).

TABLE 1

| Disease | Expanded Repeat in RNA | AON | SEQ ID NO | Exemplary AON1 | SEQ ID NO | Exemplary AON2 |
|---|---|---|---|---|---|---|
| SPINOCEREBELLAR ATAXIA 10 | (ATTCT)n | (AGAAT)n | 1 | GAA TAG AAT AGA ATA GAA TAG | 2 | GAA TAG AAT AGA ATA GAA TAG AAT AG |
| DENTATORUBRAL-PALLIDOLUYSIAN ATROPHY | (CAG)n | (CTG)n | 3 | CTG CTG CTG CTG CTG CTG CTG | 4 | CTG CTG CTG CTG CTG CTG CTG CTG CTG |
| HUNTINGTON DISEASE | (CAG)n | (CTG)n | 3 | CTG CTG CTG CTG CTG CTG CTG | 4 | CTG CTG CTG CTG CTG CTG CTG CTG CTG |
| SPINAL AND BULBAR MUSCULAR ATROPHY, X-LINKED 1 | (CAG)n | (CTG)n | 3 | CTG CTG CTG CTG CTG CTG CTG | 4 | CTG CTG CTG CTG CTG CTG CTG CTG CTG |
| CHOREA, BENIGN HEREDITARY | (CAG)n | (CTG)n | 3 | CTG CTG CTG CTG CTG CTG CTG | 4 | CTG CTG CTG CTG CTG CTG CTG CTG CTG |
| SPINOCEREBELLAR ATAXIA 7 | (CAG)n | (CTG)n | 3 | CTG CTG CTG CTG CTG CTG CTG | 4 | CTG CTG CTG CTG CTG CTG CTG CTG CTG |
| SPINOCEREBELLAR ATAXIA 1 & 3 | (CAG)n | (CTG)n | 3 | CTG CTG CTG CTG CTG CTG CTG | 4 | CTG CTG CTG CTG CTG CTG CTG CTG CTG |

TABLE 1-continued

| Disease | Expanded Repeat in RNA | AON | SEQ ID NO | Exemplary AON1 | SEQ ID NO | Exemplary AON2 |
|---|---|---|---|---|---|---|
| SPINOCEREBELLAR ATAXIA 2 | (CAG)n | (CTG)n | 3 | CTG CTG CTG CTG CTG CTG CTG | 4 | CTG CTG CTG CTG CTG CTG CTG CTG |
| MACHADO JOSEPH DISEASE | (CAG)n | (CTG)n | 3 | CTG CTG CTG CTG CTG CTG CTG | 4 | CTG CTG CTG CTG CTG CTG CTG CTG |
| SPINOCEREBELLAR ATAXIA 6 | (CAG)n | (CTG)n | 3 | CTG CTG CTG CTG CTG CTG CTG | 4 | CTG CTG CTG CTG CTG CTG CTG CTG |
| SPINOCEREBELLAR ATAXIA 17 | (CAG)n | (CTG)n | 3 | CTG CTG CTG CTG CTG CTG CTG | 4 | CTG CTG CTG CTG CTG CTG CTG CTG |
| SPINOCEREBELLAR ATAXIA 8 | (CAG)n | (CTG)n | 3 | CTG CTG CTG CTG CTG CTG CTG | 4 | CTG CTG CTG CTG CTG CTG CTG CTG |
| CHOREOACANTHOCYTOSIS | (CAG)n | (CTG)n | 3 | CTG CTG CTG CTG CTG CTG CTG | 4 | CTG CTG CTG CTG CTG CTG CTG CTG |
| SPINOCEREBELLAR ATAXIA 12 | (CAG)n | (CTG)n | 3 | CTG CTG CTG CTG CTG CTG CTG | 4 | CTG CTG CTG CTG CTG CTG CTG CTG |
| HUNTINGTON DISEASE-LIKE 2 | (CAG)n | (CTG)n | 3 | CTG CTG CTG CTG CTG CTG CTG | 4 | CTG CTG CTG CTG CTG CTG CTG CTG |
| SPASTIC PARAPLEGIA 4, AUTOSOMAL DOMINANT | (CAG)n | (CTG)n | 3 | CTG CTG CTG CTG CTG CTG CTG | 4 | CTG CTG CTG CTG CTG CTG CTG CTG |
| DYSTROPHIA MYOTONICA 2 | (CCTG)n | (CAGG)n | 5 | CAG GCA GGC AGG CAG GCA GG | 6 | CAG GCA GGC AGG CAG GCA GGC AGG CAG |
| FRAGILE X MENTAL RETARDATION SYNDROME | (CGG)n | (CCG)n | 7 | CCG CCG CCG CCG CCG CCG CCG | 8 | CCG CCG CCG CCG CCG CCG CCG CCG |
| MENTAL RETARDATION, X-LINKED, ASSOCIATED WITH FRAGILE SITE FRAXE | (CGG)n | (CCG)n | 7 | CCG CCG CCG CCG CCG CCG CCG | 8 | CCG CCG CCG CCG CCG CCG CCG CCG |
| FRAGILE X TREMOR/ATAXIA SYNDROME | (CGG)n | (CCG)n | 7 | CCG CCG CCG CCG CCG CCG CCG | 8 | CCG CCG CCG CCG CCG CCG CCG CCG |
| PARTINGTON X-LINKED MENTAL RETARDATION SYNDROME | (CGG)n | (CCG)n | 7 | CCG CCG CCG CCG CCG CCG CCG | 8 | CCG CCG CCG CCG CCG CCG CCG CCG |
| DYSTROPHIA MYOTONICA 1 | (CTG)n | (CAG)n | 9 | CAG CAG CAG CAG CAG CAG CAG | 10 | CAG CAG CAG CAG CAG CAG CAG CAG |
| SPINOCEREBELLAR ATAXIA 8 | (CTG)n | (CAG)n | 9 | CAG CAG CAG CAG CAG CAG CAG | 10 | CAG CAG CAG CAG CAG CAG CAG CAG |
| FRIEDREICH ATAXIA 1 | (GAA)n | (TTC)n | 11 | TTC TTC TTC TTC TTC TTC TTC | 12 | TTC TTC TTC TTC TTC TTC TTC TTC |
| SPINOCEREBELLAR ATAXIA 36 | (GGCCTG)n | (CAGGCC)n | 13 | CAG GCC CAG GCC CAG GCC CAG GCC | 14 | CAG GCC CAG GCC CAG GCC CAG GCC CAG GCC |
| FRONTOTEMPORAL DEMENTIA AND/OR AMYOTROPHIC LATERAL SCLEROSIS | (GGGGCC)n | (G2C4)n | 15 | GGC CCC GGC CCC GGC CCC GGC CCC | 16 | GGC CCC GGC CCC GGC CCC GGC |
| SPINOCEREBELLAR ATAXIA 31 | (TGGAA)n | (TTCCA)n | 17 | CCA TTC CAT TCC ATT CCA TTC C | 18 | CCA TTC CAT TCC ATT CCA TTC CAT TCC |
| MYOCLONIC EPILEPSY OF UNVERRICHT AND LUNDBORG | (C4GC4GCG)r | (CGCG4CG4)n | 19 | CGC GGG GCG GGG CGC GGG GCG G | 20 | CGC GGG GCG GGG GCG GGG GCG GGG CGC GGG |

Table 1 discloses "(C$_4$GC$_4$GCG)n" and "(CGCG$_4$CG$_4$)n" as SEQ ID NOS 43 and 44, respectively.

In one embodiment, the antisense oligonucleotide for treating ALS associated with $(G_4C_2)_n$ repeats comprises the sequence $(G_2C_4)_{10}$ (SEQ ID NO: 24). Other exemplary antisense oligonucleotides for treating ALS are shown below:

```
                                            (SEQ ID NO: 15)
AON#1: 5'-GGC CCC GGC CCC GGC CCC GGC CCC-3'

(SEQ ID NO: 16)
AON#2: 5'-GGC CCC GGC CCC GGC CCC GGC GGC CCC GGC-3'
```

These antisense oligonucleotide sequences can be modified by any of the cationic intersubunit linkages disclosed herein.

Methods of the Invention

In one aspect, the invention provides for a method for selectively reducing the expression of a mutant mRNA or protein produced from a mutant nucleotide repeat containing allele associated with a nucleotide repeat disease relative to the corresponding wild-type mRNA or protein, comprising contacting a cell with an antisense oligonucleotide of sufficient length and complementarity to the expanded nucleotide repeat such that it specifically hybridizes to the mutant mRNA. In one embodiment, the oligonucleotide comprises a sequence (GCT)n, wherein n is from about 3 to about 10, and comprises at least one internucleoside linkage that is positively charged at physiological pH. Preferably, n is 7. More preferably, the antisense oligonucleotide comprises a sequence $(GCT)_7G$ (SEQ ID NO: 21).

Optionally, the antisense oligonucleotide may have internucleoside linkage with both a basic nitrogen and an alkyl, aryl, or aralkyl group. Preferably, the antisense oligonucleotide comprises a morpholino.

Moreover, the invention provides that the antisense oligonucleotide has at least one internucleoside linkage that is positively charged at physiological pH. The invention also provides that the antisense oligonucleotide has at least one internucleoside linkage that exhibits a pKa between 5.5 and 12.

While not being bound by theory, it is believed that the positively charged APN group or APN derivatives in the PMOX oligomer facilitates binding to the negatively charged phosphates in the expanded repeat of the mutant mRNA. Thus, the formation of a hetroduplex between mutant RNA and the PMOX oligomer may be held together by an ionic attractive force, as well as by the Watson-Crick base pairing.

The invention also relates to a method for determining the responsiveness of a subject with a polynucleotide repeat disease to treatment with oligonucleotide therapy comprising:
  i. isolating cells from the subject,
  ii. culturing the cells,
  iii. introducing an oligonucleotide into the cells,
  iv. isolating mRNA or protein from the cells,
  v. optionally reverse transcribing and amplifying the mRNA using gene specific primers to a polynucleotide repeat disease-causing transcript, wherein the gene specific primers flank both ends of the polynucleotide repeat,
  vi. quantifying the levels of a mutant polynucleotide repeat disease-causing mRNA or protein and a reference wild-type mRNA or protein, and
  vii. comparing levels of the mutant polynucleotide repeat disease-causing mRNA or protein with levels of the reference wild-type mRNA or protein, and
  viii. determining that the subject is responsive to oligonucleotide therapy if levels of the mutant polynucleotide repeat disease-causing mRNA or protein is lower than that of the reference wild-type mRNA or protein.

The cells are preferably selected from the group consisting of fibroblasts, lymphoblasts, and white blood cells.

The oligonucleotides of the present invention can be applied to assays for determining the responsiveness of any given subject with a polynucleotide repeat disease to the oligonucleotide therapy of the present invention. The assays of the present invention therefore are useful for determining whether a subject with a polynucleotide repeat disease is a candidate for oligonucleotide therapy.

To determine whether the oligonucleotide therapy of the present invention will be a viable option for subjects with a polynucleotide repeat disease, that is, whether a subject will be responsive to the oligonucleotide therapy, cells are isolated from subjects, followed by assaying for the ability of the oligonucleotides of the invention to decrease mRNA or protein expression of a target polynucleotide repeat disease-causing transcript or protein.

Cells to be isolated from patients with polynucleotide repeat diseases are not limited, and can be, e.g., lymphoblasts, white blood cells (WBCs), or fibroblasts. Methods of culturing, establishing, immortalizing, and passaging these cells are routine in the art and described in, e.g., Ausubel et al., Current Protocols in Molecular Biology, 2000; Chapter 28. Preferably, the cells are fibroblasts. WBCs and lymphoblasts can be readily obtained from blood samples of patients using art-recognized techniques disclosed in, e.g., US2011/0136151, which is herein incorporated by reference in its entirety. Moreover, cell lines can be established from these isolated cells by immortalization with a virus such as Epstein-Barr virus or SV40 T-antigen, as is routinely carried out in the art (e.g., Mali et al., Stem Cells 2008; 26:1998-2005; Also-Rallo et al., European J Human Genetics 2010; 19:1059-65). Preferably, the immortalizing agent is SV40 T-antigen. The culturing and passaging of isolated cells and the established cell lines are carried out using standard cell culture methods, such as those disclosed in, e.g., US2011/0136151 and Villegas et al., Current Protocols in Molecular Biology. 2005; 28.3.1-28.3.9.

The antisense oligonucleotides of the invention can be introduced into isolated cells or established cell lines using art-recognized methods, including, but not limited to, standard transfection methods (e.g., liposome-based, calcium phosphate), electroporation (e.g., nucleofection), and microinjection. Transfection agents, e.g., liposome-based agents, are commercially available as kits (e.g., Superfect from Qiagen; Lipofectamine 2000 from Invitrogen; Fugene from Roche), and methods for using these transfection agents will be in accordance with the manufacturer's recommended instructions. Kits for performing nucleofection (e.g., Nucleofector kit) are commercially available from, e.g., Lonza (Basel, Switzerland). Nucleofection is carried out in accordance with the manufacturer's recommended protocol.

Methods for isolating mRNA and/or protein from cells or established cell lines are routine in the art and are described in, e.g., Ausubel et al., Current Protocols in Molecular Biology, 2011; Chapters 4 and 10. Kits for isolating mRNA and protein are also commercially available (e.g., RNeasy Mini Kit from Qiagen; Illustra RNAspin 96 kit from GE; Total Protein Extraction Kit from Millipore).

Methods for generating cDNA are routine in the art, and involve reverse transcription of the isolated mRNA with reverse transcriptase enzyme. Reverse transcriptase-based cDNA synthesis kits are available from, e.g., Invitrogen (SuperScript III First-Strand Synthesis System) and Epicentre (MMLV High Performance Reverse Transcriptase cDNA 1st-strand synthesis kit). Kits that combine first strand cDNA synthesis with subsequent polymerase chain reaction (PCR) with gene specific primers are also commercially available from, e.g., Invitrogen (Superscript III One-Step RT-PCR System with Platinum Taq DNA Polymerase) and Qiagen (Qiagen OneStep RT-PCR kit).

Methods of quantifying mRNA are routine in the art. Some non-limiting examples include Northern blot analysis, in situ hybridization, and combined cDNA synthesis and PCR or quantitative PCR. In a preferred embodiment, mRNA is quantified by cDNA synthesis followed by PCR with gene specific primers that flank both ends of the polynucleotide repeat disease-causing repeat sequence (e.g., CAG in HTT for Huntington's disease). Methods of quantifying proteins are also routine in the art and include, for example, Western blot analysis and ELISA assays. These methods are described in e.g., Ausubel et al., Current Protocols in Molecular Biology, 2011; Chapters 4, 10, 15).

The levels of mutant allele and normal allele mRNA or PCR product amplified from cDNA generated from mRNA can be compared using various art-recognized methods. In one embodiment, the PCR products ("amplicon") can be quantified on an agarose gel by densitometry using, e.g., ImageJ software (NIH, Maryland, USA). In another embodiment, quantification is carried out using quantitative PCR (see, e.g., Fraga et al., Current Protocols Essential Laboratory Techniques 2008, 00:10.3.1-10.3.34).

The present disclosure also provides for formulation and delivery of the disclosed oligomer. Accordingly, in one embodiment the present disclosure is directed to a composition comprising an oligomer as disclosed herein and a pharmaceutically acceptable vehicle. Effective delivery of the antisense oligomer to the target nucleic acid is an important aspect of treatment. Routes of antisense oligomer delivery include, but are not limited to, various systemic routes, including oral and parenteral routes, e.g., intravenous, subcutaneous, intraperitoneal, and intramuscular, as well as inhalation, transdermal and topical delivery. The appropriate route may be determined by one of skill in the art, as appropriate to the condition of the subject under treatment. Vascular or extravascular circulation, the blood or lymph system, and the cerebrospinal fluid are some non-limiting sites where the RNA may be introduced.

The antisense oligonucleotides of the invention can be delivered to the nervous system of a subject by any art-recognized method. For example, peripheral blood injection of the antisense oligonucleotides of the invention can be used to deliver said reagents to peripheral neurons via diffusive and/or active means. Alternatively, the antisense oligonucleotides of the invention can be modified to promote crossing of the blood-brain-barrier (BBB) to achieve delivery of said reagents to neuronal cells of the central nervous system (CNS). Specific recent advancements in antisense oligonucleotide technology and delivery strategies have broadened the scope of antisense oligonucleotide usage for neuronal disorders (Forte, A., et al. 2005. Curr Drug Targets 6:21-29; Jaeger, L. B., and W. A. Banks. 2005. Methods Mol. Med. 106:237-251; Vinogradov, S. V., et al. 2004. Bioconjug. Chem. 5:50-60; the preceding are incorporated herein in their entirety by reference). For example, the antisense oligonucleotides of the invention can be generated as peptide nucleic acid (PNA) compounds. PNA reagents have each been identified to cross the BBB (Jaeger, L. B., and W. A. Banks. 2005. Methods Mol. Med. 106: 237-251). Treatment of a subject with, e.g., a vasoactive agent, has also been described to promote transport across the BBB (Id). Tethering of the antisense oligonucleotides of the invention to agents that are actively transported across the BBB may also be used as a delivery mechanism. In one embodiment, the antisense oligonucleotides of the invention are delivered intracerebroventricularly (icv).

In certain embodiments, the antisense oligonucleotides of the invention can be delivered by transdermal methods (e.g., via incorporation of the antisense oligonucleotides into, e.g., emulsions, with such antisense oligonucleotides optionally packaged into liposomes). Such transdermal and emulsion/liposome-mediated methods of delivery are described for delivery of antisense oligonucleotides in the art, e.g., in U.S. Pat. No. 6,965,025, the contents of which are incorporated in their entirety by reference herein.

The antisense oligonucleotides of the invention may also be delivered via an implantable device. Design of such a device is an art-recognized process, with, e.g., synthetic implant design described in, e.g., U.S. Pat. No. 6,969,400, the contents of which are incorporated in their entirety by reference herein.

Antisense oligonucleotides can be introduced into cells using art-recognized techniques (e.g., transfection, electroporation, fusion, liposomes, colloidal polymeric particles and viral and non-viral vectors as well as other means known in the art). The method of delivery selected will depend at least on the cells to be treated and the location of the cells and will be apparent to the skilled artisan. For instance, localization can be achieved by liposomes with specific markers on the surface to direct the liposome, direct injection into tissue containing target cells, specific receptor mediated uptake, viral vectors, or the like.

As known in the art, antisense oligonucleotides may be delivered using, e.g., methods involving liposome-mediated uptake, lipid conjugates, polylysine-mediated uptake, nanoparticle-mediated uptake, and receptor-mediated endocytosis, as well as additional non-endocytic modes of delivery, such as microinjection, permeabilization (e.g., streptolysin-O permeabilization, anionic peptide permeabilization), electroporation, and various non-invasive non-endocytic methods of delivery that are known in the art (refer to Dokka and Rojanasakul, Advanced Drug Delivery Reviews 44, 35-49, incorporated in its entirety herein by reference).

The antisense oligonucleotides may be administered in any convenient vehicle or carrier which is physiologically and/or pharmaceutically acceptable. Such a composition may include any of a variety of standard pharmaceutically acceptable carriers employed by those of ordinary skill in the art. Examples include, but are not limited to, saline, phosphate buffered saline (PBS), water, aqueous ethanol, emulsions, such as oil/water emulsions or triglyceride emulsions, tablets and capsules. The choice of suitable physiologically acceptable carrier will vary dependent upon the chosen mode of administration. "Pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The compounds (e.g., antisense oligonucleotides) of the present invention may generally be utilized as the free acid or free base. Alternatively, the compounds of this invention may be used in the form of acid or base addition salts. Acid addition salts of the free amino compounds of the present invention may be prepared by methods well known in the art, and may be formed from organic and inorganic acids. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids.

Suitable inorganic acids include hydrochloric, hydrobromic, sulfuric, phosphoric, and nitric acids. Base addition salts included those salts that form with the carboxylate anion and include salts formed with organic and inorganic cations such as those chosen from the alkali and alkaline earth metals (for example, lithium, sodium, potassium, magnesium, barium and calcium), as well as the ammonium ion and substituted derivatives thereof (for example, dibenzylammonium, benzylammonium, 2-hydroxyethylammonium, and the like). Thus, the term "pharmaceutically acceptable salt" is intended to encompass any and all acceptable salt forms.

In addition, prodrugs are also included within the context of this invention. Prodrugs are any covalently bonded carriers that release a compound in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol and amine functional groups of the antisense oligonucleotides of the invention. Further, in the case of a carboxylic acid (—COOH), esters may be employed, such as methyl esters, ethyl esters, and the like.

In some instances, liposomes may be employed to facilitate uptake of the antisense oligonucleotide into cells. (See, e.g., Williams, S. A., Leukemia 10(12):1980-1989, 1996; Lappalainen et al., Antiviral Res. 23:119, 1994; Uhlmann et al., antisense oligonucleotides: a new therapeutic principle, Chemical Reviews, Volume 90, No. 4, 25 pages 544-584, 1990; Gregoriadis, G., Chapter 14, Liposomes, Drug Carriers in Biology and Medicine, pp. 287-341, Academic Press, 1979). Hydrogels may also be used as vehicles for antisense oligomer administration, for example, as described in WO 93/01286. Alternatively, the oligonucleotides may be administered in microspheres or microparticles. (See, e.g., Wu, G. Y. and Wu, C. H., J. Biol. Chem. 262:4429-4432, 30 1987). Alternatively, the use of gas-filled microbubbles complexed with the antisense oligomers can enhance delivery to target tissues, as described in U.S. Pat. No. 6,245,747. Sustained release compositions may also be used. These may include semipermeable polymeric matrices in the form of shaped articles such as films or microcapsules.

In one embodiment, the antisense oligonucleotide is administered to a mammalian subject, e.g., human or domestic animal, exhibiting the symptoms of a polynucleotide repeat disorder, in a suitable pharmaceutical carrier. It is contemplated that the antisense oligonucleotide selectively reduces the expression of a mutant protein in the subject.

In one aspect of the method, the subject is a human subject, e.g., a patient diagnosed as having a polynucleotide repeat disease. The patient's condition may also dictate prophylactic administration of an antisense oligonucleotides of the invention, e.g., in the case of a patient who (1) is immunocompromised; (2) is a burn victim; (3) has an indwelling catheter; or (4) is about to undergo or has recently undergone surgery. In one preferred embodiment, the antisense oligonucleotide is contained in a pharmaceutically acceptable carrier, and is delivered orally. In another preferred embodiment, the oligomer is contained in a pharmaceutically acceptable carrier, and is delivered intravenously (i.v.).

In one embodiment, the antisense compound is administered in an amount and manner effective to result in a peak blood concentration of at least 200-400 nM antisense oligonucleotide. Typically, one or more doses of antisense oligomer are administered, generally at regular intervals, for a period of about one to two weeks.

Preferred doses for oral administration are from about 1-1000 mg oligonucleotide per 70 kg. In some cases, doses of greater than 1000 mg oligonucleotide/patient may be necessary. For i.v. administration, preferred doses are from about 0.5 mg to 1000 mg oligomer per 70 kg. The antisense oligonucleotide may be administered at regular intervals for a short time period, e.g., daily for two weeks or less; once every 2 days; once every 3 days; once every 3 to 7 days; once every 3 to 10 days; once every 7 to 10 days; once every two weeks; once monthly or every two, three, four, five or six months. However, in some cases the oligonucleotide is administered intermittently over a longer period of time e.g., for several weeks, months or years. Administration may be followed by, or concurrent with, administration of an antibiotic or other therapeutic treatment. The treatment regimen may be adjusted (dose, frequency, route, etc.) as indicated, based on the results of immunoassays, other biochemical tests and physiological examination of the subject under treatment.

An effective in vivo treatment regimen using the antisense oligonucleotides of the invention may vary according to the duration, dose, frequency and route of administration, as well as the condition of the subject under treatment (i.e., prophylactic administration versus administration in response to localized or systemic infection). Accordingly, such in vivo therapy will often require monitoring by tests appropriate to the particular type of disorder under treatment, and corresponding adjustments in the dose or treatment regimen, in order to achieve an optimal therapeutic outcome.

Treatment may be monitored, e.g., by general indicators of disease known in the art. The efficacy of an in vivo administered antisense oligonucleotide of the invention may be determined from biological samples (tissue, blood, urine etc.) taken from a subject prior to, during and subsequent to administration of the antisense oligonucleotide. Assays of such samples include (1) monitoring the presence or absence of heteroduplex formation with target and non-target sequences, using procedures known to those skilled in the art, e.g., an electrophoretic gel mobility assay; (2) monitoring the amount of a mutant mRNA or protein in relation to a reference wild-type mRNA or protein as determined by standard techniques such as RT-PCR, Northern blotting, ELISA or Western blotting.

In some embodiments, the antisense oligonucleotide is actively taken up by mammalian cells. In further embodiments, the antisense oligonucleotide may be conjugated to a transport moiety (e.g., transport peptide) as described herein to facilitate such uptake.

Methods of Treatment

The invention also relates to methods of reducing mRNA expression or protein expression using the antisense oligonucleotides of the present invention for therapeutic purposes (e.g., treating subjects with polynucleotide repeat disorders). Accordingly, in one embodiment, the present invention provides methods of treating an individual afflicted with a polynucleotide repeat disorder characterized by the aberrant expression of a mutant mRNA or protein containing a disease-associated polynucleotide repeat.

In one embodiment, cells from a subject having, e.g., HD, are contacted with an antisense oligonucleotide of the invention to reduce the expression of mRNA or protein produced from the mutant HTT allele. In other embodiments, cells from a subject having a different polynucleotide repeat disorder (e.g., one of those listed in Table 1) that would benefit from reduced expression of a protein produced from a mutant polynucleotide repeat containing allele are contacted with an antisense oligonucleotide of the invention. Target sequences and exemplary sequences of antisense oligonucleotides are also disclosed in Table 1.

The antisense oligonucleotides of the invention can be administered to subjects to treat (prophylactically or therapeutically) disorders associated with aberrant expression of a mRNA or protein produced from a mutant polynucleotide repeat containing allele. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a therapeutic agent as well as tailoring the dosage and/or therapeutic regimen of treatment with a therapeutic agent.

Comparison of Mutant HTT Transcript Expression in Response to Treatment with PMOapn, PMO, and LNA Oligonucleotides In performing the process of the invention, a side by side comparison of mRNA expression was made between PMOapn, PMO, and LNA oligonucleotides. The results are shown in FIGS. 6-10. The LNA, PMO, and APN oligomers contain the same sequence: 5' GCT GCT GCT GCT GCT GCT GCT G 3' (SEQ ID NO: 21). The LNA oligomers (ordered from Exiqon) contain a DNA backbone with an LNA modification at every T base (7 total modifications). The APN oligomers contain the PMO backbone with an apn modification at every T base (7 total modifications). The PMO oligomers contain the PMO backbone with no additional modifications to any intersubunit linkage.

Figure 6:
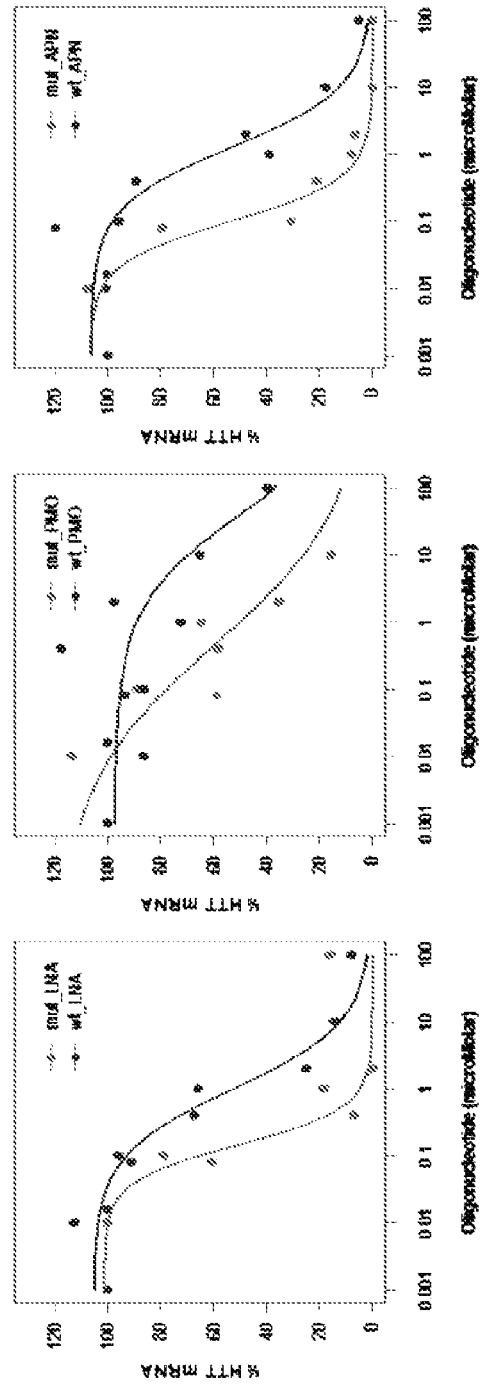
FIG. 6: Dose response curves from oligonucleotide-treated Huntington's Disease patient fibroblasts. LNA, PMO, and APN oligonucleotides contain same sequence: 5' GCT GCT GCT GCT GCT GCT GCT G 3' (SEQ ID NO: 21). The LNA oligonucleotide (ordered from Exiqon) contains a DNA backbone with an LNA modification at every thymine (T) base (7 total modifications). The APN oligonucleotide contains the PMO backbone with an apn modification at every T base (7 total modifications). The PMO oligonucleotide contains the PMO backbone with no additional modifications to the T base or any intersubunit linkage. Cells in panels A, B, and C, were nucleofected with the LNA, PMO, or APN oligonucleotide, respectively.

Cells were nucleofected with the LNA, PMO, or APN oligo, respectively. See Example 23. The RNA remaining 48 hours after the nucleotransfection process was quantified using reverse transcriptase PCR and the PCR products run on an acrylamide gel. The intensity of the gel band representing the wild-type or mutant HTT allele from GM04281 fibroblast cells (Coriell) was normalized to the intensity of the respective wild-type or mutant band of the lowest treated sample. The results are shown in FIG. 6. Each point on the graphs represents the mean of the normalized expression levels from two replicates at each concentration, and two independent experiments were combined to yield the dataset in FIG. 6. Gel intensity quantification was performed with ImageQuant (GE). Intensity normalization, EC50 calculation, and selectivity were analyzed with Microsoft Excel and R.

Mean EC50 values for each allele were calculated from the dataset presented in FIG. 6, as well as selectivity for the mutant allele was calculated from the EC50 of the wild-type and mutant alleles from fibroblasts nucleofected with the same oligo, using R and Graphpad Prism. A quantitative comparison of the results is shown in FIG. 7 and FIG. 9A. A comparison of the EC50 shows that cells treated with the PMO and APN oligos have reduced mRNA expression of the mutant allele relative to the wild-type allele compared to LNA. Moreover, the potency of the APN oligo, based on EC50 values, is improved over the PMO oligo.

The results show the unexpected reduction in levels of mutant mRNA believed to be responsible for Huntington's disease by the PMO, APN and LNA oligomers, and that the APN oligos was more selective at reducing the expression of mutant mRNA than either the PMO or LNA oligomers. One of skill in the art will appreciate that this method for reducing the expression of repeat disease mRNA can be applied to other repeat disease mRNAs, such as those that cause ALS and repeat diseases having expanded CAG trinucleotide repeats. In the antisense oligonucleotide n is preferably about 3 to about 10.

Comparison of Mutant HTT Protein Expression in Response to Treatment with PMOapn, PMO, and LNA Oligonucleotides The results above were extended to an analysis of mutant HTT protein expression, given that Huntington's disease, and many other expanded repeat diseases, ultimately manifest due to the toxic gain of function associated with the expression of a protein produced from a mutant polynucleotide repeat containing allele.

FIG. 11 shows a side-by-side comparison of the selectivity of PMOapn, PMO, and LNA oligonucleotides having the same sequences and modifications as described for FIGS. 6-10. GM-04281 cells were nucleofected as described for FIGS. 6-10. See Example 24. Protein lysates were prepared and subjected to Western blot analysis using anti-HTT or anti-β-actin primary antibody. The resulting blots were scanned on a Typhoon Trio (GE) and signal intensity of the mutant and normal HTT protein were quantified separately with ImageQuant (GE) software. Signal intensity of the normal (lower) and mutant (upper) HTT bands were normalized to the β-actin signal within each lane, and then each HTT band was normalized to the corresponding normal or mutant HTT band intensity from an untreated control sample on a separate blot. Protein expression results are plotted for each allele (normal, solid line; mutant, dashed line) as the mean percent of HTT protein expression, +/−1 SD. FIG. 12 shows the same data plotted as a ratio of wild-type to mutant HTT protein expression. As shown in FIGS. 11 and 12, relative to PMO- and LNA-modified oligonucleotides, APN-modified oligonucleotides showed high selectivity for reducing the expression of mutant HTT protein relative to wild-type HTT protein.

The results show the unexpected reduction in levels of mutant HTT protein by APN-, and to a lesser extent PMO-, but not LNA-modified oligonucleotides. One of skill in the art will appreciate that this method for reducing the expression of repeat disease protein can be applied to other repeat disease mRNAs, such as those that cause ALS and nucleotide repeat diseases having expanded CAG trinucleotide repeats. Table 1 lists other repeat diseases to which this technology can be applied, along with exemplary antisense oligonucleotides for each of the diseases.

Comparison of Mutant HTT Protein Expression in Response to Treatment with Antisense Oligonucleotides with APN- and Plus-Related Modifications The selectivity of antisense oligonucleotides with APN- (i.e., APN and map) and plus-related (i.e., plus, meda, and etpip) intersubunit linkages for reducing mutant HTT protein relative to wild-type HTT protein were tested.

PMO-$^{apn}$T:
(SEQ ID NO: 21)
GC$^{apn}$T GC$^{apn}$T GC$^{apn}$T GC$^{apn}$T GC$^{apn}$T GC$^{apn}$T GC$^{apn}$T G PMO-$^{map}$T:
(SEQ ID NO: 21)
GC$^{map}$TGC$^{map}$TGC$^{map}$TGC$^{map}$TGC$^{map}$TGC$^{map}$TGC$^{map}$TG -continued PMOplus:
(SEQ ID NO: 21)
GC + TGC + TGC + TGC + TGC + TGC + TGC + TG PMO-$^{meda}$T:
(SEQ ID NO: 21)
GC$^{meda}$TGC$^{meda}$TGC$^{meda}$TGC$^{meda}$TGC$^{meda}$TGC$^{meda}$TG PMO-$^{Etpip}$:
(SEQ ID NO: 21)
GC$^{Etpip}$TGC$^{Etpip}$TGC$^{Etpip}$TGC$^{Etpip}$TGC$^{Etpip}$TGC$^{Etpip}$ TGC$^{Etpip}$TG Exemplary structures for APN- and plus-related cationic modifications are shown in FIG. 13. GM-04281 cells were nucleofected as described for FIGS. 6-10 and protein samples were analyzed as described for FIGS. 11 and 12. See Example 25.

The results show that oligonucleotides having APN- or plus-related intersubunit linkages showed unexpectedly high selectivity in reducing the expression of mutant HTT protein relative to wild-type HTT protein. In particular, of the compounds tested, APN- and etpipT-modified oligonucleotides showed the highest selectivity for mutant HTT protein (FIGS. 14 and 15). One of skill in the art will appreciate that alternative cationic modifications (e.g., plus-related intersubunit linkages) can be incorporated into antisense oligonucleotides of the invention to reduce the expression of mutant proteins associated with nucleotide repeat diseases, such as ALS and repeat diseases having expanded CAG trinucleotide repeats. Table 1 lists other repeat diseases to which this technology can be applied, along with exemplary antisense oligonucleotides for each of the diseases.

The Preparation of PMO-X with Basic Nitrogen Internucleoside Linkers

Morpholino subunits, the modified intersubunit linkages and oligomers comprising the same can be prepared as described in the examples and in U.S. Pat. Nos. 5,185,444, and 7,943,762 which are hereby incorporated by reference in their entirety. The morpholino subunits can be prepared according to the following general Reaction Scheme I.

Reaction Scheme 1. Preparation of Morpholino Subunit

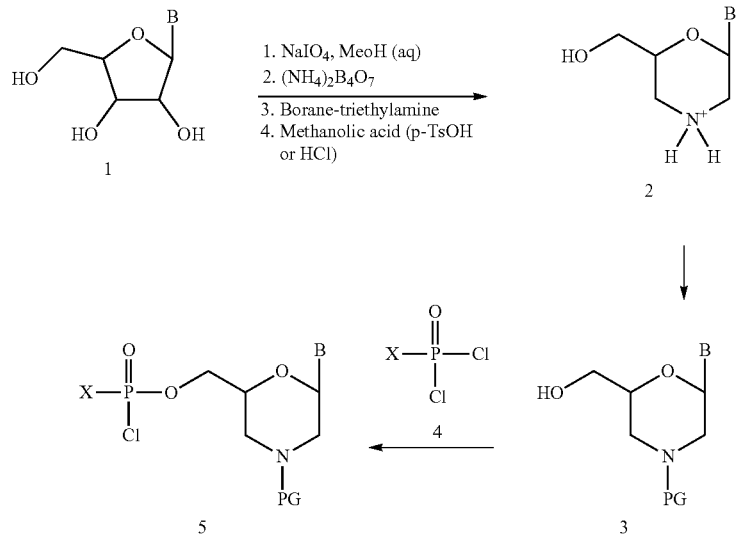

Referring to Reaction Scheme 1, wherein B represents a base pairing moiety and PG represents a protecting group, the morpholino subunits may be prepared from the corresponding ribonucleoside (1) as shown. The morpholino subunit (2) may be optionally protected by reaction with a suitable protecting group precursor, for example trityl chloride. The 3' protecting group is generally removed during solid-state oligomer synthesis as described in more detail below. The base pairing moiety may be suitable protected for sold phase oligomer synthesis. Suitable protecting groups include benzoyl for adenine and cytosine, phenylacetyl for guanine, and pivaloyloxymethyl for hypoxanthine (I). The pivaloyloxymethyl group can be introduced onto the N1 position of the hypoxanthine heterocyclic base. Although an unprotected hypoxanthine subunit, may be employed, yields in activation reactions are far superior when the base is protected. Other suitable protecting groups include those disclosed in co-pending U.S. application Ser. No. 12/271,040, which is hereby incorporated by reference in its entirety.

Reaction of 3 with the activated phosphorous compound 4, results in morpholino subunints having the desired linkage moiety 5. Compounds of structure 4 can be prepared using any number of methods known to those of skill in the art. For example, such compounds may be prepared by reaction of the corresponding amine and phosphorous oxychloride. In this regard, the amine starting material can be prepared using any method known in the art, for example those methods described in the Examples and in U.S. Pat. No. 7,943,762.

Figure 1:
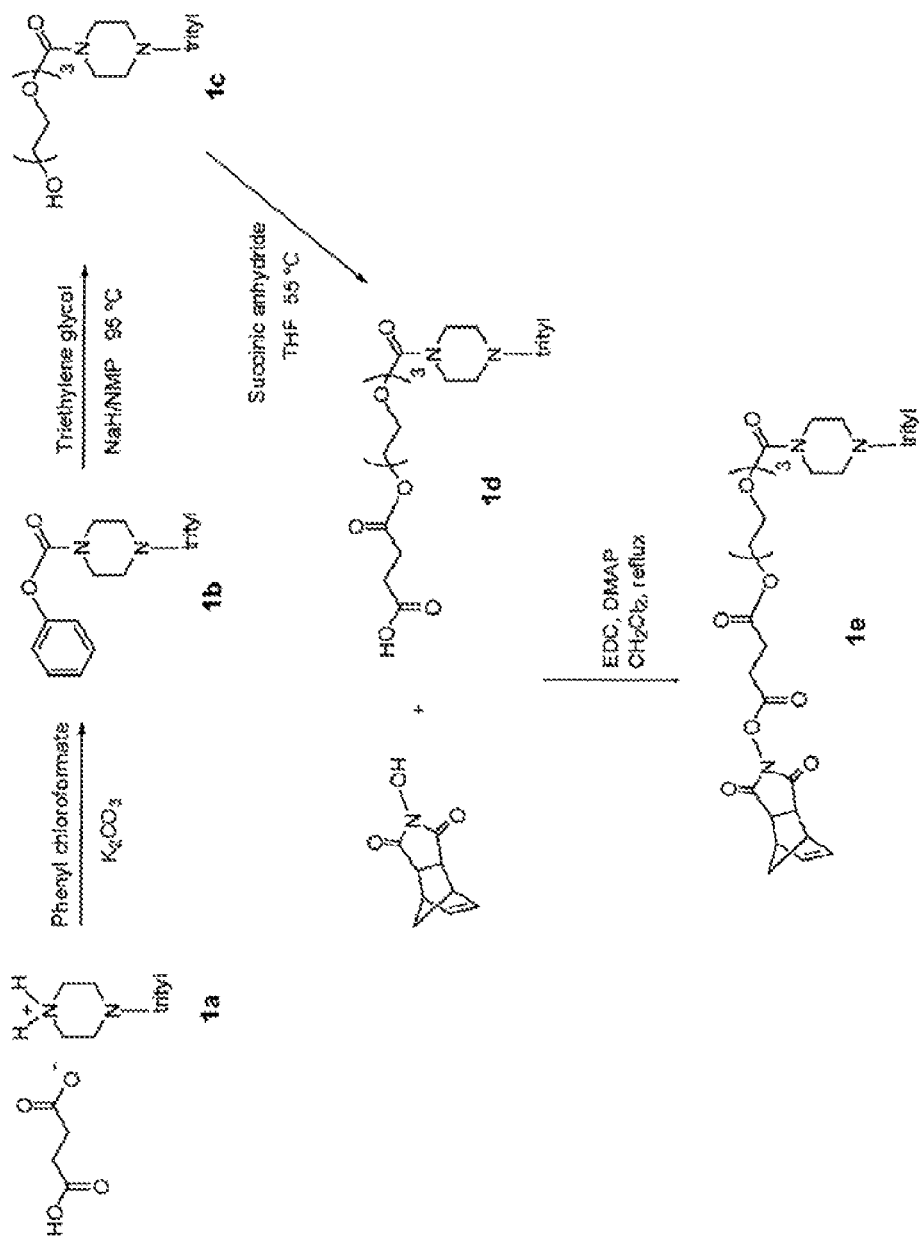
FIGS. 1 and 2: Preparation of the solid support for synthesis of morpholino oligomers.
Figure 2:
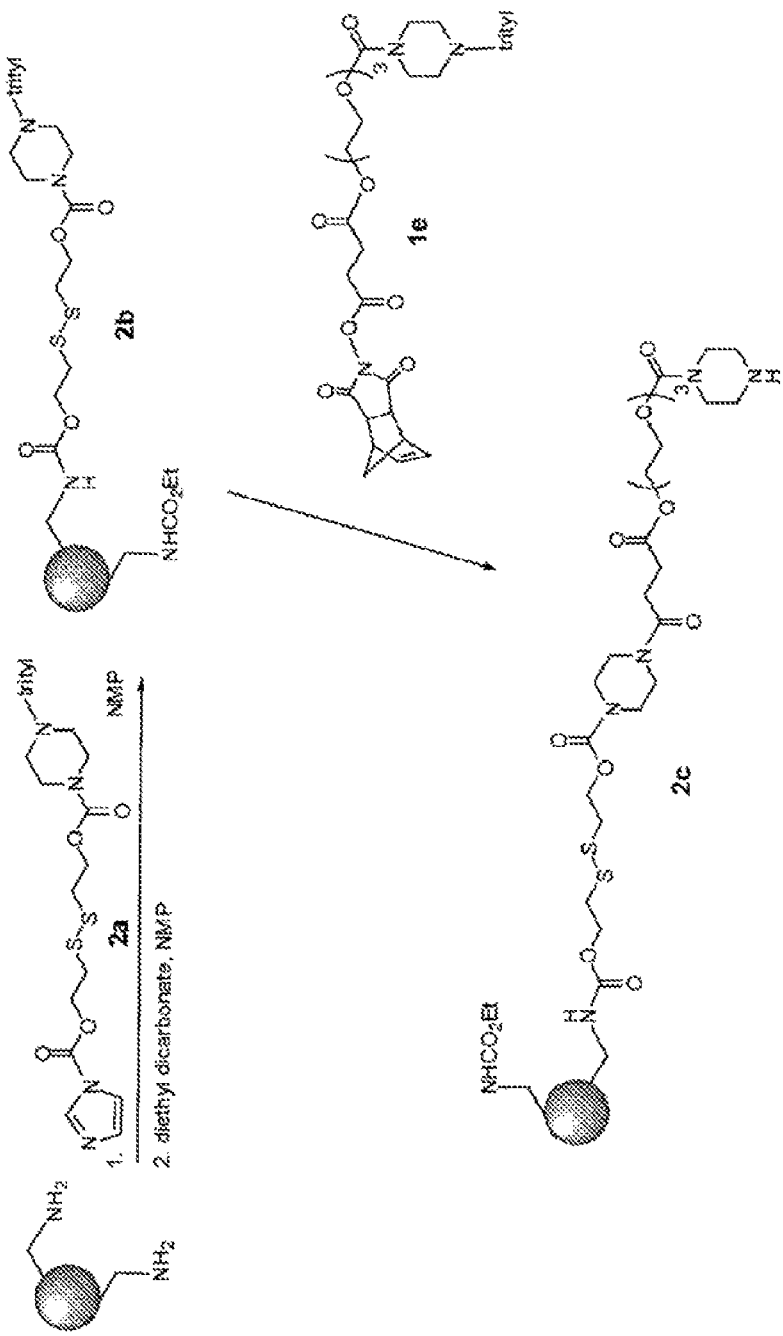
Figure 3:
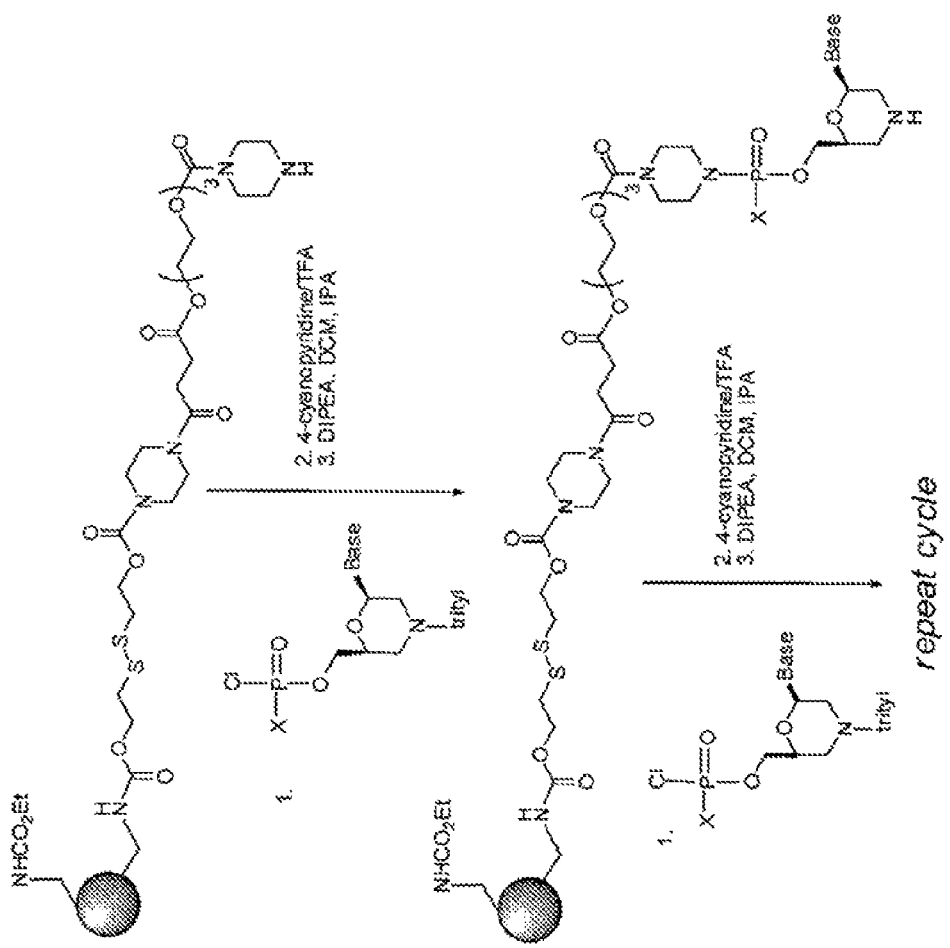
FIGS. 3 and 4: The solid phase synthesis of morpholino oligomers.
Figure 4:
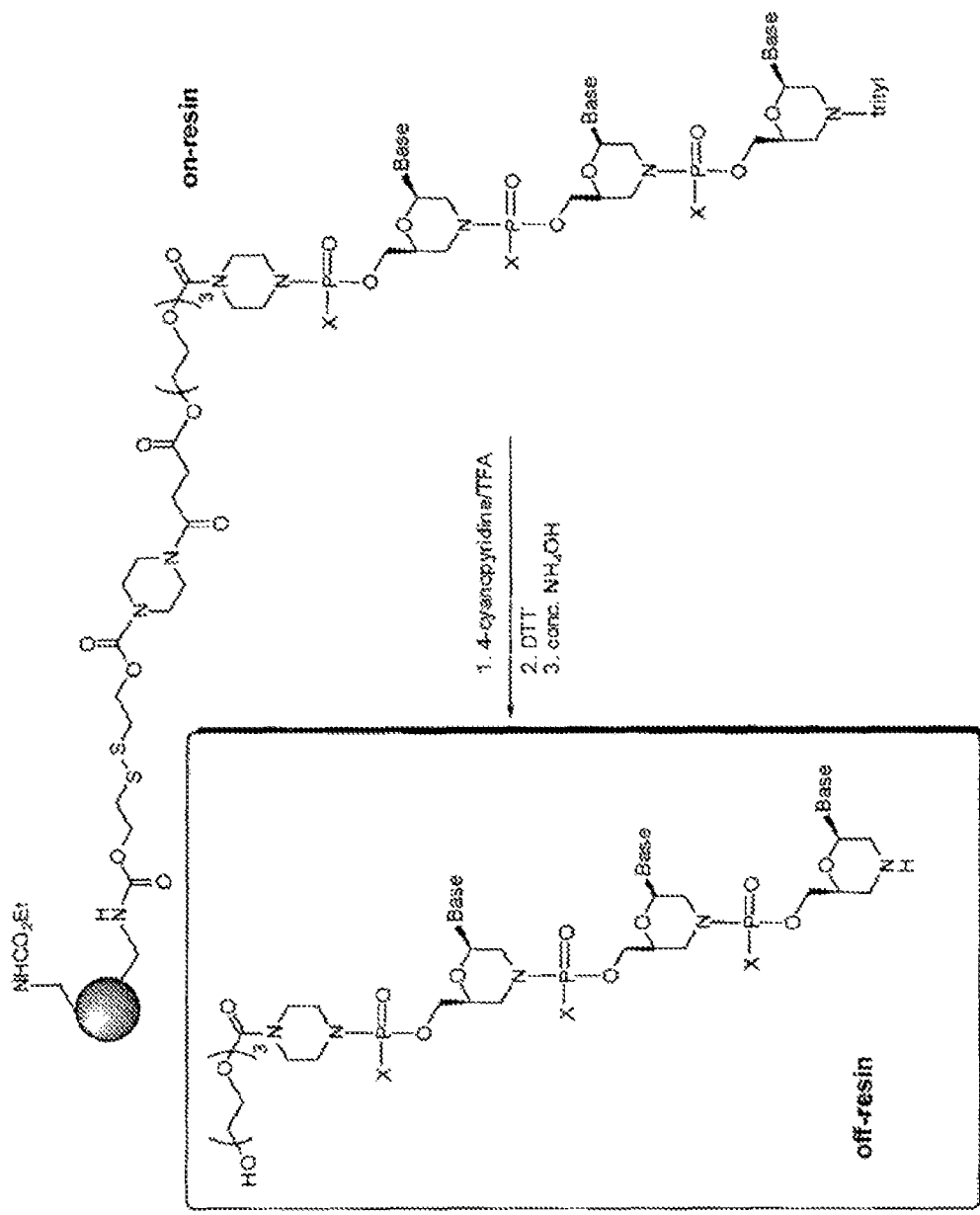
Figure 5:
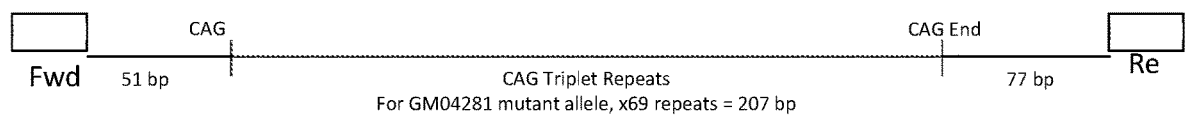
FIG. 5: Schematic representation of the amplicon from HTT alleles. This diagram is based on the NCBI Gene record (accession #NM_002111.6) with the length of the NCBI CAG triplet repeat expansion swapped for the expansion of the mutant allele in the GM04281 fibroblast line (SEQ ID NO: 42).

Compounds of structure 5 can be used in solid-phase automated oligomer synthesis for preparation of oligomers comprising the intersubunit linkages. Such methods are well known in the art. Briefly, a compound of structure 5 may be modified at the 5' end to contain a linker to a solid support. For example, compound 5 may be linked to a solid support by a linker comprising $L^{11}$ and $L^{15}$. An exemplary method is demonstrated in FIGS. 1 and 2. Once supported, the protecting group (e.g., trityl) is removed and the free amine is reacted with an activated phosphorous moiety of a second compound of structure 5. This sequence is repeated until the desired length of oligo is obtained. The protecting group in the terminal 5' end may either be removed or left on if a 5'-modification is desired. The oligo can be removed from the solid support using any number of methods, for example treatment with DTT followed by ammonium hydroxide as depicted in FIGS. 3 and 4.

The preparation of modified morpholino subunits and morpholino oligomers are described in more detail in the Examples. The morpholino oligomers containing any number of modified linkages may be prepared using methods described herein, methods known in the art and/or described by reference herein. Also described in the examples are global modifications of morpholino oligomers prepared as previously described (see e.g., PCT publication WO2008036127).

The term "protecting group" refers to chemical moieties that block some or all reactive moieties of a compound and prevent such moieties from participating in chemical reactions until the protective group is removed, for example, those moieties listed and described in T. W. Greene, P. G. M. Wuts, Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid moieties may be blocked with base labile groups such as, without limitation, methyl, or ethyl, and hydroxy reactive moieties may be blocked with base labile groups such as acetyl in the presence of amines blocked with acid labile groups such as tert-butyl carbamate or with carbamates that are both acid and base stable but hydrolytically removable.

Carboxylic acid and hydroxyl reactive moieties may also be blocked with hydrolytically removable protective groups such as the benzyl group, while amine groups may be blocked with base labile groups such as Fmoc. A particularly useful amine protecting group for the synthesis of compounds of Formula (I) is the trifluoroacetamide. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(0)-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups are known in the art and include, but are not limited to the following moieties:

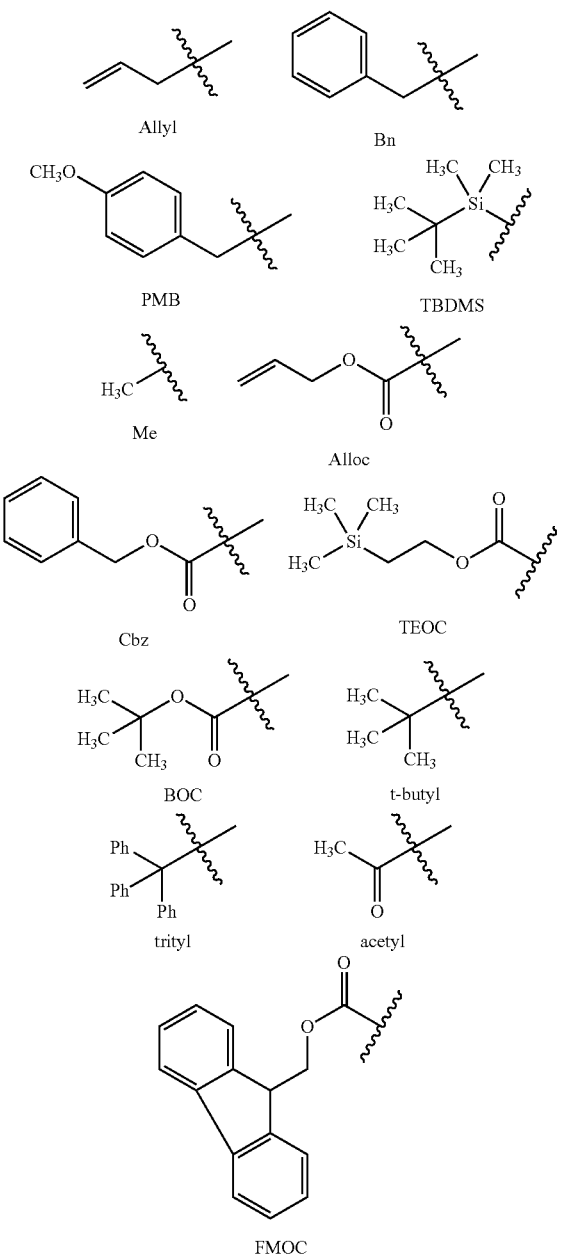

Unless otherwise noted, all chemicals were obtained from Sigma-Aldrich-Fluka. Benzoyl adenosine, benzoyl cytidine, and phenylacetyl guanosine were obtained from Carbosynth Limited, UK.

Synthesis of PMO, PMO+, PPMO, and PMO-X containing further linkage modifications as described herein was done using methods known in the art and described in pending U.S. application Ser. Nos. 12/271,036 and 12/271,040 and PCT publication number WO/2009/064471, which are hereby incorporated by reference in their entirety.

PMO with a 3' trityl modification are synthesized essentially as described in PCT publication number WO/2009/064471 with the exception that the detritylation step is omitted.

Procedure A for the Preparation of Activated Subunits:

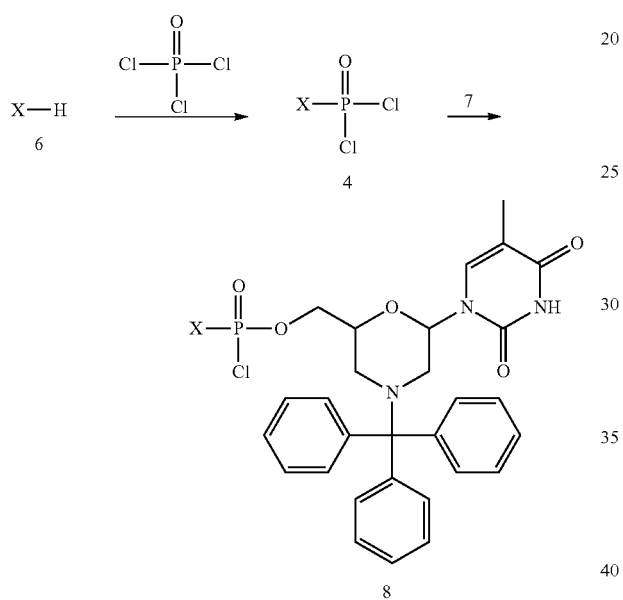

To a stirred solution of 6 (1 eq) in dichloromethane was added POCl$_3$ (1.1 eq), followed by diisopropylethylamine (3 eq) at 0° C., cooled by an ice-bath. After 15 minutes, the ice-bath was removed and the solution was allowed to warm to room temperature for one hour. Upon reaction completion, the reaction solution was diluted with dichloromethane, washed with 10% aqueous citric acid three times. After drying over MgSO$_4$, the organic layer was passed through a plug of silica gel and concentrated in vacuo. The resulting phosphoroamidodichloride (4) was used directly for the next step without further purification.

To a solution of the phosphoroamidodichloride (4) (1 eq), 2,6-lutidine (1 eq) in dichloromethane was added Mo(Tr)T (7) (0.5 eq)/dichloromethane solution, followed by N-methylimidazole (0.2 eq). The reaction stirred at room temperature overnight. Upon reaction completion, the reaction solution was diluted with dichloromethane, and washed with 10% aqueous citric acid three times. After drying over MgSO$_4$, the organic layer was filtered, then concentrated. The product (8) was purified by silica gel chromatography (eluting with a gradient of ethyl acetate/hexanes), and then stored at −20° C. The structure was confirmed by LCMS analysis.

Procedure B for the Preparation of Activated Subunits:

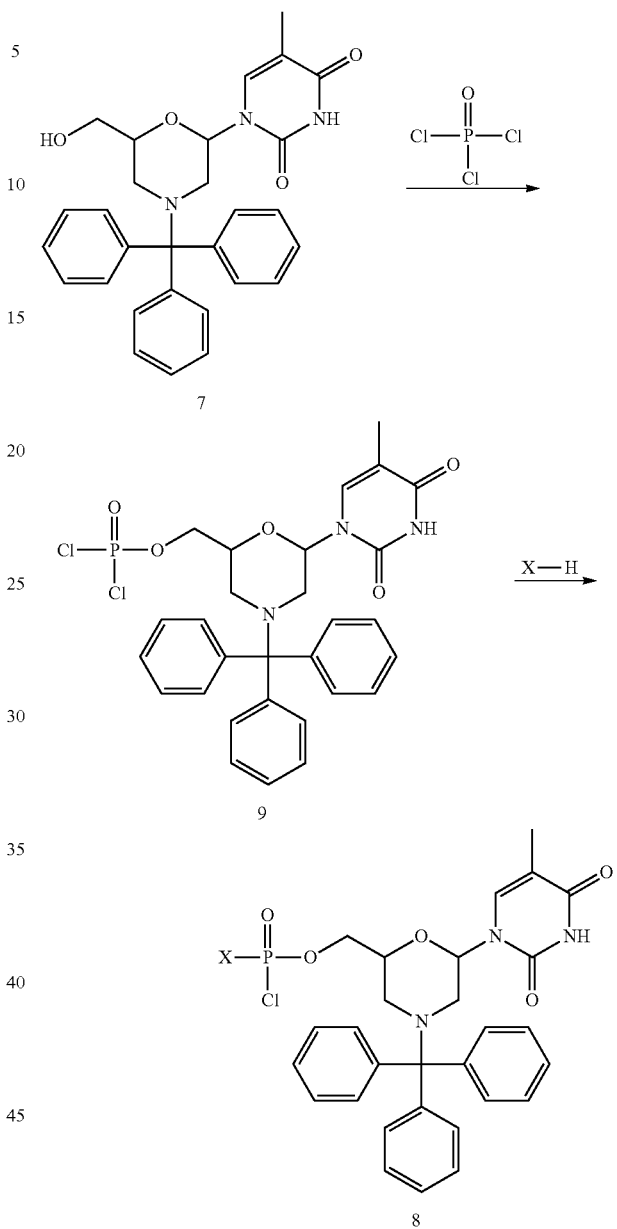

To a solution of POCl$_3$ (1.1 eq) in dichloromethane was added 2,6-lutidine (2 eq), followed by dropwise addition of Mo(Tr)T (7) (1 eq)/dichloromethane solution at 0° C. After 1 hour, the reaction solution was diluted with dichloromethane, and quickly washed three times with 10% aqueous citric acid. The desired phosphodichloridate (9) was obtained after drying over MgSO$_4$ and evaporation of solvent.

To a solution of the phosphodichloridate (1 eq) in dichloromethane was added amine (1 eq)/dichloromethane dropwise to the solution at 0° C. After 15 minutes, the reaction mixture was allowed to warm to room temperature for about an hour. Upon reaction completion, the product (8) as a white solid was collected by precipitation with the addition of hexanes, followed by filtration. The product was stored at −20° C. after drying under vacuum. The structure was confirmed by LCMS analysis.

Example 1: ((2S,6R)-6-(5-methyl-2,4-dioxo-3,4-dihydropyrimidin-1(2H)-yl)-4-tritylmorpholin-2-yl)methyl phosphorodichloridate

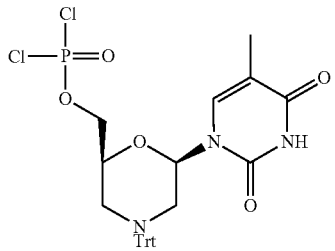

To a cooled (ice/water bath) DCM solution (20 mL) of phosphorus oxychloride (2.12 mL, 22.7 mmol) was added dropwise 2,6-lutidine (4.82 mL, 41.4 mmol) then a DCM solution (20 mL) Mo(Tr)T (2) (10.0 g, 20.7 mmol) was added dropwise over 15 min (int. temp. 0-10° C.) then bath was removed a stirring continued at ambient temperature for 20 min. The reaction was washed with citric acid solution (40 mL×3, 10% w/v aq), dried (MgSO$_4$), filtered and concentrated to a white foam (9.79 g) then used directly for the following procedure.

Example 2: (6-(5-methyl-2,4-dioxo-3,4-dihydropyrimidin-1(2H)-yl)-4-tritylmorpholin-2-yl)methyl (4-(dimethylamino)piperidin-1-yl)phosphonochloridate

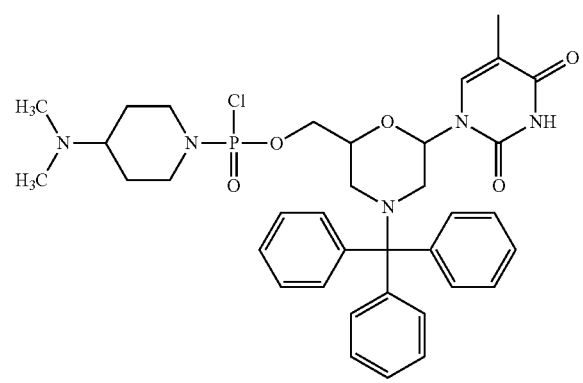 [SMILES: Cc1cn(C2CN(C(c3ccccc3)(c3ccccc3)c3ccccc3)CC(COP(=O)(Cl)N3CCC(N(C)C)CC3)O2)c(=O)[nH]c1=O]

To a cooled (ice/water bath) DCM solution (5 mL) of the dichlorophosphate from example 1 (5.00 g, 5.00 mmol) was added a DCM solution (5 mL) of the piperidine (0.61 g, 4.76 mmol) dropwise then the bath was removed and stirring continued at ambient temperature for 30 min. The reaction was loaded directly onto column. Chromatography [SiO$_2$ column (40 g), DCM/EtOH eluant (gradient 1:0 to 1:1)] to afford the title compound (2.5 g) as a white foam. ESI/MS calcd. for 1-(4-nitrophenyl)piperazine derivative $C_{46}H_{55}N_8O_7P$ 862.4, found m/z=863.6 (M+1).

Example 3: 1-(1-(chloro((6-(5-methyl-2,4-dioxo-3,4-dihydropyrimidin-1(2H)-yl)-4-tritylmorpholin-2-yl)methoxy)phosphoryl)piperidin-4-yl)-1-methylpyrrolidin-1-ium chloride

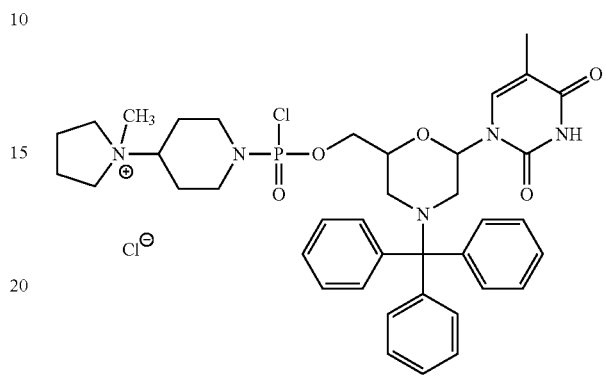

The title compound was synthesized in a manner analogous to that described in Example 2 to afford the title compound (0.6 g) as a white solid. ESI/MS calcd. for 1-(4-nitrophenyl)piperazine derivative $C_{49}H_{60}N_8O_7P$ 903.4, found m/z=903.7 (M+).

Example 4: ((2S,6R)-6-(5-methyl-2,4-dioxo-3,4-dihydropyrimidin-1(2H)-yl)-4-tritylmorpholin-2-yl)methyl (4-methylpiperazin-1-yl)phosphonochloridate

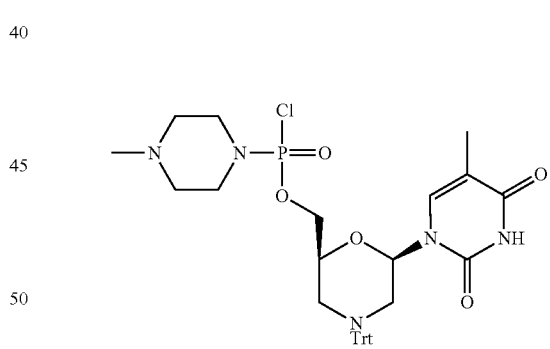

To a cooled (ice/water bath) DCM solution (10 mL) of phosphorus oxychloride (1.02 mL, 11.0 mmol) was added dropwise 2,6-lutidine (3.49 mL, 29.9 mmol) then a DCM solution (10 mL) of methyl piperazine (1.00 g, 10.0 mmol) was added dropwise and stirring continued for 1 h. A DCM solution (10 mL) of Mo(Tr)T (2) (4.82 g, 10.0 mmol) and NMI (79 µL, 1.0 mmol) was added and stirred 4 h then loaded directly onto column. Chromatography [SiO$_2$ column (80 g), DCM/Acetone with 2% TEA eluant (gradient 1:0 to 0:1)] to afford the title compound (0.8 g) as a white foam. ESI/MS calcd. for 1-(4-nitrophenyl)piperazine derivative $C_{43}H_{48}N_7O_8P$ 834.4, found m/z=835.5 (M+1).

Example 5: ((2S,6R)-6-(5-methyl-2,4-dioxo-3,4-dihydropyrimidin-1(2H)-yl)-4-tritylmorpholin-2-yl) methyl (4-ethylpiperazin-1-yl)phosphonochloridate

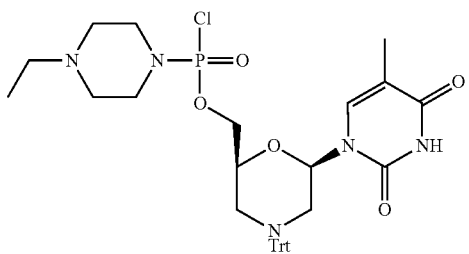

The title compound was synthesized in a manner analogous to that described in Example 4 to afford the title compound (11.5 g) as a white foam. ESI/MS calcd. for 1-(4-nitrophenyl)piperazine derivative $C_{45}H_{53}N_8O_7P$ 848.4, found m/z=849.7 (M+1).

Example 6: ((2S,6R)-6-(6-benzamido-9H-purin-9-yl)-4-tritylmorpholin-2-yl)methyl (4-ethylpiperazin-1-yl)phosphonochloridate

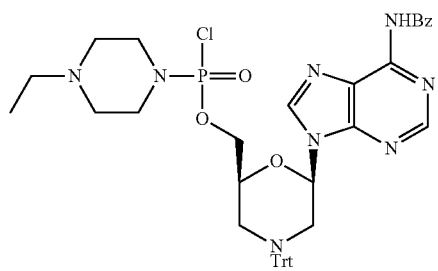

The title compound was synthesized in a manner analogous to that described in Example 4 to afford the title compound (4.5 g) as a white foam. ESI/MS calcd. for 1-(4-nitrophenyl)piperazine derivative $C_{52}H_{56}N_{11}O_6P$ 961.4, found m/z=962.8 (M+1).

Example 7: ((2S,6R)-6-(5-methyl-2,4-dioxo-3,4-dihydropyrimidin-1(2H)-yl)-4-tritylmorpholin-2-yl) methyl (4-isopropylpiperazin-1-yl)phosphonochloridate

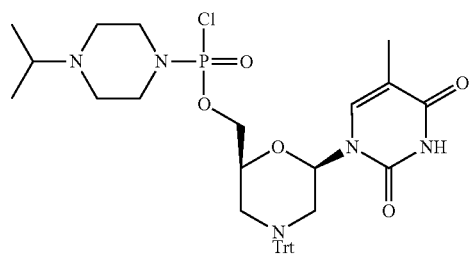

The title compound was synthesized in a manner analogous to that described in Example 4 to afford the title compound (3.5 g) as a white foam. ESI/MS calcd. for 1-(4-nitrophenyl)piperazine derivative $C_{46}H_{55}N_8O_7P$ 862.4, found m/z=863.7 (M+1).

Example 8: ((2S,6R)-6-(5-methyl-2,4-dioxo-3,4-dihydropyrimidin-1(2H)-yl)-4-tritylmorpholin-2-yl) methyl methyl(2-(2,2,2-trifluoroacetamido)ethyl) phosphoramidochloridate

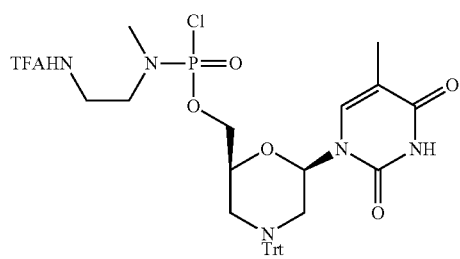

The title compound was synthesized in a manner analogous to that described in Example 4 to afford the title compound (1.0 g) as a white foam. ESI/MS calcd. for 1-(4-nitrophenyl)piperazine derivative $C_{44}H_{48}F_3N_8O_8P$ 904.3, found m/z=903.7 (M-1).

Example 9: ((2S,6R)-6-(5-methyl-2,4-dioxo-3,4-dihydropyrimidin-1(2H)-yl)-4-tritylmorpholin-2-yl) methyl methyl(2-(2,2,2-trifluoro-N-methylacetamido)ethyl)phosphoramidochloridate

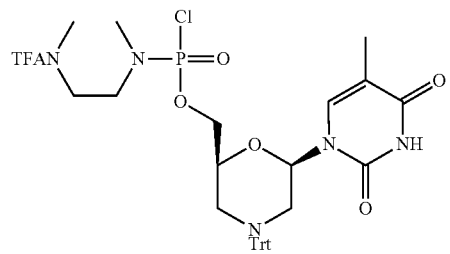

The title compound was synthesized in a manner analogous to that described in Example 4 to afford the title compound (1.8 g) as a white foam. ESI/MS calcd. for 1-(4-nitrophenyl)piperazine derivative $C_{45}H_{50}F_3N_8O_8P$ 918.3, found m/z=1836.6 (2M+).

Example 10: ((2S,6R)-6-(5-methyl-2,4-dioxo-3,4-dihydropyrimidin-1(2H)-yl)-4-tritylmorpholin-2-yl) methyl (4-(2,2,2-trifluoroacetamido)piperidin-1-yl) phosphonochloridate

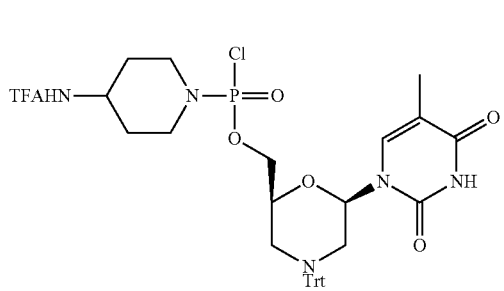

To a cooled solution (ice/water bath) of phosphorus oxychloride (17.7 mL, 190 mmol) in DCM (190 mL) was added dropwise 2,6-lutidine (101 mL, 864 mmol) then Mo(Tr)T (2) (83.5 g, 173 mmol) portionwise over 15 min (int. temp. 0-10° C.) and stirred. After 30 min, the 4-aminopiperidine monotrifluoroacetamide (48.9 g, ~190 mmol) was added dropwise over 15 min (int. temp. 0-8° C.) and stirred. After 1 h, DIPEA (50 mL) was added dropwise (int. temp. 0-10° C.) and stirred 1 h. The reaction was washed with citric acid solution (500 mL×3, 10% w/v aq), dried (MgSO$_4$), filtered and concentrated to a viscous oil which was loaded directly onto column. Chromatography [SiO$_2$ column (330 g), hexanes/EtOAc eluant (gradient 1:0 to 0:1)] to afford the title compound (91.3 g, 70% yield) as a white foam. ESI/MS calcd. for 1-(4-nitrophenyl)piperazine derivative C$_{43}$H$_{48}$N$_7$O$_8$P 930.9, found m/z=954.4 (M+Na).

Examples 13-37 were prepared via procedure A described above.

Example 11: (6-(5-methyl-2,4-dioxo-3,4-dihydropyrimidin-1(2H)-yl)-4-tritylmorpholin-2-yl)methyl (4-(1-(2,2,2-trifluoroacetyl)piperidin-4-yl)piperazin-1-yl)phosphonochloridate Example 12: (6-(5-methyl-2,4-dioxo-3,4-dihydropyrimidin-1(2H)-yl)-4-tritylmorpholin-2-yl)methyl (4-morpholinopiperidin-1-yl)phosphonochloridate Example 13: (6-(5-methyl-2,4-dioxo-3,4-dihydropyrimidin-1(2H)-yl)-4-tritylmorpholin-2-yl)methyl bis(3-(2,2,2-trifluoroacetamido)propyl)phosphoramidochloridate

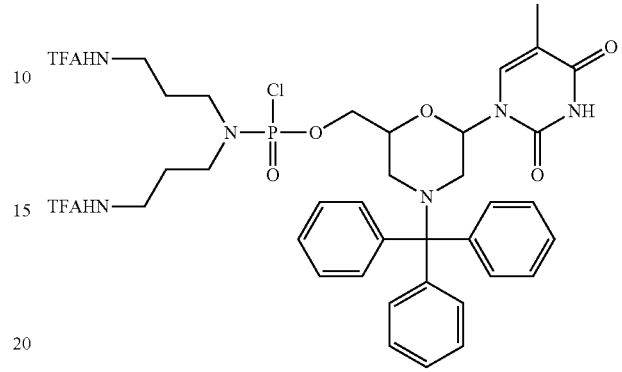

Example 14: (6-(5-methyl-2,4-dioxo-3,4-dihydropyrimidin-1(2H)-yl)-4-tritylmorpholin-2-yl)methyl [1,4'-bipiperidin]-1'-ylphosphonochloridate

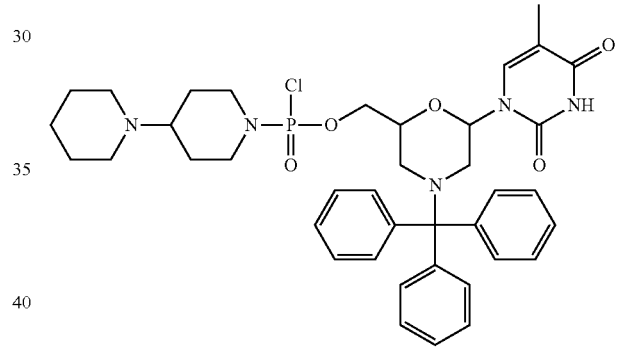

Examples 15 through 20 below were prepared via procedure B described above.

Example 15: (6-(5-methyl-2,4-dioxo-3,4-dihydropyrimidin-1(2H)-yl)-4-tritylmorpholin-2-yl)methyl (4-(pyrimidin-2-yl)piperazin-1-yl)phosphonochloridate

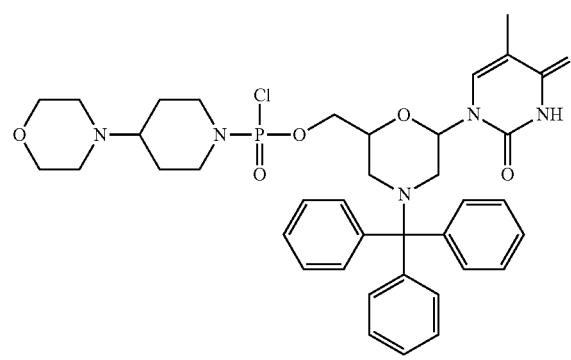

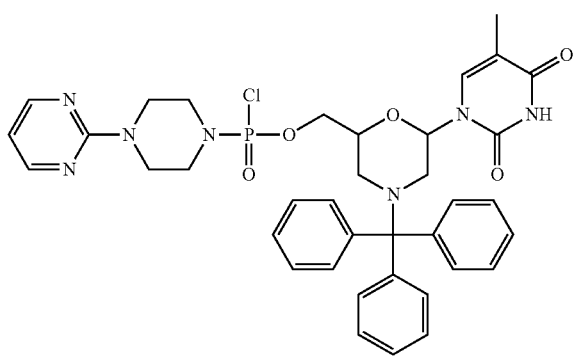 [SMILES: Cc1cn(C2CN(C(c3ccccc3)(c3ccccc3)c3ccccc3)CC(COP(=O)(Cl)N3CCN(c4ncccn4)CC3)O2)c(=O)[nH]c1=O]

Example 16: (6-(5-methyl-2,4-dioxo-3,4-dihydropyrimidin-1(2H)-yl)-4-tritylmorpholin-2-yl)methyl (4-(2-(dimethylamino)ethyl)piperazin-1-yl)phosphonochloridate

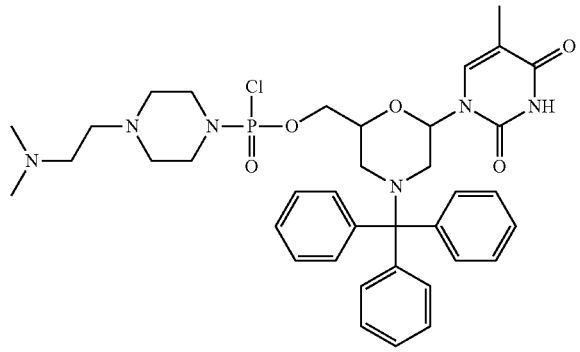 [SMILES: Cc1cn(C2CN(C(c3ccccc3)(c3ccccc3)c3ccccc3)CC(COP(=O)(Cl)N3CCN(CCN(C)C)CC3)O2)c(=O)[nH]c1=O]

Example 17: (6-(5-methyl-2,4-dioxo-3,4-dihydropyrimidin-1(2H)-yl)-4-tritylmorpholin-2-yl)methyl (4-phenylpiperazin-1-yl)phosphonochloridate

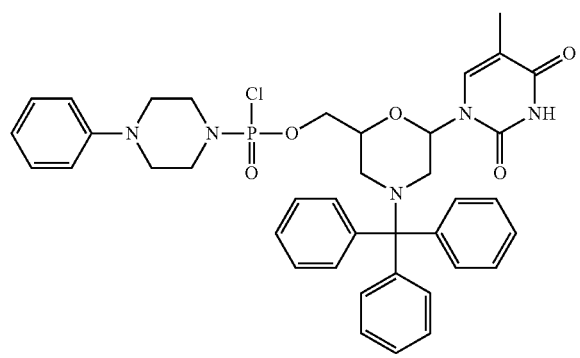 [SMILES: Cc1cn(C2CN(C(c3ccccc3)(c3ccccc3)c3ccccc3)CC(COP(=O)(Cl)N3CCN(c4ccccc4)CC3)O2)c(=O)[nH]c1=O]

Example 18: (6-(5-methyl-2,4-dioxo-3,4-dihydropyrimidin-1(2H)-yl)-4-tritylmorpholin-2-yl)methyl (4-(2,2,2-trifluoro-N-methylacetamido)piperidin-1-yl)phosphonochloridate

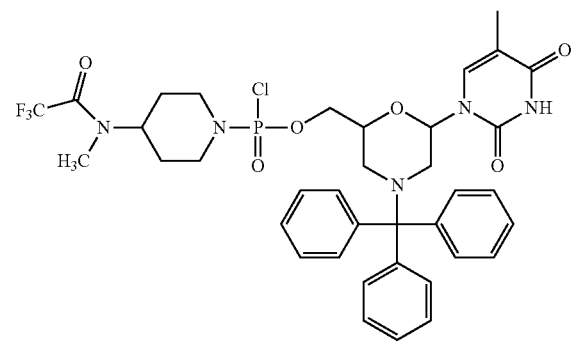 [SMILES: Cc1cn(C2CN(C(c3ccccc3)(c3ccccc3)c3ccccc3)CC(COP(=O)(Cl)N3CCC(N(C)C(=O)C(F)(F)F)CC3)O2)c(=O)[nH]c1=O]

Example 19: (6-(5-methyl-2,4-dioxo-3,4-dihydropyrimidin-1(2H)-yl)-4-tritylmorpholin-2-yl)methyl methyl(3-(2,2,2-trifluoro-N-methylacetamido)propyl)phosphoramidochloridate

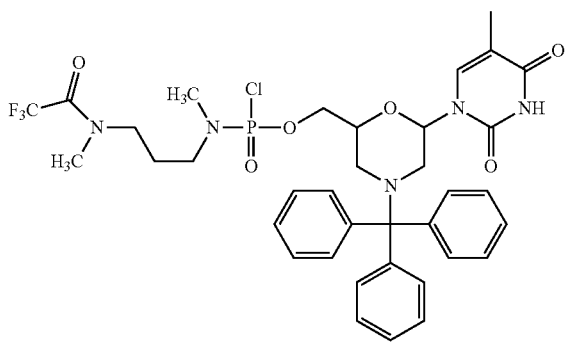 [SMILES: Cc1cn(C2CN(C(c3ccccc3)(c3ccccc3)c3ccccc3)CC(COP(=O)(Cl)N(C)CCCN(C)C(=O)C(F)(F)F)O2)c(=O)[nH]c1=O]

Example 20: ((2S,6R)-6-(6-benzamido-9H-purin-9-yl)-4-tritylmorpholin-2-yl)methyl (4-(2,2,2-trifluoroacetamido)piperidin-1-yl)phosphonochloridate

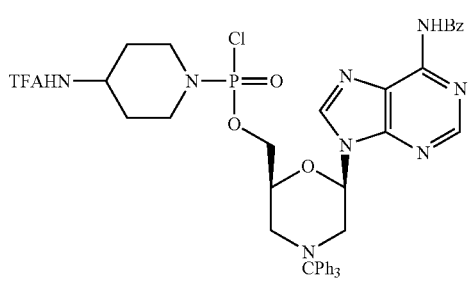

Example 21: (4-(pyrrolidin-1-yl)piperidin-1-yl)phosphonic dichloride hydrochloride

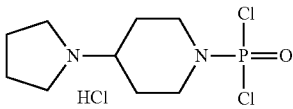

To a cooled (ice/water bath) solution of phosphorus oxychloride (5.70 mL, 55.6 mmol) in DCM (30 mL) was added 2,6-lutidine (19.4 mL, 167 mmol) and a DCM solution (30 mL) of 4-(1-pyrrolidinyl)-piperidine (8.58 g, 55.6 mmol) and stirred for 1 hour. The suspension was filtered and solid washed with excess diethyl ether to afford the title pyrrolidine (17.7 g, 91% yield) as a white solid. ESI/MS calcd. for 1-(4-nitrophenyl)piperazine derivative $C_{19}H_{30}N_5O_4P$ 423.2, found m/z=422.2 (M-1).

Example 22: ((2S,6R)-6-(5-methyl-2,4-dioxo-3,4-dihydropyrimidin-1(2H)-yl)-4-tritylmorpholin-2-yl)methyl (4-(pyrrolidin-1-yl)piperidin-1-yl)phosphonochloridate hydrochloride

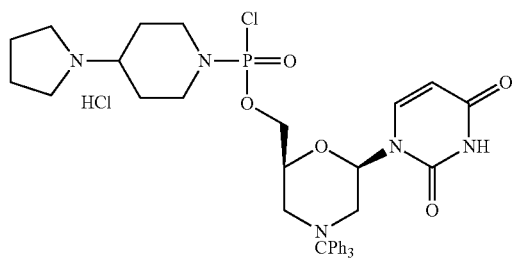

To a stirred, cooled (ice/water bath) solution of the dichlorophosphoramidate from Example 21 (17.7 g, 50.6 mmol) in DCM (100 mL) was added a DCM solution (100 mL) of Mo(Tr)T (2) (24.5 g, 50.6 mmol), 2,6-Lutidine (17.7 mL, 152 mmol), and 1-methylimidazole (0.401 mL, 5.06 mmol) dropwise over 10 minutes. The bath was allowed to warm to ambient temperature as suspension was stirred. After 6 hours, the suspension was poured onto diethyl ether (1 L), stirred 15 minutes, filtered and solid washed with additional ether to afford a white solid (45.4 g). The crude product was purified by chromatography [SiO$_2$ column (120 gram), DCM/MeOH eluant (gradient 1:0 to 6:4)], and the combined fractions were poured onto diethyl ether (2.5 L), stirred 15 min, filtered, and the resulting solid washed with additional ether to afford the title compound (23.1 g, 60% yield) as a white solid. ESI/MS calcd. for 1-(4-nitrophenyl) piperazine derivative C$_{48}$H$_{57}$N$_8$O$_7$P 888.4, found m/z=887.6 (M-1).

Preparation of Morpholino Oligomers

Preparation of trityl piperazine phenyl carbamate 1b (see FIG. 1): To a cooled suspension of compound 1a in dichloromethane (6 mL/g 11) was added a solution of potassium carbonate (3.2 eq) in water (4 mL/g potassium carbonate). To this two-phase mixture was slowly added a solution of phenyl chloroformate (1.03 eq) in dichloromethane (2 g/g phenyl chloroformate). The reaction mixture was warmed to 20° C. Upon reaction completion (1-2 hr), the layers were separated. The organic layer was washed with water, and dried over anhydrous potassium carbonate. The product 1b was isolated by crystallization from acetonitrile. Yield=80%.

Preparation of carbamate alcohol 1c: Sodium hydride (1.2 eq) was suspended in 1-methyl-2-pyrrolidinone (32 mL/g sodium hydride). To this suspension were added triethylene glycol (10.0 eq) and compound 1b (1.0 eq). The resulting slurry was heated to 95° C. Upon reaction completion (1-2 hr), the mixture was cooled to 20° C. To this mixture was added 30% dichloromethane/methyl tert-butyl ether (v:v) and water. The product-containing organic layer was washed successively with aqueous NaOH, aqueous succinic acid, and saturated aqueous sodium chloride. The product 1c was isolated by crystallization from dichloromethane/methyl tert-butyl ether/heptane. Yield=90%.

Preparation of Tail acid 1d: To a solution of compound 1c in tetrahydrofuran (7 mL/g 36) was added succinic anhydride (2.0 eq) and DMAP (0.5 eq). The mixture was heated to 50° C. Upon reaction completion (5 hr), the mixture was cooled to 20° C. and adjusted to pH 8.5 with aqueous NaHCO$_3$. Methyl tert-butyl ether was added, and the product was extracted into the aqueous layer. Dichloromethane was added, and the mixture was adjusted to pH 3 with aqueous citric acid. The product-containing organic layer was washed with a mixture of pH=3 citrate buffer and saturated aqueous sodium chloride. This dichloromethane solution of 1d was used without isolation in the preparation of compound 1e.

Preparation of 1e: To the solution of compound 1d was added N-hydroxy-5-norbornene-2,3-dicarboxylic acid imide (HONB) (1.02 eq), 4-dimethylaminopyridine (DMAP) (0.34 eq), and then 1-(3-dimethylaminopropyl)-N'-ethylcarbodiimide hydrochloride (EDC) (1.1 eq). The mixture was heated to 55° C. Upon reaction completion (4-5 hr), the mixture was cooled to 20° C. and washed successively with 1:1 0.2 M citric acid/brine and brine. The dichloromethane solution underwent solvent exchange to acetone and then to N,N-dimethylformamide, and the product was isolated by precipitation from acetone/N,N-dimethylformamide into saturated aqueous sodium chloride. The crude product was reslurried several times in water to remove residual N,N-dimethylformamide and salts. Yield=70% of 1e from compound 1c. Introduction of the activated "Tail" onto the disulfide anchor-resin was performed in NMP by the procedure used for incorporation of the subunits during solid phase synthesis.

Preparation of the Solid Support for Synthesis of Morpholino Oligomers (see FIG. 2): This procedure was performed in a silanized, jacketed peptide vessel (custom made by ChemGlass, N.J., USA) with a coarse porosity (40-60 μm) glass frit, overhead stirrer, and 3-way Teflon stopcock to allow N2 to bubble up through the frit or a vacuum extraction. Temperature control was achieved in the reaction vessel by a circulating water bath.

The resin treatment/wash steps in the following procedure consist of two basic operations: resin fluidization and solvent/solution extraction. For resin fluidization, the stopcock was positioned to allow N2 flow up through the frit and the specified resin treatment/wash was added to the reactor and allowed to permeate and completely wet the resin. Mixing was then started and the resin slurry mixed for the specified time. For solvent/solution extraction, mixing and N2 flow were stopped and the vacuum pump was started and then the stopcock was positioned to allow evacuation of resin treatment/wash to waste. All resin treatment/wash volumes were 15 mL/g of resin unless noted otherwise.

To aminomethylpolystyrene resin (100-200 mesh; ~1.0 mmol/g N2 substitution; 75 g, 1 eq, Polymer Labs, UK, part #1464-X799) in a silanized, jacketed peptide vessel was added 1-methyl-2-pyrrolidinone (NMP; 20 ml/g resin) and the resin was allowed to swell with mixing for 1-2 hr. Following evacuation of the swell solvent, the resin was washed with dichloromethane (2×1-2 min), 5% diisopropylethylamine in 25% isopropanol/dichloromethane (2×3-4 min) and dichloromethane (2×1-2 min). After evacuation of the final wash, the resin was fluidized with a solution of disulfide anchor 2a in 1-methyl-2-pyrrolidinone (0.17 M; 15 mL/g resin, ~2.5 eq) and the resin/reagent mixture was heated at 45° C. for 60 hr. On reaction completion, heating was discontinued and the anchor solution was evacuated and the resin washed with 1-methyl-2-pyrrolidinone (4×3-4 min) and dichloromethane (6×1-2 min). The resin was treated with a solution of 10% (v/v) diethyl dicarbonate in dichloromethane (16 mL/g; 2×5-6 min) and then washed with dichloromethane (6×1-2 min). The resin 2b was dried under a N2 stream for 1-3 hr and then under vacuum to constant weight (±2%). Yield: 110-150% of the original resin weight.

Determination of the Loading of Aminomethylpolystyrene-disulfide resin: The loading of the resin (number of potentially available reactive sites) is determined by a spectrometric assay for the number of triphenylmethyl (trityl) groups per gram of resin.

A known weight of dried resin (25±3 mg) is transferred to a silanized 25 ml volumetric flask and ~5 mL of 2% (v/v) trifluoroacetic acid in dichloromethane is added. The contents are mixed by gentle swirling and then allowed to stand for 30 min. The volume is brought up to 25 mL with additional 2% (v/v) trifluoroacetic acid in dichloromethane and the contents thoroughly mixed. Using a positive displacement pipette, an aliquot of the trityl-containing solution (500 μL) is transferred to a 10 mL volumetric flask and the volume brought up to 10 mL with methanesulfonic acid.

The trityl cation content in the final solution is measured by UV absorbance at 431.7 nm and the resin loading calculated in trityl groups per gram resin (μmol/g) using the appropriate volumes, dilutions, extinction coefficient (ε: 41 μmol-1 cm-1) and resin weight. The assay is performed in triplicate and an average loading calculated.

The resin loading procedure in this example will provide resin with a loading of approximately 500 μmol/g. A loading of 300-400 in μmol/g was obtained if the disulfide anchor incorporation step is performed for 24 hr at room temperature.

Tail loading: Using the same setup and volumes as for the preparation of aminomethylpolystyrene-disulfide resin, the Tail can be introduced into the molecule. For the coupling step, a solution of 1e (0.2 M) in NMP containing 4-ethylmorpholine (NEM, 0.4 M) was used instead of the disulfide anchor solution. After 2 hr at 45° C., the resin 2b was washed twice with 5% diisopropylethylamine in 25% isopropanol/dichloromethane and once with DCM. To the resin was added a solution of benzoic anhydride (0.4 M) and NEM (0.4 M). After 25 min, the reactor jacket was cooled to room temperature, and the resin washed twice with 5% diisopropylethylamine in 25% isopropanol/dichloromethane and eight times with DCM. The resin 2c was filtered and dried under high vacuum. The loading for resin 2c is defined to be the loading of the original aminomethylpolystyrene-disulfide resin 2b used in the Tail loading.

Solid Phase Synthesis: Morpholino Oligomers were prepared on a Gilson AMS-422 Automated Peptide Synthesizer in 2 mL Gilson polypropylene reaction columns (Part #3980270). An aluminum block with channels for water flow was placed around the columns as they sat on the synthesizer. The AMS-422 will alternatively add reagent/wash solutions, hold for a specified time, and evacuate the columns using vacuum.

For oligomers in the range up to about 25 subunits in length, aminomethylpolystyrene-disulfide resin with loading near 500 μmol/g of resin is preferred. For larger oligomers, aminomethylpolystyrene-disulfide resin with loading of 300-400 μmol/g of resin is preferred. If a molecule with 5'-Tail is desired, resin that has been loaded with Tail is chosen with the same loading guidelines.

The following reagent solutions were prepared:

Detrylation Solution: 10% Cyanoacetic Acid (w/v) in 4:1 dichloromethane/acetonitrile; Neutralization Solution: 5% Diisopropylethylamine in 3:1 dichloromethane/isopropanol; Coupling Solution: 0.18 M (or 0.24 M for oligomers having grown longer than 20 subunits) activated Morpholino Subunit of the desired base and linkage type and 0.4 M N ethylmorpholine, in 1,3-dimethylimidazolidinone. Dichloromethane (DCM) was used as a transitional wash separating the different reagent solution washes.

On the synthesizer, with the block set to 42° C., to each column containing 30 mg of aminomethylpolystyrene-disulfide resin (or Tail resin) was added 2 mL of 1-methyl-2-pyrrolidinone and allowed to sit at room temperature for 30 min. After washing with 2 times 2 mL of dichloromethane, the following synthesis cycle was employed:

| Step | Volume | Delivery | Hold time |
|---|---|---|---|
| Detrylation | 1.5 mL | Manifold | 15 seconds |
| Detrylation | 1.5 mL | Manifold | 15 seconds |
| Detrylation | 1.5 mL | Manifold | 15 seconds |
| Detrylation | 1.5 mL | Manifold | 15 seconds |
| Detrylation | 1.5 mL | Manifold | 15 seconds |
| Detrylation | 1.5 mL | Manifold | 15 seconds |
| Detrylation | 1.5 mL | Manifold | 15 seconds |
| DCM | 1.5 mL | Manifold | 30 seconds |
| Neutralization | 1.5 mL | Manifold | 30 seconds |
| Neutralization | 1.5 mL | Manifold | 30 seconds |
| Neutralization | 1.5 mL | Manifold | 30 seconds |
| Neutralization | 1.5 mL | Manifold | 30 seconds |
| Neutralization | 1.5 mL | Manifold | 30 seconds |
| Neutralization | 1.5 mL | Manifold | 30 seconds |
| DCM | 1.5 mL | Manifold | 30 seconds |
| Coupling | 350 uL-500 uL | Syringe | 40 minutes |
| DCM | 1.5 mL | Manifold | 30 seconds |
| Neutralization | 1.5 mL | Manifold | 30 seconds |
| Neutralization | 1.5 mL | Manifold | 30 seconds |
| DCM | 1.5 mL | Manifold | 30 seconds |
| DCM | 1.5 mL | Manifold | 30 seconds |
| DCM | 1.5 mL | Manifold | 30 seconds |

The sequences of the individual oligomers were programmed into the synthesizer so that each column receives the proper coupling solution (A, C, G, T, I) in the proper sequence. When the oligomer in a column had completed incorporation of its final subunit, the column was removed from the block and a final cycle performed manually with a coupling solution comprised of 4-methoxytriphenylmethyl chloride (0.32 M in DMI) containing 0.89 M 4-ethylmorpholine.

Cleavage from the resin and removal of bases and backbone protecting groups: After methoxytritylation, the resin was washed 8 times with 2 mL 1-methyl-2-pyrrolidinone. One mL of a cleavage solution consisting of 0.1 M 1,4-dithiothreitol (DTT) and 0.73 M triethylamine in 1-methyl-2-pyrrolidinone was added, the column capped, and allowed to sit at room temperature for 30 min After that time, the solution was drained into a 12 mL Wheaton vial. The greatly shrunken resin was washed twice with 300 μL of cleavage solution. To the solution was added 4.0 mL conc aqueous ammonia (stored at −20° C.), the vial capped tightly (with Teflon lined screw cap), and the mixture swirled to mix the solution. The vial was placed in a 45° C. oven for 16-24 hr to effect cleavage of base and backbone protecting groups.

Initial Oligomer Isolation: The vialed ammonolysis solution was removed from the oven and allowed to cool to room temperature. The solution was diluted with 20 mL of 0.28% aqueous ammonia and passed through a 2.5×10 cm column containing Macroprep HQ resin (BioRad). A salt gradient (A: 0.28% ammonia with B: 1 M sodium chloride in 0.28% ammonia; 0-100% B in 60 min) was used to elute the methoxytrityl containing peak. The combined fractions were pooled and further processed depending on the desired product.

Demethoxytritylation of Morpholino Oligomers: The pooled fractions from the Macroprep purification were treated with 1 M H3PO4 to lower the pH to 2.5. After initial mixing, the samples sat at room temperature for 4 min, at which time they are neutralized to pH 10-11 with 2.8% ammonia/water. The products were purified by solid phase extraction (SPE).

Amberchrome CG-300M (Rohm and Haas; Philadelphia, Pa.) (3 mL) is packed into 20 mL fitted columns (BioRad Econo-Pac Chromatography Columns (732-1011)) and the resin rinsed with 3 mL of the following: 0.28% NH4OH/ 80% acetonitrile; 0.5M NaOH/20% ethanol; water; 50 mM H3PO4/80% acetonitrile; water; 0.5 NaOH/20% ethanol; water; 0.28% NH4OH.

The solution from the demethoxytritylation was loaded onto the column and the resin rinsed three times with 3-6 mL 0.28% aqueous ammonia. A Wheaton vial (12 mL) was placed under the column and the product eluted by two washes with 2 mL of 45% acetonitrile in 0.28% aqueous ammonia. The solutions were frozen in dry ice and the vials placed in a freeze dryer to produce a fluffy white powder. The samples were dissolved in water, filtered through a 0.22 micron filter (Pall Life Sciences, Acrodisc 25 mm syringe filter, with a 0.2 micron HT Tuffryn membrane) using a syringe and the Optical Density (OD) was measured on a UV spectrophotometer to determine the OD units of oligomer present, as well as dispense sample for analysis. The solutions were then placed back in Wheaton vials for lyophilization.

Analysis of Morpholino Oligomers: MALDI-TOF mass spectrometry was used to determine the composition of fractions in purifications as well as provide evidence for identity (molecular weight) of the oligomers. Samples were run following dilution with solution of 3,5-dimethoxy-4-hydroxycinnamic acid (sinapinic acid), 3,4,5-trihydoxyacetophenone (THAP) or alpha-cyano-4-hydoxycinnamic acid (HCCA) as matrices.

Cation exchange (SCX) HPLC was performed using a Dionex ProPac SCX-10, 4×250 mm column (Dionex Corporation; Sunnyvale, Calif.) using 25 mM pH=5 sodium acetate 25% acetonitrile (Buffer A) and 25 mM pH=5 sodium acetate 25% acetonitrile 1.5 M potassium chloride (buffer B) (Gradient 10-100% B in 15 min) or 25 mM KH2PO4 25% acetonitrile at pH=3.5 (buffer A) and 25 mM KH2PO4 25% acetonitrile at pH=3.5 with 1.5 M potassium chloride (buffer B) (Gradient 0-35% B in 15 min). The former system was used for positively charged oligomers that do not have a peptide attached, while the latter was used for peptide conjugates.

Purification of Morpholino Oligomers by Cation Exchange Chromatography: The sample is dissolved in 20 mM sodium acetate, pH=4.5 (buffer A) and applied to a column of Source 30 cation exchange resin (GE Healthcare) and eluted with a gradient of 0.5 M sodium chloride in 20 mM sodium acetate and 40% acetonitrile, pH=4.5 (buffer B). The pooled fractions containing product are neutralized with conc aqueous ammonia and applied to an Amberchrome SPE column. The product is eluted, frozen, and lyophilized as above.

Example 23: Selective Reduction of Mutant HTT mRNA Relative to Wild-Type HTT mRNA Using PMO-, APN-, and LNA-Modified Oligonucleotides Patient-derived fibroblasts from an individual with Huntington's Disease (Coriell cell line GM04281; 69 CAG repeats (SEQ ID NO: 41)) were cultured according to standard protocols in Eagle's MEM with 10% FBS. Cells were passaged 3-5 days before the experiment and were approximately 80% confluent at nucleofection. Oligonucleotides were prepared as 1-2 mM stock solutions in nuclease-free water (not treated with DEPC) from which appropriate dilutions were made for nucleofection. Fibroblasts were trypsinized, counted, centrifuged at 90 g for 10 minutes, and 1-5×10e5 cells per well were resuspended in nucleofection Solution P2 (Lonza). Oligonucleotide solution and cells were then added to each well of a Nucleocuvette 16-well strip, and pulsed with program EN-150. Cells were incubated at room temperature for 10 minutes and transferred to a 12-well plate in duplicate. Total RNA was isolated from treated cells after 48 hours using the GE Illustra 96 Spin kit following the manufacturer's recommended protocol. Recovered RNA was stored at −80° C. prior to analysis.

Reverse transcriptase PCR was performed to amplify wild-type and mutant HTT alleles using the SuperScript III One-Step RT-PCR system (Invitrogen). 100 ng total RNA isolated from nucleofected cells was reverse transcribed and amplified with the following gene-specific primers and conditions: HTT-Fwd 5'-atggcgaccctggaaaagctgat 3' (SEQ ID NO: 25); HTT-Rev 5' TGAGGCAGCAGCGGCTG 3' (SEQ ID NO: 26); PCR Program: 60° C. for 30 min RT incubation; 95° C. denature, 60° C. anneal, 72° C. extension, 35 cycles. The amplification solution provided in the One-Step kit was supplemented with Cy5-labeled dCTP (GE) to enable band visualization by fluorescence. Following amplification, PCR products were run on a pre-cast 10% acrylamide/TBE gel (Invitrogen) and visualized on a Typhoon Trio (GE) using the 633 nm excitation laser and 670 nm BP 30 emission filter with the focal plane at the platen surface (see, e.g., FIG. 10). Gels were analyzed with ImageQuant (GE) to determine the intensities of the bands from the mutant and wild-type alleles.

A side by side comparison of mutant HTT mRNA was made between PMOapn, PMO, and LNA oligonucleotides. The results are shown in FIGS. 6-10. The LNA, PMO, and APN oligonucleotides contain the same sequence: 5' GCT GCT GCT GCT GCT GCT GCT G 3' (SEQ ID NO: 21). The LNA oligonucleotides (ordered from Exiqon) contain a DNA backbone with an LNA modification at every T base (7 total modifications). The APN oligonucleotides contain the PMO backbone with an apn modification at every T base (7 total modifications). The PMO oligonucleotides contain the PMO backbone with no additional modifications to any intersubunit linkage.

Cells were nucleofected with the LNA, PMO, or APN oligonucleotide as described above. The RNA remaining 48 hours after the nucleotransfection process was quantified using reverse transcriptase PCR and the PCR products run on an acrylamide gel. The intensity of the gel band representing the wild-type or mutant HTT allele from GM04281 fibroblast cells (Coriell) was normalized to the intensity of the respective wild-type or mutant band of the lowest treated sample. The results are shown in FIG. 6. Each point on the graphs represents the mean of the normalized expression levels from two replicates at each concentration, and two independent experiments were combined to yield the dataset in FIG. 6. Gel intensity quantification was performed with ImageQuant (GE). Intensity normalization, EC50 calculation, and selectivity were analyzed with Microsoft Excel and R.

Mean EC50 values for each allele were calculated from the dataset presented in FIG. 6, as well as selectivity for the mutant allele was calculated from the EC50 of the wild-type and mutant alleles from fibroblasts nucleofected with the same oligonucleotide, using R and Graphpad Prism. A quantitative comparison of the results is shown in FIG. 7 and FIG. 9. A comparison of the EC50 shows that cells treated with the PMO and APN oligonucleotides have reduced mRNA expression of the mutant allele over the wild-type allele compared to LNA. Moreover, the potency of the APN oligonucleotide, based on EC50 values, is improved over the PMO oligonucleotide.

The results show the unexpected reduction in levels of mutant mRNA believed to be responsible for Huntington's disease by the PMO, APN and LNA oligonucleotides, and that the APN oligos were more selective at reducing the expression of mutant mRNA than either the PMO or LNA oligonucleotides.

Example 24: Selective Reduction of Mutant HTT Protein Relative to Wild-Type HTT Protein by PMO- and APN-Modified Oligonucleotides Given the finding that PMO, APN, and LNA-modified oligonucleotides reduced the expression of mutant HTT mRNA to a greater extent than wild type HTT mRNA (Example 23), and the fact that Huntington's Disease ultimately manifests as a result of the toxic gain of function associated with the expression of mutant HTT protein, the effects of PMO-, APN-, and LNA-modified oligonucleotide treatment on mutant and wild-type HTT protein expression were assessed. The sequences and modifications of the oligonucleotides are as described in Example 23.

Experiments were performed to determine mutant and wild-type HTT protein expression in cells treated with APN-, PMO-, and LNA-modified oligonucleotides targeting the trinucleotide repeat region of the human HTT RNA. Cells were nucleofected (Lonza) using a range of doses in duplicate wells using GM04281 fibroblasts (Coriell) from a human patient with Huntington's Disease. After three days, protein lysates were prepared using standard lysis techniques and the BCA assay used to determine protein concentrations of the resulting samples according to the manufacturer's recommended protocol. Equal amounts of total protein from each treated sample were run on duplicate tris-acetate SDS-PAGE gels and transferred to nitrocellulose. Blots were probed with an anti-HTT (MAB2166, Millipore) or anti-β-actin (A1978, Sigma) primary antibody followed by a cy5-congugated secondary antibody. The resulting blots were scanned on a Typhoon Trio (GE) and signal intensity of the mutant and normal HTT protein were quantified separately with ImageQuant (GE) software. Signal intensity of the normal (lower) and mutant (upper) HTT bands were normalized to the β-actin signal within each lane, and then each HTT band was normalized to the corresponding normal or mutant HTT band intensity from an untreated control sample on a separate blot. Protein expression results are plotted for each allele (normal, solid line; mutant, dashed line) as the mean percent of HTT protein expression, +/−1 SD.

The graphs in FIG. 11 were plotted based on densitometric analysis of HTT protein bands from Western blots (FIG. 11, bottom panel). PMO (FIG. 11, left panel) and APN (FIG. 11, middle panel) selectively reduced the expression of mutant HTT protein relative to wild-type HTT protein, with greater selectivity for mutant HTT observed with APN. In contrast, LNA did not selectively reduce the expression of mutant HTT protein relative to wild type HTT protein (FIG. 11, right panel). The high selectivity of APN-modified oligonucleotides for mutant HTT relative to wild-type HTT protein as compared to PMO- or LNA-modified oligonucleotides is also evident when the expression of HTT is plotted as the ratio of wild-type HTT to mutant HTT (FIG. 12). Indeed, treatment with LNA-modified oligonucleotides increased the WT/mutant HTT ratio up to about 5 at a concentration of 4 μM, whereas both PMO- and LNA-modified oligonucleotides had similar WT/mutant HTT ratios of about 2 at the same concentration, although PMO-modified oligonucleotide treatment showed a modest trend of increase in WT/mutant HTT ratio from 0.16 μM to 20 μM. These results collectively suggest that APN-modified oligonucleotides are more effective at selectively reducing the expression of mutant HTT protein relative to wild-type HTT protein than PMO- or LNA-modified oligonucleotides, and that LNA-modified oligonucleotides did not selectively reduce the expression of mutant HTT protein relative to wild-type HTT protein.

Example 25: Selective Reduction of Mutant HTT Protein Relative to Wild-Type HTT Protein Using Oligonucleotides with APN- and Plus-Related Cationic Intersubunit Linkages To assess the selectivity of oligonucleotides with other types of cationic intersubunit linkages for reducing the expression of mutant HTT protein relative to wild-type HTT protein, oligonucleotides with APN- (i.e., APN and map) and plus-related intersubunit linkages (i.e., plus, meda, and etpip) were tested.

```
PMO-^{apn}T:
                                      (SEQ ID NO: 21)
GC^{apn}T GC^{apn}T GC^{apn}T GC^{apn}T GC^{apn}T GC^{apn}T GC^{apn}TG PMO-^{map}T:
                                      (SEQ ID NO: 21)
GC^{map}TGC^{map}TGC^{map}TGC^{map}TGC^{map}TGC^{map}TGC^{map}TG PMOplus:
                                      (SEQ ID NO: 21)
GC + TGC + TGC + TGC + TGC + TGC + TG PMO-^{meda}T:
                                      (SEQ ID NO: 21)
GC^{meda}TGC^{meda}TGC^{meda}TGC^{meda}TGC^{meda}TGC^{meda}TGC^{meda}TG PMO-^{EtpiP}T:
                                      (SEQ ID NO: 21)
GC^{EtpiP}TGC^{EtpiP}TGC^{EtpiP}TGC^{EtpiP}TGC^{EtpiP}TGC^{EtpiP}

TGC^{EtpiP}TG
```

Exemplary structures for APN- and plus-related cationic modifications are shown in FIG. 13. Experiments were performed as described in Example 24.

As shown in FIG. 14, oligonucleotides modified with APN-related linkages, i.e., APN and mapT, showed greater selectivity for mutant HTT over wild-type HTT than PMO-modified oligonucleotides as assessed by WT/mutant HTT ratio (FIG. 14, left panel). All oligonucleotides modified with plus-related linkages (i.e., plusT, medaT, and etpipT) also showed selectivity for mutant HTT over wild-type HTT compared to PMO-modified oligonucleotides, with etpipT-modified oligonucleotides demonstrating the greatest selectivity (FIG. 14, right panel). When the selectivity of APN- and etpipT-modified oligonucleotides was tested in the same assay, both had substantially greater selectivity for mutant HTT relative to wild-type HTT compared to PMO. Moreover, while APN- and etpipT-modified oligonucleotides showed a similar degree of selectivity, APN-modified oligonucleotides exhibited a higher degree of selectivity at lower concentrations. These results suggest that APN- and etpipT-modified oligonucleotides have the highest selectivity for reducing mutant HTT protein relative to wild-type HTT protein among the oligonucleotides tested.

Example 26: In Vivo ICV Administration of PMO and APN in EGFP-654 Mice

Experiments in support of the invention used an eGFP-based assay for in vivo antisense activity to evaluate oligomers comprising modified intersubunit linkages of the invention. The transgenic eGFP mouse model in which the eGFP-654 transgene, is expressed uniformly throughout the body has been described previously (Sazani, Gemignani et al. 2002). This model uses a splicing assay for activity in which the modified oligomers of the present invention block aberrant splicing and restore correct splicing of the modified enhanced green fluorescent protein (eGFP) pre-mRNA. In this approach, antisense activity of each oligomer is directly proportional to up-regulation of the eGFP reporter. As a result, the functional effects of the same oligomer can be monitored in almost every tissue. This is in contrast to oligomers targeted to genes whose expression is restricted to or is phenotypically relevant in only certain tissues. In the eGFP-654 mice, the pre-mRNA was readily detectable in all tissues although smaller amounts were found in the bone marrow, skin and brain. The level of translated eGFP is proportional to the potency of the antisense oligomers and their concentration at the site of action. RT-PCR of total RNA isolated from various tissues showed expression of eGFP-654 transcript in all tissues surveyed.

The specific PMO-X modifications of the compounds described in this example are shown below:

```
0-1-0-730 (PMO):
                                         (SEQ ID NO: 22)
GCT ATT ACC TTA ACC CAG

NG-10-0245 (APN):
                                         (SEQ ID NO: 22)
GC^{apn}T A^{apn}T^{apn}T ACC T^{apn}TA ACC CAG
```

Neutrally charged PMO, or PMO modified with cationic backbone charges (APN), targeting the eGFP transgene was administered into the left lateral ventricle of EGFP-654 mice by a single intracebreroventricular (ICV) injection using a stereotaxic apparatus. Doses consisted of either 5 mg/kg (left panel, PMO or APN) for all mice or spanned a range of doses (right panel, 2.5 up to 40 mg/kg, APN only). Two weeks post-injection, mice were euthanized and the brain was removed and cut in half sagittally at the midline into left and right hemispheres. Each hemisphere was imaged on a Typhoon Trio (GE) by placing the cut surface face down on the flatbed platen. Scans were collected using a 488 nm laser to excite eGFP fluorescence. The resulting images were analyzed with ImageQuant software (GE) to quantify the fluorescence intensity of each hemisphere. The total detected fluorescence intensity within each hemisphere was divided by the number of pixels present in that hemisphere to yield an area-independent average fluorescence value for each half of the brain. Activity results for each surviving animal in a treatment group are expressed as points on the scatter plot. The mean fluorescence of the group is indicated by the horizontal line, +/−1 SD.

As shown in FIG. 16 (left panel), while saline did not induce EGFP expression in the brain, PMO and APN treatment did, with APN-modified oligonucleotide injection inducing EGFP expression to a greater extent than PMO-modified oligonucleotide injection. APN-modified oligonucleotide injection also increased EGFP expression in a dose-dependent manner (FIG. 16, right panel). A representative typhoon image from saline-, PMO-, and APN-treated eGFP-654 mice showing the localization of the EGFP signal demonstrates that ICV-injected oligomer activity is preferentially expressed within specific regions of the brain (FIG. 16, bottom panel). Together, these results indicate that oligomer activity in the brain is enhanced by cationic modification of the PMO backbone.

Example 27: Therapeutic Use of Antisense Oligonucleotides In Vivo

Any of the antisense oligonucleotides, with any of the cationic linkages, preferably APN linkages, described herein can be used in animal models of nucleotide repeat diseases known in the art. Such animal models include, but are not limited to, BACHD, YAC128, and R6/2 mice for Huntington's disease (e.g., as disclosed in Kordasiewicz et al., Neuron 2012; 74:1031-44), and $HSA^{LR}$ for DM1 (e.g., as disclosed in Wheeler et al., Nature 2012; 488:111-5). Although animal models of ALS with expanded nucleotide repeats do not currently exist, such models can be readily generated using art-recognized methods by, e.g., replacing the wild-type C9ORF72 gene locus in mice with a mutant C9ORF72 gene having expanded GGGGCC hexanucleotide repeats (see, e.g., DeJesus-Hernandez et al., supra; Renton et al, supra) (i.e., mutant C9ORF72 knock-in mice).

---

What is claimed:

1. An antisense oligonucleotide of 10-40 nucleotides in length having a sequence complementary to an expanded DNA repeat which is associated with a human disease, wherein the antisense oligonucleotide consists of nucleotides, wherein each nucleotide is a nucleotide with the structure of formula:

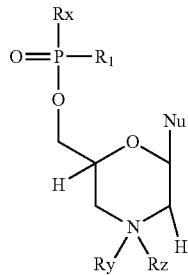

wherein Nu is a nucleobase;
$R_1$ is —N(Me)$_2$
$R_x$ is selected from the group consisting of HO—, a nucleotide, and piperazinyl;
$R_y$ is selected from the group consisting of hydrogen, a $C_1$-$C_6$ alkyl, a nucleotide, a cell penetrating peptide moiety, an amino acid, a formamidinyl moiety, and acyl; and,
$R_z$ is selected from the group consisting of null, hydrogen, a $C_1$-$C_6$ alkyl, and acyl; and pharmaceutically acceptable salts thereof,
and wherein the sequence is selected from the group consisting of (CAG)$_7$, (CCG)$_n$, (CTG)$_n$, (TTC)$_n$, (NGC)$_n$, (GNC)$_n$, (AGAAT)$_n$, and (CGCG$_4$CG$_4$)$_n$, wherein N is any nucleotide and n is from 3 to 10.

2. The antisense oligonucleotide of claim 1, wherein the human disease is Myotonic dystrophy type 1 or type 2.

3. The antisense oligonucleotide of claim 1, wherein $R_y$ is a G nucleotide.

4. A pharmaceutical composition comprising the antisense oligonucleotide of claim 1 and a pharmaceutically acceptable carrier.

5. A method of treating Myotonic dystrophy type 1 or type 2 in a subject comprising administering the composition of claim 4.

6. An antisense oligonucleotide comprising a repeated three nucleotide sequence consisting of the formula:

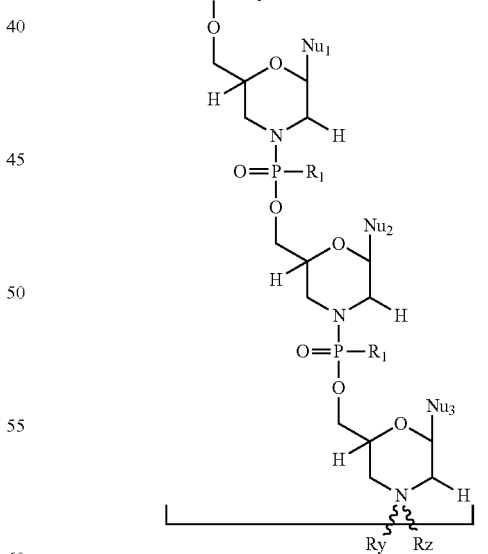

wherein:
Nu$_1$, Nu$_2$ and Nu$_3$ are nucleobases selected from the group consisting of adenine, guanine, thymine, uracil, cytosine, and hypoxanthine;
n is from about 3 to about 10 representing the number of repeats of the nucleotide sequence (Nu$_1$, Nu$_2$, Nu$_3$);

$R_1$ is —N(Me)$_2$ $R_x$ is selected from the group consisting of HO—, a nucleotide, and piperazinyl;

$R_y$ is selected from the group consisting of hydrogen, a C$_1$-C$_6$ alkyl, a nucleotide, a cell penetrating peptide moiety, an amino acid, and a formamidinyl moiety; and, $R_z$ is selected from the group consisting of null, hydrogen, a C$_1$-C$_6$ alkyl, and acyl; and pharmaceutically acceptable salts thereof;

and wherein the nucleotide sequence is selected from the group consisting of (CAG)$_7$, (CCG)$_n$, (CTG)$_n$, (TTC)$_n$, (NGC)$_n$, and (GNC)$_n$, wherein N is any nucleotide and n is from 3 to 10.

7. The antisense oligonucleotide of claim 6, wherein the three nucleotide sequence is selected from the group consisting of (CCG), (CTG), (TTC), (NGC), and (GNC), wherein N is any nucleotide.

8. The antisense oligonucleotide of claim 6, wherein the repeated three nucleotide sequence is (CAG)$_7$.

9. The antisense oligonucleotide of claim 6, wherein Ry is a G nucleotide.

10. A pharmaceutical composition comprising the antisense oligonucleotide of claim 6 and a pharmaceutically acceptable carrier.

11. A method of treating Myotonic dystrophy type 1 or type 2 in a subject comprising administering the composition of claim 10.

12. The antisense oligonucleotide of claim 1, wherein the antisense oligonucleotide is 15-30 nucleotides in length.

13. The antisense oligonucleotide of claim 1, wherein the antisense oligonucleotide is 18-30 nucleotides in length.

14. The antisense oligonucleotide of claim 1, wherein the antisense oligonucleotide is 20-30 nucleotides in length.

15. The antisense oligonucleotide of claim 6, wherein the antisense oligonucleotide is 15-30 nucleotides in length.

16. The antisense oligonucleotide of claim 6, wherein the antisense oligonucleotide is 18-30 nucleotides in length.

17. The antisense oligonucleotide of claim 6, wherein the antisense oligonucleotide is 20-30 nucleotides in length.

18. An antisense oligonucleotide consisting of a repeated three nucleotide sequence having the formula:

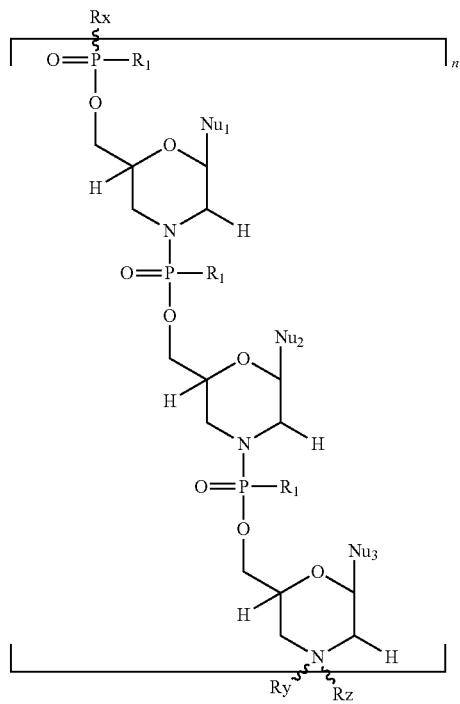

wherein:

Nu$_1$, Nu$_2$ and Nu$_3$ are a repeated three nucleotide sequence, wherein the repeated three nucleotide sequence is (CAG)$_7$;

n is 7;

$R_1$ is —N(Me)$_2$ $R_x$ is HO—;

$R_y$ is hydrogen; and, $R_z$ is null.

* * * * *

SEQUENCE LISTING

```
<160> NUMBER OF SEQ ID NOS: 46

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gaatagaata gaatagaata g                                              21

<210> SEQ ID NO 2
<211> LENGTH: 26
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 2
gaatagaata gaatagaata gaatag                                              26

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ctgctgctgc tgctgctgct g                                                   21

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ctgctgctgc tgctgctgct gctgctg                                             27

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
caggcaggca ggcaggcagg                                                     20

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
caggcaggca ggcaggcagg caggcag                                             27

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ccgccgccgc cgccgccgcc g                                                   21

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 8
ccgccgccgc cgccgccgcc gccgccg                                27

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
cagcagcagc agcagcagca g                                      21

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
cagcagcagc agcagcagca gcagcag                                27

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ttcttcttct tcttcttctt c                                      21

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ttcttcttct tcttcttctt cttcttc                                27

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
caggcccagg cccaggccca ggcc                                   24

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 14
caggcccagg cccaggccca ggcccaggcc                                          30

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ggccccggcc ccggccccgg cccc                                                24

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ggccccggcc ccggccccgg cggccccggc                                          30

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ccattccatt ccattccatt cc                                                  22

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ccattccatt ccattccatt ccattcc                                             27

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
cgcggggcgg ggcgcggggc gg                                                  22

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 20
cgcggggcgg ggcgcggggc ggggcgcggc                                              30

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gctgctgctg ctgctgctgc tg                                                      22

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gctattacct taacccag                                                           18

<210> SEQ ID NO 23
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
cgcggggcgg gg                                                                 12

<210> SEQ ID NO 24
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ggccccggcc ccggccccgg ccccggcccc ggccccggcc ccggccccgg ccccggcccc            60

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
atggcgaccc tggaaaagct gat                                                     23

<210> SEQ ID NO 26
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tgaggcagca gcggctg                                                    17

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(30)
<223> OTHER INFORMATION: This sequence may encompass 3-10 'ccg'
      repeating units

<400> SEQUENCE: 27
ccgccgccgc cgccgccgcc gccgccgccg                                      30

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(30)
<223> OTHER INFORMATION: This sequence may encompass 3-10 'ctg'
      repeating units

<400> SEQUENCE: 28
ctgctgctgc tgctgctgct gctgctgctg                                      30

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(30)
<223> OTHER INFORMATION: This sequence may encompass 3-10 'ttc'
      repeating units

<400> SEQUENCE: 29
ttcttcttct tcttcttctt cttcttcttc                                      30

<210> SEQ ID NO 30
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: misc_feature
<222> LOCATION: (1)..(30)
<223> OTHER INFORMATION: This sequence may encompass 3-10 'ngc'
      repeating units
<220> FEATURE:
<221> NAME/KEY: modified_base
<222> LOCATION: (4)..(4)
<223> OTHER INFORMATION: a, c, t, g, unknown or other
<220> FEATURE:

```
<221> NAME/KEY: modified_base
<222> LOCATION: (7)..(7)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: modified_base
<222> LOCATION: (16)..(16)
<223> OTHER INFORMATION: a, c, t, g, unknown or other
<220> FEATURE:
<221> NAME/KEY: modified_base
<222> LOCATION: (19)..(19)
<223> OTHER INFORMATION: a, c, t, g, unknown or other
<220> FEATURE:
<221> NAME/KEY: modified_base
<222> LOCATION: (22)..(22)
<223> OTHER INFORMATION: a, c, t, g, unknown or other
<220> FEATURE:
<221> NAME/KEY: modified_base
<222> LOCATION: (25)..(25)
<223> OTHER INFORMATION: a, c, t, g, unknown or other
<220> FEATURE:
<221> NAME/KEY: modified_base
<222> LOCATION: (28)..(28)
<223> OTHER INFORMATION: a, c, t, g, unknown or other

<400> SEQUENCE: 30
ngcngcngcn gcngcngcng cngcngcngc                                              30

<210> SEQ ID NO 31
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(30)
<223> OTHER INFORMATION: This sequence may encompass 3-10 'gnc'
      repeating units
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (8)..(8)
<223> OTHER INFORMATION: a, c, t, g, unknown or other
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other
<220> FEATURE:
<221> NAME/KEY: modified_base
<222> LOCATION: (17)..(17)
<223> OTHER INFORMATION: a, c, t, g, unknown or other
<220> FEATURE:
<221> NAME/KEY: modified_base
<222> LOCATION: (20)..(20)
<223> OTHER INFORMATION: a, c, t, g, unknown or other
<220> FEATURE:
<221> NAME/KEY: modified_base
```

```
<222> LOCATION: (23)..(23)
<223> OTHER INFORMATION: a, c, t, g, unknown or other
<220> FEATURE:
<221> NAME/KEY: modified_base
<222> LOCATION: (26)..(26)
<223> OTHER INFORMATION: a, c, t, g, unknown or other
<220> FEATURE:
<221> NAME/KEY: modified_base
<222> LOCATION: (29)..(29)
<223> OTHER INFORMATION: a, c, t, g, unknown or other

<400> SEQUENCE: 31
gncgncgncg ncgncgncgn cgncgncgnc                               30

<210> SEQ ID NO 32
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(40)
<223> OTHER INFORMATION: This sequence may encompass 3-10 'cagg'
      repeating units

<400> SEQUENCE: 32
caggcaggca ggcaggcagg caggcaggca ggcaggcagg                    40

<210> SEQ ID NO 33
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(50)
<223> OTHER INFORMATION: This sequence may encompass 3-10 'agaat'
      repeating units

<400> SEQUENCE: 33
agaatagaat agaatagaat agaatagaat agaatagaat agaatagaat         50

<210> SEQ ID NO 34
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(120)
<223> OTHER INFORMATION: This sequence may encompass 3-10 'cgcg4cg4'
      repeating units

<400> SEQUENCE: 34
cgcggggcgg ggcgcggggc ggggcgcggg gcggggcgcg gggcggggcg cggggcgggg    60
cgcggggcgg ggcgcggggc ggggcgcggg gcggggcgcg gggcggggcg cggggcgggg   120

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 35
gctgctgctg ctgctgctgc t                                          21

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Arg Arg Arg Arg Arg Arg Gly
1               5

<210> SEQ ID NO 37
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(60)
<223> OTHER INFORMATION: This sequence may encompass 3-10 'ggcccc'
      repeating units; see specification as filed for detailed
      description of substitutions and preferred embodiments.

<400> SEQUENCE: 37
ggccccggcc ccggccccgg ccccggcccc ggccccggcc ccggccccgg ccccggcccc    60

<210> SEQ ID NO 38
<211> LENGTH: 84
<212> TYPE: DNA
<213> ORGANISM: Homo sapiens

<400> SEQUENCE: 38
cagcagcagc agcagcagca gcagcagcag cagcagcagc agcagcagca gcagcagcag    60
cagcagcagc agcagcagca gcag                                          84

<210> SEQ ID NO 39
<211> LENGTH: 240
<212> TYPE: DNA
<213> ORGANISM: Homo sapiens

<400> SEQUENCE: 39
cagcagcagc agcagcagca gcagcagcag cagcagcagc agcagcagca gcagcagcag    60
cagcagcagc agcagcagca gcagcagcag cagcagcagc agcagcagca gcagcagcag   120
cagcagcagc agcagcagca gcagcagcag cagcagcagc agcagcagca gcagcagcag   180
cagcagcagc agcagcagca gcagcagcag cagcagcagc agcagcagca gcagcagcag   240

<210> SEQ ID NO 40
<211> LENGTH: 39
<212> TYPE: DNA
<213> ORGANISM: Homo sapiens

<400> SEQUENCE: 40
cagcagcagc agcagcagca gcagcagcag cagcagcag                          39

<210> SEQ ID NO 41
<211> LENGTH: 207

-continued

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
cagcagcagc agcagcagca gcagcagcag cagcagcagc agcagcagca gcagcagcag      60
cagcagcagc agcagcagca gcagcagcag cagcagcagc agcagcagca gcagcagcag     120
cagcagcagc agcagcagca gcagcagcag cagcagcagc agcagcagca gcagcagcag     180
cagcagcagc agcagcagca gcagcag                                         207

<210> SEQ ID NO 42
<211> LENGTH: 335
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(51)
<223> OTHER INFORMATION: a, c, t, g, unknown or other
<220> FEATURE:
<221> NAME/KEY: misc_feature
<222> LOCATION: (1)..(51)
<223> OTHER INFORMATION: n is a, c, g, or t
<220> FEATURE:
<221> NAME/KEY: modified_base
<222> LOCATION: (259)..(335)
<223> OTHER INFORMATION: a, c, t, g, unknown or other
<220> FEATURE:
<221> NAME/KEY: misc_feature
<222> LOCATION: (259)..(335)
<223> OTHER INFORMATION: n is a, c, g, or t

<400> SEQUENCE: 42
nnnnnnnnnn nnnnnnnnnn nnnnnnnnnn nnnnnnnnnn nnnnnnnnnn ncagcagcag      60
cagcagcagc agcagcagca gcagcagcag cagcagcagc agcagcagca gcagcagcag     120
cagcagcagc agcagcagca gcagcagcag cagcagcagc agcagcagca gcagcagcag     180
cagcagcagc agcagcagca gcagcagcag cagcagcagc agcagcagca gcagcagcag     240
cagcagcagc agcagcagnn nnnnnnnnnn nnnnnnnnnn nnnnnnnnnn nnnnnnnnnn     300
nnnnnnnnnn nnnnnnnnnn nnnnnnnnnn nnnnn                                335

<210> SEQ ID NO 43
<211> LENGTH: 12
<212> TYPE: DNA
<213> ORGANISM: Homo sapiens

<400> SEQUENCE: 43
ccccgccccg cg                                                          12

<210> SEQ ID NO 44
<211> LENGTH: 12
<212> TYPE: DNA
<213> ORGANISM: Homo sapiens

<400> SEQUENCE: 44
cgcggggcgg gg                                                          12

<210> SEQ ID NO 45
<211> LENGTH: 30
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(30)
<223> OTHER INFORMATION: This sequence may encompass 3-10 'gct'
      repeating units

<400> SEQUENCE: 45
gctgctgctg ctgctgctgc tgctgctgct                                          30

<210> SEQ ID NO 46
<211> LENGTH: 180
<212> TYPE: DNA
<213> ORGANISM: Homo sapiens

<400> SEQUENCE: 46
cagcagcagc agcagcagca gcagcagcag cagcagcagc agcagcagca gcagcagcag         60
cagcagcagc agcagcagca gcagcagcag cagcagcagc agcagcagca gcagcagcag        120
cagcagcagc agcagcagca gcagcagcag cagcagcagc agcagcagca gcagcagcag        180
```